(12) United States Patent
Augustine et al.

(10) Patent No.: US 11,160,710 B1
(45) Date of Patent: *Nov. 2, 2021

(54) RELOCATION MODULE AND METHODS FOR SURGICAL EQUIPMENT

(71) Applicant: Augustine Biomedical + Design, LLC, Eden Prairie, MN (US)

(72) Inventors: Scott D. Augustine, Deephaven, MN (US); Susan D. Augustine, Deephaven, MN (US); Garrett J. Augustine, Deephaven, MN (US); Brent M. Augustine, Savage, MN (US); Ryan S. Augustine, Minneapolis, MN (US); Randall C. Arnold, Minnetonka, MN (US)

(73) Assignee: Augustine Biomedical + Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/167,681

(22) Filed: Feb. 4, 2021

Related U.S. Application Data

(63) Continuation-in-part of application No. 17/092,681, filed on Nov. 9, 2020, now Pat. No. 10,993,865, (Continued)

(51) Int. Cl.
*A61G 13/10* (2006.01)
*A61B 50/13* (2016.01)
(Continued)

(52) U.S. Cl.
CPC ............ *A61G 13/108* (2013.01); *A61B 50/13* (2016.02); *A61B 50/15* (2016.02); *A61M 16/06* (2013.01); *A61M 16/18* (2013.01); *A61B 46/10* (2016.02); *A61B 90/50* (2016.02); *A61B 2050/155* (2016.02); *A61M 16/01* (2013.01); *B01D 46/0093* (2013.01)

(58) Field of Classification Search
CPC ..... A61G 13/108; A61M 16/06; A61M 16/18; A61M 16/01; A61B 50/13; A61B 50/15; A61B 46/10; A61B 90/50; A61B 2050/155; B01D 46/0093
USPC ........ 55/385.1, 385.2, 385.4, 467, 473, 485, 55/410, 356; 96/134, 146; 604/319, 322, 604/902
See application file for complete search history.

(56) References Cited

U.S. PATENT DOCUMENTS 4,105,028 A 8/1978 Sadlier et al.
4,531,956 A 7/1985 Howorth
(Continued)

FOREIGN PATENT DOCUMENTS

WO WO-2019191081 A1 10/2019

OTHER PUBLICATIONS

"U.S. Appl. No. 15/935,524, Corrected Notice of Allowability dated Jul. 18, 2019", 2 pgs.
(Continued)

*Primary Examiner* — Minh Chau T Pham
(74) *Attorney, Agent, or Firm* — Schwegman Lundberg & Woessner, P.A.

(57) ABSTRACT

Modules for housing electronic and electromechanical medical equipment including a system to measure and record administration of one or more IV medications or fluids for IV administration.

20 Claims, 23 Drawing Sheets

Related U.S. Application Data which is a continuation of application No. 16/879,406, filed on May 20, 2020, now Pat. No. 10,869,800.

(51) Int. Cl.
| | |
|---|---|
| *A61B 46/10* | (2016.01) |
| *A61B 90/50* | (2016.01) |
| *A61M 16/01* | (2006.01) |
| *A61B 50/15* | (2016.01) |
| *A61M 16/06* | (2006.01) |
| *A61M 16/18* | (2006.01) |
| *B01D 46/00* | (2006.01) |

(56) References Cited

U.S. PATENT DOCUMENTS

| | | | |
|---|---|---|---|
| 5,399,007 A | 3/1995 | Marconet | |
| 5,409,511 A | 4/1995 | Paul | |
| 5,516,313 A | 5/1996 | Lumpkin | |
| 5,695,536 A | 12/1997 | Fabrizi | |
| 7,597,731 B2 | 10/2009 | Palmerton et al. | |
| 7,674,436 B1 | 3/2010 | Feldman et al. | |
| 7,753,977 B2 | 7/2010 | Lyons et al. | |
| 9,603,956 B2 | 3/2017 | Newham | |
| 10,507,153 B2 | 12/2019 | Augustine et al. | |
| 10,512,191 B2 | 12/2019 | Augustine et al. | |
| 10,652,577 B2 | 5/2020 | Thoreau et al. | |
| 10,653,577 B2 | 5/2020 | Augustine et al. | |
| 10,702,436 B2 | 7/2020 | Augustine et al. | |
| 10,869,800 B2 * | 12/2020 | Augustine | A61B 90/98 |
| 10,888,482 B2 | 1/2021 | Augustine et al. | |
| 10,993,865 B2 | 5/2021 | Augustine et al. | |
| 11,045,377 B2 | 6/2021 | Augustine et al. | |
| 2001/0035702 A1 | 11/2001 | Murphy et al. | |
| 2003/0033790 A1 | 2/2003 | Hague | |
| 2003/0150328 A1 | 8/2003 | Hansson et al. | |
| 2004/0103789 A1 | 6/2004 | Lan et al. | |
| 2004/0176984 A1 * | 9/2004 | White | G16H 20/17 705/2 |
| 2004/0247016 A1 * | 12/2004 | Faries, Jr. | A61B 50/13 374/162 |
| 2004/0249673 A1 | 12/2004 | Smith | |
| 2005/0060974 A1 | 3/2005 | Palmerton et al. | |
| 2005/0087256 A1 | 4/2005 | Clark | |
| 2005/0097870 A1 | 5/2005 | Moshenrose | |
| 2006/0042205 A1 | 3/2006 | Kalous et al. | |
| 2007/0199287 A1 | 8/2007 | Wiser | |
| 2007/0225690 A1 | 9/2007 | Sekiguchi et al. | |
| 2008/0097315 A1 | 4/2008 | Miner et al. | |
| 2008/0173178 A1 | 7/2008 | Metteer | |
| 2009/0188311 A1 * | 7/2009 | Cadieux | A61M 5/1684 73/149 |
| 2010/0094262 A1 | 4/2010 | Tripathi et al. | |
| 2010/0324380 A1 | 12/2010 | Perkins et al. | |
| 2011/0030560 A1 | 2/2011 | Bohlen et al. | |
| 2011/0196304 A1 | 8/2011 | Kramer et al. | |
| 2011/0317004 A1 | 12/2011 | Tao | |
| 2012/0024154 A1 | 2/2012 | Augustine et al. | |
| 2012/0154120 A1 | 6/2012 | Alloro et al. | |
| 2012/0305787 A1 | 12/2012 | Henson | |
| 2013/0041258 A1 | 2/2013 | Patrick et al. | |
| 2013/0243647 A1 | 9/2013 | Garner et al. | |
| 2014/0262553 A1 | 9/2014 | Pollock et al. | |
| 2015/0168207 A1 | 6/2015 | Pollock et al. | |
| 2015/0224237 A1 | 8/2015 | Reasoner et al. | |
| 2016/0188831 A1 | 6/2016 | Kurtz et al. | |
| 2016/0362234 A1 | 12/2016 | Peret et al. | |
| 2016/0379504 A1 | 12/2016 | Bailey et al. | |
| 2017/0112954 A1 | 4/2017 | Dayton | |
| 2017/0209658 A1 | 7/2017 | Tobia et al. | |
| 2017/0333626 A1 | 11/2017 | Mansour | |
| 2018/0132966 A1 | 5/2018 | Désauliniers et al. | |
| 2019/0105120 A1 | 4/2019 | Norman et al. | |
| 2019/0290524 A1 | 9/2019 | Augustine et al. | |
| 2019/0297745 A1 | 9/2019 | Augustine et al. | |
| 2019/0328598 A1 | 10/2019 | Mangiardi | |
| 2019/0357382 A1 | 11/2019 | Augustine et al. | |
| 2020/0121496 A1 | 4/2020 | Prokop et al. | |
| 2020/0230316 A1 | 7/2020 | Guerra et al. | |
| 2020/0281790 A1 | 9/2020 | Augustine et al. | |
| 2020/0289354 A1 | 9/2020 | Augustine et al. | |
| 2021/0196550 A1 | 7/2021 | Augustine et al. | |
| 2021/0251835 A1 | 8/2021 | Augustine et al. | |

OTHER PUBLICATIONS

"U.S. Appl. No. 15/935,524, Corrected Notice of Allowability dated Aug. 21, 2019", 2 pgs.

"U.S. Appl. No. 15/935,524, Non Final Office Action dated Mar. 8, 2019", 8 pgs.

"U.S. Appl. No. 15/935,524, Non Final Office Action dated Sep. 19, 2018", 8 pgs.

"U.S. Appl. No. 15/935,524, Notice of Allowance dated Jun. 12, 2019", 9 pgs.

"U.S. Appl. No. 15/935,524, Response filed May 15, 2019 to Non Final Office Action dated Mar. 8, 2019", 10 pgs.

"U.S. Appl. No. 15/935,524, Response filed Dec. 12, 2018 to Non Final Office Action dated Sep. 19, 2018", 18 pgs.

"U.S. Appl. No. 16/364,884, Corrected Notice of Allowability dated Aug. 29, 2019", 3 pgs.

"U.S. Appl. No. 16/364,884, Corrected Notice of Allowability dated Nov. 8, 2019", 3 pgs.

"U.S. Appl. No. 16/364,884, Non Final Office Action dated Jul. 3, 2019", 9 pgs.

"U.S. Appl. No. 16/364,884, Notice of Allowance dated Aug. 20, 2019", 10 pgs.

"U.S. Appl. No. 16/364,884, Response filed Jun. 18, 2019 to Restriction Requirement dated May 1, 2019", 9 pgs.

"U.S. Appl. No. 16/364,884, Response filed Jul. 24, 2019 to Non Final Office Action dated Jul. 3, 2019", 9 pgs.

"U.S. Appl. No. 16/364,884, Restriction Requirement dated May 1, 2019", 5 pgs.

"U.S. Appl. No. 16/519,677, Non Final Office Action dated Nov. 13, 2019", 6 pgs.

"U.S. Appl. No. 16/519,677, Response filed Dec. 17, 2019 to Non Final Office Action dated Nov. 13, 2019", 9 pgs.

"U.S. Appl. No. 16/529,283, Non Final Office Action dated Sep. 18, 2019", 8 pgs.

"U.S. Appl. No. 16/529,283, Notice of Allowance dated Jan. 10, 2020", 10 pgs.

"U.S. Appl. No. 16/529,283, Response filed Dec. 13, 2019 to Non Final Office Action dated Sep. 18, 2019", 8 pgs.

"U.S. Appl. No. 16/601,924, Non Final Office Action dated Dec. 5, 2019", 6 pgs.

"U.S. Appl. No. 16/879,406, Corrected Notice of Allowability dated Oct. 21, 2020", 2 pgs.

"U.S. Appl. No. 16/879,406, Non Final Office Action dated Jun. 9, 2020", 9 pgs.

"U.S. Appl. No. 16/879,406, Notice of Allowance dated Sep. 10, 2020", 8 pgs.

"U.S. Appl. No. 16/879,406, Response filed Sep. 2, 2020 to Non Final Office Action dated Jun. 9, 2020", 12 pgs.

"U.S. Appl. No. 16/885,715, Non Final Office Action dated Jun. 23, 2020", 9 pgs.

"U.S. Appl. No. 16/885,715, Notice of Allowance dated Sep. 22, 2020", 8 pgs.

"U.S. Appl. No. 16/885,715, Notice of Non-Compliant Amendment dated Sep. 10, 2020", 2 pgs.

"U.S. Appl. No. 16/885,715, Response filed Sep. 2, 2020 to Non Final Office Action dated Jun. 23, 2020", 12 pgs.

"U.S. Appl. No. 16/885,715, Response filed Sep. 14, 2020 to Notice of Non-Compliant Amendment dated Sep. 10, 2020", 12 pgs.

"U.S. Appl. No. 17/092,681, Non Final Office Action dated Dec. 17, 2020", 8 pgs.

"U.S. Appl. No. 17/092,681, Notice of Allowance dated Feb. 2, 2021", 9 pgs.

"U.S. Appl. No. 17/092,681, Response filed Jan. 22, 2021 to Non Final Office Action dated Dec. 17, 2020", 13 pgs.

(56) References Cited

OTHER PUBLICATIONS

"U.S. Appl. No. 17/103,426, Non Final Office Action dated Jan. 25, 2021", 8 pgs.
"International Application Serial No. PCT/US2019/024054, International Preliminary Report on Patentability dated Oct. 8, 2020", 9 pgs.
"International Application Serial No. PCT/US2019/024054, International Search Report dated Jul. 25, 2019", 5 pgs.
"International Application Serial No. PCT/US2019/024054, Invitation to Pay Additional Fees dated May 29, 2019", 3 pgs.
"International Application Serial No. PCT/US2019/024054, Written Opinion dated Jul. 25, 2019", 7 pgs.
"International Application Serial No. PCT/US2020/033804, International Search Report dated Aug. 28, 2020", 3 pgs.
"International Application Serial No. PCT/US2020/033804, Written Opinion dated Aug. 28, 2020", 10 pgs.
"U.S. Appl. No. 17/199,722, Notice of Allowance dated Jul. 26, 21", 9 pgs.
"U.S. Appl. No. 17/199,722, Response filed Jul. 14, 2021 to Non Final Office Action dated May 12, 2021", 15 pgs.
"U.S. Appl. No. 17/245,942, Non Final Office Action dated Jun. 30, 2021", 11 pgs.
"U.S. Appl. No. 17/245,942, Notice of Allowance dated Jul. 27, 2021", 9 pgs.
"U.S. Appl. No. 17/245,942, Response filed Jul. 14, 2021 to Non Final Office Action dated Jun. 30, 2021", 14 pgs.
"U.S. Appl. No. 17/308,437, Non Final Office Action dated Jul. 15, 2021", 8 pgs.
"U.S. Appl. No. 17/332,523, Non Final Office Action dated Jul. 29, 2021", 8 pgs.
"International Application Serial No. PCT/US2021/016585, International Search Report dated Jun. 30, 21", 5 pgs.
"International Application Serial No. PCT/US2021/016585, Written Opinion dated Jun. 30, 21", 13 pgs.
"U.S. Appl. No. 17/199,722, Non Final Office Action dated May 12, 2021", 7 pgs.
"International Application Serial No. PCT US2021 030182, International Search Report dated Aug. 16, 2021", 2 pgs.
"International Application Serial No. PCT US2021 030182, Written Opinion dated Aug. 16, 2021", 17 pgs.

\* cited by examiner

RELOCATION MODULE AND METHODS FOR SURGICAL EQUIPMENT

PRIORITY

This application is a continuation-in-part of U.S. application Ser. No. 17/092,681, filed Nov. 9, 2020, which is a continuation of U.S. application Ser. No. 16/879,406, filed May 20, 2020, now issued as U.S. Pat. No. 10,869,800. The disclosure of all of these applications are incorporated herein by reference in their entirety.

TECHNICAL FIELD

This document pertains generally, but not by way of limitation, to systems and methods that provide a "chain of custody" for medications, from the time of issuance from the pharmacy until the administration to the patient, to assure the right drug is administered to the right patient and to prevent pilferage of scheduled drugs such as narcotics, by the medical staff. This document also pertains generally to systems and methods for improving safety for patients receiving intravenous (IV) medications and fluids, by avoiding medication or fluid errors and documenting the administration.

BACKGROUND

Many medications are given intravenously (IV) to patients all throughout the healthcare system, including but not limited to: in the operating room (OR), the emergency room (ER), intensive care unit (ICU), the ward and the clinic. Medication security, especially for scheduled drugs such as narcotics is an ongoing challenge for healthcare systems. Narcotics, for example, can be securely stored, tracked and accounted for in the pharmacy or medication dispensing machine. However, once the drug is checked out of the pharmacy or medication dispensing machine, there is no further security and whether that specific drug is administered to the patient as intended or is stolen by the healthcare provider who may be addicted, is entirely dependent on the integrity of the individual provider.

In general, at this date there is no way to track or monitor each dose of a narcotic between when it is checked out of the pharmacy or medication dispensing machine and when it is injected into the patient. In other words, the final link in the "chain of custody" for that drug relies solely on the personal integrity of the healthcare provider administering the drug. It is not uncommon for drug addicted healthcare providers to steal narcotics after checking them out and then load or reload the syringe with any clear fluid such as saline which is then injected into the patient's IV line.

There is a need for a security system for IV medications that can track each dose of medication form the time it is checked out of the pharmacy or medication dispensing machine until it is injected into the patients IV. In other words, there is a need for an automatic system that monitors and documents the final link in the "chain of custody" for that drug dose and does not rely on the personal integrity of the healthcare provider administering the drug.

SUMMARY

In some examples, the security system for IV medications of this disclosure provides medication security for scheduled drugs such as narcotics. The specific syringe or bottle or ampule of the drug may be labeled with and RFID tag, a barcode, QR code marking or other machine-identifiable label ("barcode" and "QR code" are used interchangeably in this disclosure and can include any type of readable image or code). The specific syringe, bottle, ampule or vial of the drug is identified by the RFID tag or barcode and its identity is automatically documented when it is checked out of the pharmacy. In some examples, the healthcare provider may also be positively identified by RFID or barcode identification that may be attached to a healthcare provider's ID badge, for example. The final link in the "chain of custody" for a specific drug dose begins when a provider scans their ID badge in order to check the specific drug out from the pharmacy or medication dispensing machine.

In some examples, the security system for IV medications at the patient's bedside uses the RFID or barcode on the provider's ID badge to identify the person injecting the medication or administering the fluid. In some examples, the security system for IV medications at the patient's bedside uses the RFID or barcode on the injection syringe to identify the specific dose of that drug that was checked out of the pharmacy or medication dispensing machine. Having established the identity of the person giving the injection and identified the contents of the injection syringe, the security system for IV medications "watches" the drug being injected into the IV line using machine vision, documenting that the specific drug was given to the patient. When the injection is complete, the "chain of custody" from the pharmacy to the patient for that drug dose can be considered complete. This is especially important for scheduled medications such as narcotics, where pilferage by the medical staff has been known to occur.

In some examples, tamper-proof, non-refillable syringes may be desirable to assure that the RFID tagged or barcode labeled syringe was not emptied of its drug while enroute to the patient and then reloaded with saline before injecting into the patient.

The safety and security system for IV medications and fluids can also make an automatic electronic record of medication and fluid delivery to the patient. The electronic record may have many names including but not limited to the electronic anesthetic record (EAR), the electronic surgical record (ESR), the electronic medical record (EMR) or the electronic health record (EHR). In this disclosure we will use "electronic medical record" (EMR) to generally refer to all electronic records.

In some examples, the security system for IV medications of this disclosure includes a system for automatically measuring and recording the administration of IV medications and fluids. The automated EMR relies on automatic IV medication and fluids data entry. The system for automatically measuring and recording the administration of IV medications and fluids can include one or more sensors, such as, but limited to, one or more of a barcode reader or an RFID interrogator for accurately identifying a medication or fluid for IV administration.

The system for automatically measuring and recording the administration of IV medications and fluids can also include, or can instead include, one or more digital cameras with machine vision software ("machine vision") for accurately measuring the volume of medication administered from a syringe or fluid administered from an IV bag through a drip chamber into an IV tubing. The digital cameras with machine vision software essentially duplicate the clinician's vision of an activity, injection of a drug from a syringe for example, without interfering in the normal activity and yet allows automatic recording of the activity in the EMR. The machine vision software can include one or more machine-readable mediums that when implemented on hardware processing circuitry of the system or in electrical communication with the system, can perform the functions described herein.

Doctors and nurses dislike record keeping and the switch to the electronic record has made the act of record keeping more difficult and time consuming. Entering the electronic record into the computer sometime after the event occurred, is not only distracting from patient care but leads to inaccurate records.

In some examples, the automatic EMR of the security system for IV medications of this disclosure lets the computer (e.g., a processor and memory for performing instructions) add to patient safety by checking drug identities, dosages, side effects, allergies, the patients' medical history and vital signs and alerting the clinician to potential problems or even physically stopping the drug administration. In some examples, the automatic EMR of this disclosure eliminates medication errors by checking the drug to be injected against the physician's medication orders before the injection can occur. In some examples, the automatic EMR of this disclosure is useful for managing drug inventories because a given medication administration is tied to a specific drug bottle or syringe. Finally, the computer mouse and keyboards have been shown to be contaminated by a wide variety of infective organisms and are virtually impossible to clean. Automatic data entry to the EMR would improve patient safety, improve clinician job satisfaction and improve medication inventory management.

In some examples, the automatic EMR of the security system for IV medications of this disclosure may also automatically record and display many other functions including but not limited to: IV fluid administration, medication infusions, the patient's vital signs, urine output, blood loss, ventilator settings, inspired gases, electrosurgical settings, pneumoperitoneum insufflation settings, RFID surgical sponge counts, surgical information and video, dialysis or other medical procedure information and patient activity.

In some examples, the automatic EMR of the security system for IV medications may allow remote viewing of the displayed patient information. In some examples, the remotely displayed patient information may be used for remote medical supervision such as an anesthesiologist providing remote supervision to a nurse anesthetist who is administering the anesthetic. In some examples, the remotely displayed patient information may be used for remote medical consultation. In some examples, the remotely displayed patient information may be used to document the involvement of remote medical supervision or consultation for billing purposes.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document. Any combination of the features shown and described in this disclosure, including combinations of fewer or more features is within the content of this disclosure. Modules, systems and methods including individual features described herein, without combinations of features as shown in the examples (for the sake of brevity), are also within the scope of this disclosure.

DETAILED DESCRIPTION

The following detailed description is exemplary in nature and is not intended to limit the scope, applicability, or configuration of the invention in any way. Rather, the following description provides practical illustrations for implementing exemplary examples of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

As described herein, operably coupled can include, but is not limited to, any suitable coupling, such as a fluid (e.g., liquid, gas) coupling, an electrical coupling or a mechanical coupling that enables elements described herein to be coupled to each other and/or to operate together with one another (e.g., function together).

Figure 1:
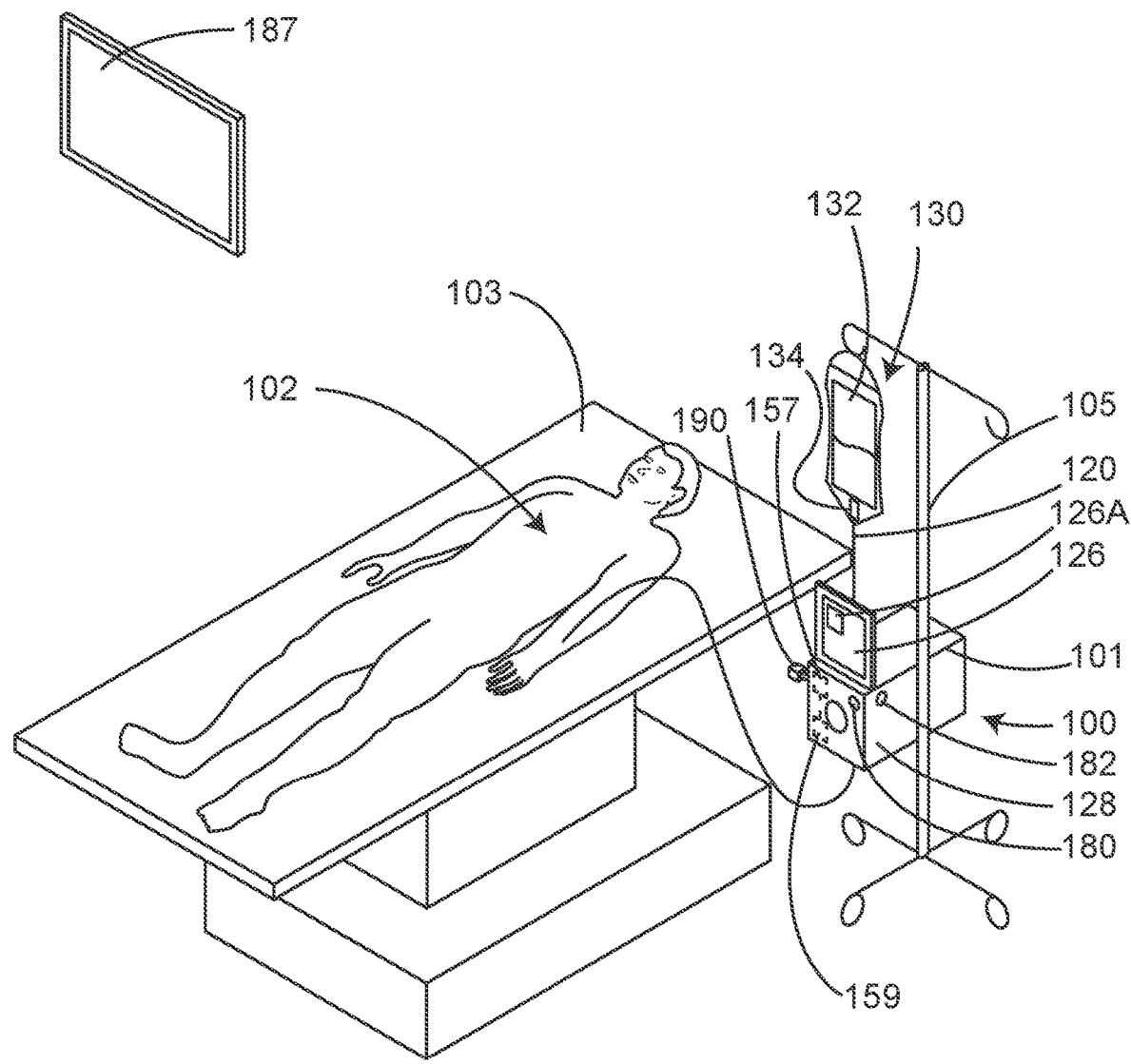
FIG. 1 illustrates an isometric view of an example module including a system for generating an automated electronic anesthetic record located proximate to a patient, in accordance with at least one example of this disclosure.

FIG. 1 illustrates an isometric view of an example safety and security system 100 for generating an automated electronic anesthetic record (EAR) or electronic medical record (EMR) located proximate to a patient. Some aspects of FIG. 1 are also described with respect to the description of other figures, including FIG. 14.

As shown in FIG. 1, the safety and security system for intravenous (IV) medications 100 may be attached to and portions can be stored within a module 101. The module 101 can conveniently provide direct access to the patient 102. An IV pole 105 may provide a convenient mounting support location for the safety and security system for IV medications 100 (hereinafter, "safety and security system 100"). In some examples, the components and systems of the safety and security system 100 of this disclosure can be supported by other mounting supports, including but not limited to a boom-mounted rack system, a wheeled rack system and a bed 103 mounting bracket. One or more computers including processing circuitry 157, of the safety and security system 100 of this disclosure may be conveniently and safely housed inside the module 101.

In some examples, it is anticipated that some or all of the components of the safety and security system 100 of this disclosure could be used in other healthcare settings such as the intensive care unit, the emergency room or on the ward. As shown in FIG. 1, the module 101 may be mounted on an IV pole 105 or other suitable mounting structure located near the patient 102.

In some examples, a touch-screen electronic record display 126 can convert to a qwerty-type keyboard to allow uncommon anesthetic and surgical events or deviations from pre-recorded scripts, to be manually documented. This allows the standard computer keyboard that is used for data entry in most electronic anesthetic records, to be eliminated. Standard keyboards are known to be contaminated with pathogenic organisms and are nearly impossible to clean and decontaminate due to their irregular surfaces. In contrast, the smooth glass or plastic face of a touch-screen monitor is easy to clean with no crevasses to hide organisms.

In some examples, the safety and security system for IV medications 100 of this disclosure can include a system for automatically measuring and recording the administration of IV medications. In some examples, the system for automatically measuring and recording the administration of IV medications includes a medication identification and measurement system 128. In some examples, aspects of the safety and security system 100 can be provided together with or separately from other aspects of the IV medication identification and measurement system 128 (hereinafter, "medication identification and measurement system 128"). Likewise, aspects of the medication identification and measurement system 128 can be provided together with or separately from other aspects of the safety and security system 100.

Figure 2:
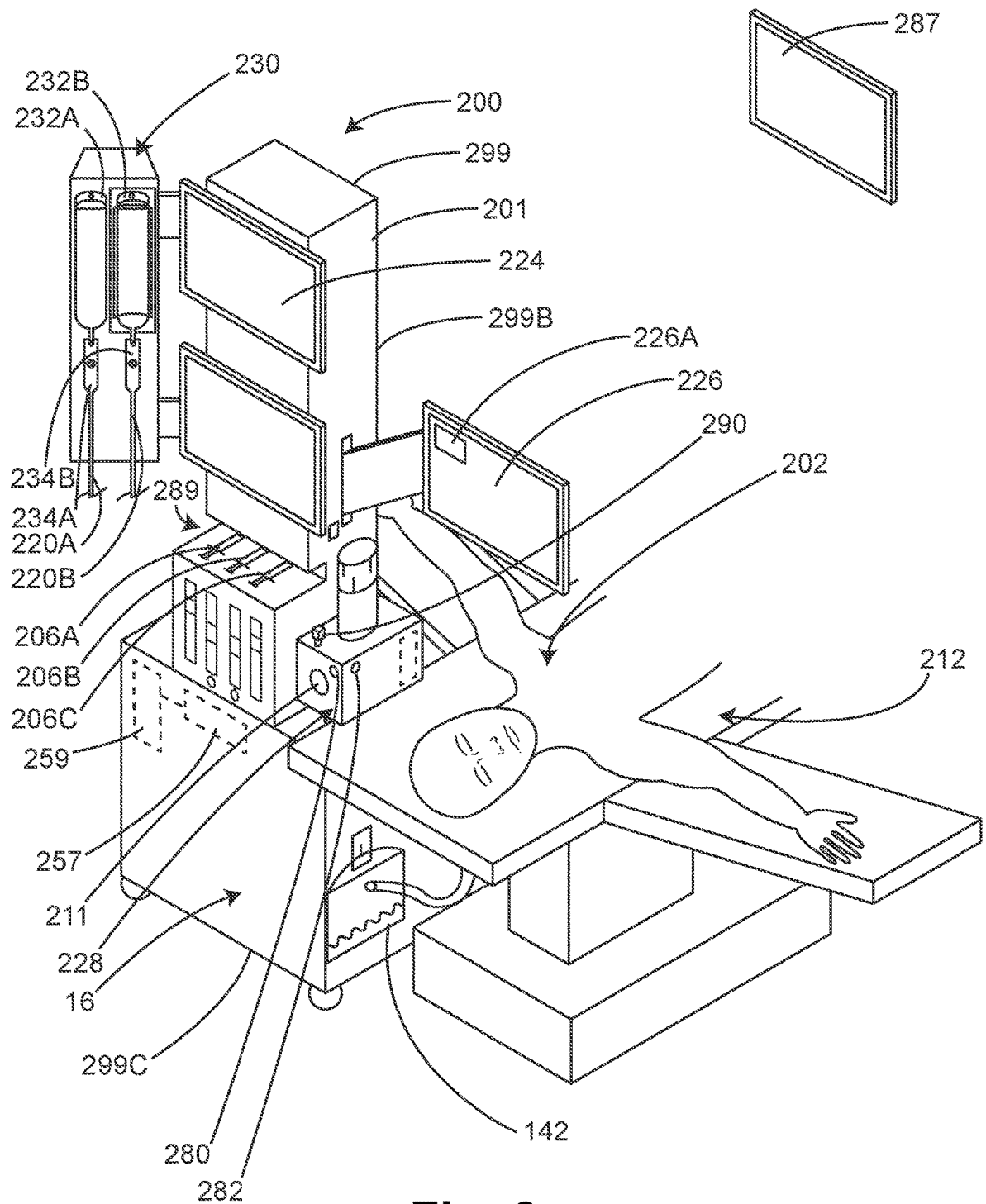
FIG. 2 illustrates an isometric view of an example module including a system for generating an automated electronic anesthetic record located proximate to a patient, in accordance with at least one example of this disclosure.

FIG. 2 illustrates an isometric view of an example safety and security system 200 for generating an automated electronic anesthetic record located proximate to a patient 202. Features of the safety and security system 100 of FIG. 1 may be included in the safety and security system 200 of FIG. 2, and vice-versa, therefore all aspects may not be described in further detail. Like numerals can represent like elements. Aspects of FIGS. 1 and 2 may also be described together. Some aspects of FIG. 2, including an IV fluid identification and measurement system 130, are described with respect other figures, including the description of IV fluid identification and measurement system 1430 of FIG. 14.

As shown in FIG. 2, an example medication identification and measurement system 228 may be attached to a relocation module 201 that may be advantageously positioned proximate the patient 202, such as near the patient's head on a surgical table 212. In this position medications can be conveniently administered by medical personnel while also tending to and observing the patient 202 during surgery.

In some examples, the medication identification and measurement system 128 (FIG. 1), 228 (FIG. 2) may include one or more sensors, such as one or more of: a barcode reader or QR code reader (e.g., 436, FIG. 4), a radio-frequency identification (RFID) interrogator (e.g., 438, FIG. 4), or any other suitable sensor for accurately and reliably identifying a medication for IV administration. As defined herein, a barcode reader can include any other type of identifying reader, such as, but not limited to, a QR code reader. Likewise, the RFID interrogator can be any type of interrogator and is not limited to those interrogators based on radio frequency. Examples of such sensors are described herein, such as in FIGS. 4 and 5.

In some examples, instead of, or in addition to one or more of an RFID interrogator 438 and a barcode reader 436, the medication identification and measurement system 128, 228 can receive an input to determine the identity. For example, the medication identification and measurement system 128, 228 can include one or more of: a sensor, such as barcode reader 436 of FIG. 4, configured to identify the one or more IV medications or fluids, or an input configured to receive the identity of the one or more IV medications or fluids, such as via the anesthetic record input component 224.

In some examples, the barcode reader (e.g., 436, FIG. 4) may be a "computer vision" or "machine vision" camera with the capability of reading barcodes. The term "machine vision" is often associated with industrial applications of a computer's ability to see, while the term "computer vision" is often used to describe any type of technology in which a computer is tasked with digitizing an image, processing the data it contains and taking some kind of action. In this disclosure the terms "machine vision" and "computer vision" may be used interchangeably. Traditionally, machine vision includes technology and methods used to provide imaging-based automatic inspection and analysis, process control, and robot guidance. Machine vision is sometimes used in manufacturing environments. Machine vision refers to many technologies, software and hardware products including processing circuitry, integrated systems and methods.

The inventors have discovered that machine vision can be useful beyond its traditional uses. The inventors discovered that machine vision can be advantageous in implementing a safety and security system 100, 200 because it offers reliable measurements, gauging, object recognition, pattern recognition and liquid fill level measurements. Machine vision does not get tired or distracted. Machine vision excels at quantitative measurement of a structured scene because of its speed, accuracy and repeatability. However, it does require the scene to be structured to perform the desired function.

Machine vision can be very accurate for measuring size of an object at a known distance or the distance of an object of known size. However, it cannot do both. Therefore, in some examples it is important to know the exact location of a syringe (e.g., 406, FIG. 4) and thus know the distance from the camera (e.g., 436, FIG. 4) to the syringe (e.g., 406, FIG. 4) in order for the machine vision to calculate the distance of the movement of the plunger (e.g., 446, FIG. 5) within the syringe (e.g., 406, FIG. 5). This is what we mean by the "scene being structured."

Machine vision may be advantageous for the safety and security system 100, 200 of this disclosure because it "sees" and measures, but does not touch or interfere with the healthcare provider doing their normal job of injecting medications or administering IV fluids. Further, the same visual image that is used by the machine vision software can be transmitted and displayed on a screen 126, 226 to give the operator (whose fingers can be pushing the plunger 446 of the syringe 406, a close-up view of the syringe 406. FIG. 5 is a cross-section view taken at 5-5 of FIG. 4. The machine vision camera 436 can be looking at the same view of the syringe 406 as the operator and it is the same or similar view that the operator would see if they were injecting IV medications the traditional way.

The machine vision camera, or digital camera, can include machine vision software, or the machine vision camera can be in electrical communication with (e.g., operably coupled to) one or more hardware processors, such as processing circuitry 157, 257 and one or more machine-readable mediums 159, 259. The one or more machine-readable mediums 159, 259 can include instructions (e.g., software), that when implemented on the processing circuitry 157, 257, can perform the functions described herein. The processing circuitry 157, 257 can be stored in the module 101, relocation module 201 or remote from the modules 101, 201 (e.g. in a wired or wireless manner). The one or more machine-readable mediums 159 can be a storage device, such as a memory located in the module 201 or remote from the module 101, 201.

In some examples, the RFID interrogator 438 may be either High Frequency (HF) or Near Field (NF) RFID in order to advantageously limit the read-range to a distance of less than 12 inches. In some examples, the RFID read-range may advantageously be limited, such as to less than 8 inches so that only a specific medication injection is identified at any time. In a possibly more preferred example, the RFID read-range may be limited to less than 4 inches to further prevent mis-readings. NF-RFID has a short read-range by definition and the read-range of HF-RFID can be easily limited by restricting the size of the antenna on the tag. In contrast, longer read-range RFID such as Ultra-high Frequency (UHF-RFID) may confusingly interrogate every RFID tag in the operating room and thus be unable to identify which medication is being delivered to the medication identification and measurement system 128, 228. However, any suitable RFID range for a particular application may be used.

Figure 3:
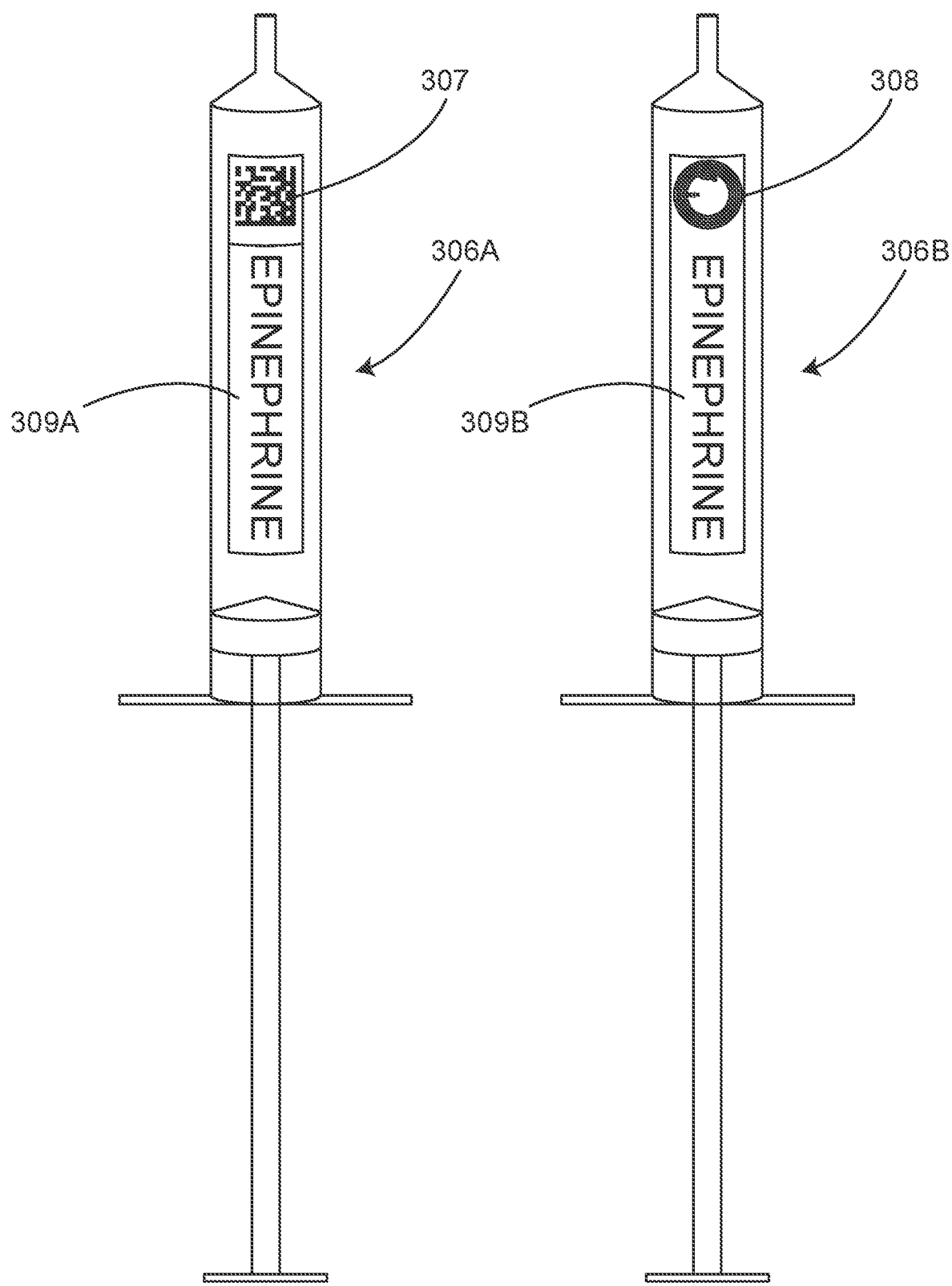
FIG. 3 illustrates a plan view of an example of preloaded syringes 200A and 200B that can be used with the system of FIGS. 1 and 2, in accordance with at least one example of this disclosure.

FIG. 3 illustrates a plan view of an example of preloaded syringes 306A and 306B that can be used with the safety and security system 200 of FIG. 2.

The one or more preloaded syringes 306A and 306B may be labeled with a unique barcode label 307 or an RFID tag 308 that may identify one or more of the drug, the concentration, the lot number, the expiration date, the manufacturer and other important information. In some examples, a unique barcode label 307 may be a "2-D" barcode label in order to include more information on a smaller area than traditional barcode labels. In some examples, the barcode label 307 or RFID tag 308 includes the drug identifying label 309A and 309B for convenient use by the caregiver.

In some examples, the syringes 306A and 306B can be filled at the point of use and may be labeled with drug labels 309A and 309B and either barcode labels 307 or RFID tags 308 that are removably attached to the drug bottle or vial at the factory or pharmacy. The drug labels 309A and 309B and either barcode labels 307 or RFID tags 308 may be easily removed from the drug bottle or vial and adhesively attached to the syringe 306A or 306B at the time that the syringe 306A or 306B is loaded with the drug by the caregiver. Instead of, or in addition to the barcode labels 307 or RFID tags 308, any other suitable "tag/reader" system known in the arts, may be used.

Figure 4:
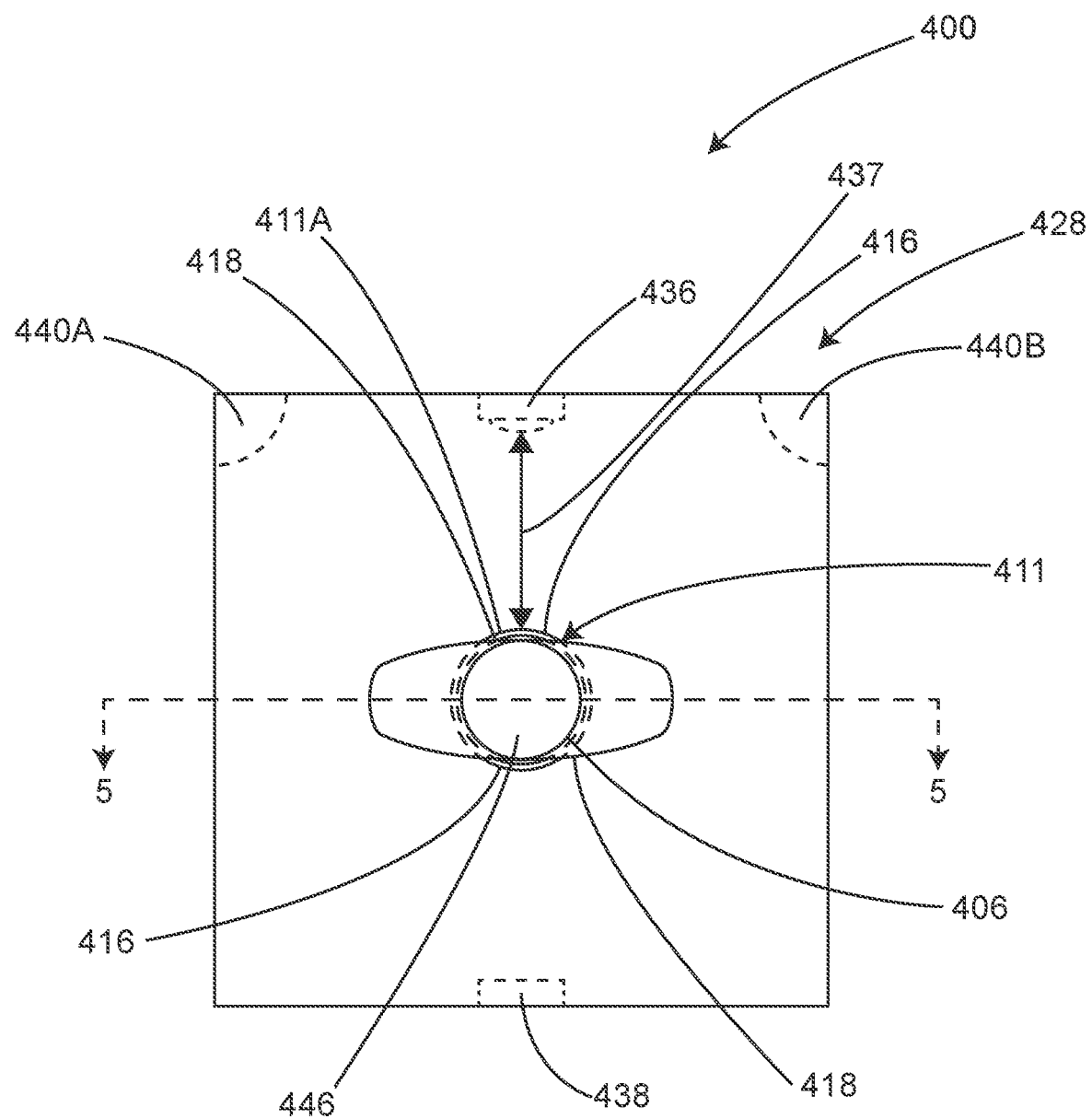
FIG. 4 illustrates a side view of an example medication identification and measurement system and a syringe that can be used with the system of FIGS. 1 and 2, to monitor drug delivery, in accordance with at least one example of this disclosure.
Figure 5:
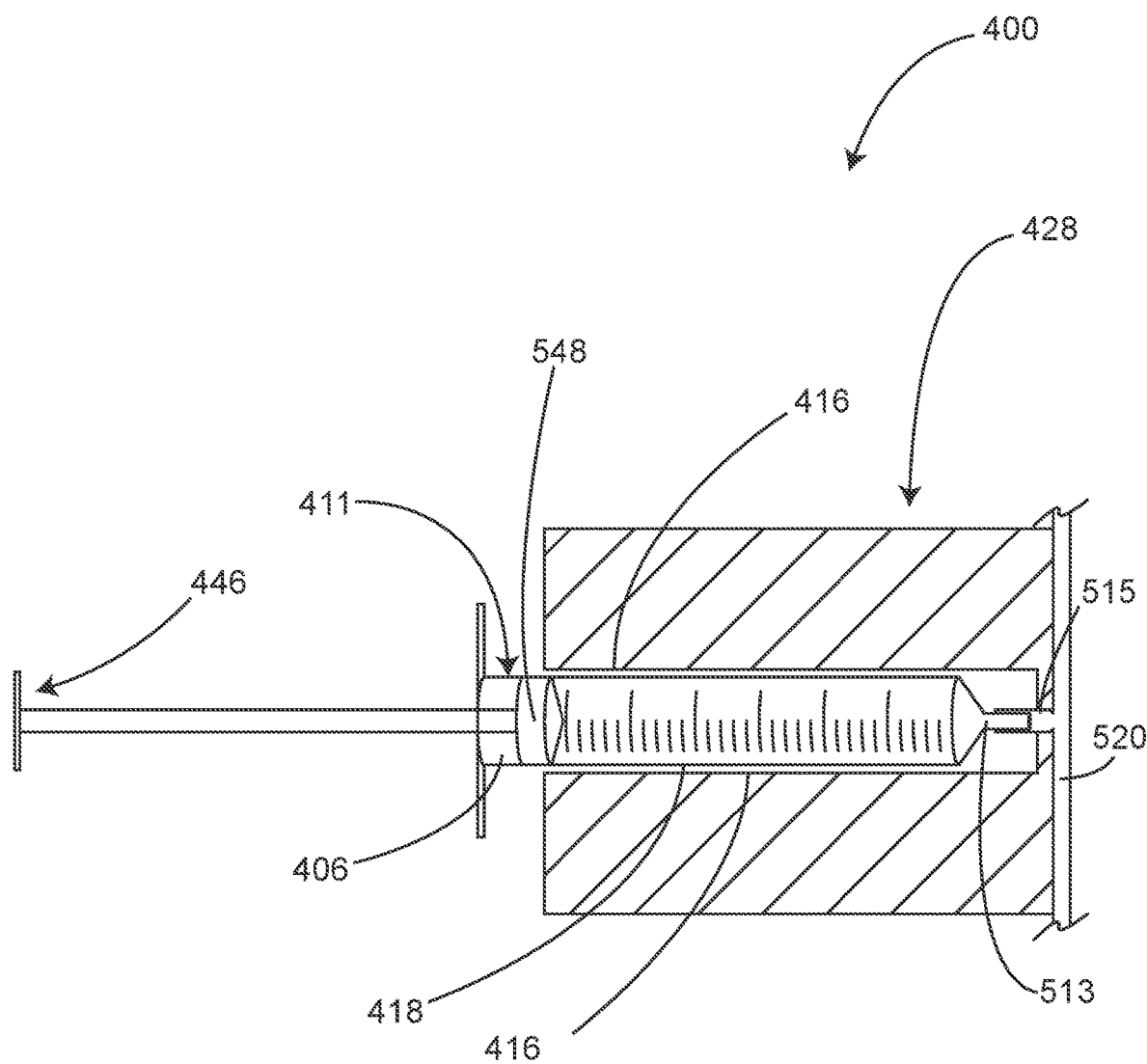
FIG. 5 illustrates a cross-sectional view of the medication identification and measurement system and a syringe (not shown in cross-section) of FIG. 4, taken along line 5-5, in accordance with at least one example of this disclosure.

FIGS. 4-10 illustrate examples of medication identification and measurement systems 428, 628, 828 that can be used with the safety and security systems 100, 200 of FIGS. 1 and 2. However, aspects of the medication identification and measurement systems 428, 628 and 828 may be used with other systems, and other medication identification and measurement systems may be used with the safety and security systems 100, 200. Furthermore, some examples of the safety and security systems 100, 200 can omit aspects of the medication identification and measurement systems, or can omit a medication identification and measurement system altogether. FIG. 4 illustrates a portion of a safety and security system 400 including a side view of an example medication identification and measurement system 428 and a syringe 406 that can be used with the safety and security systems 100, 200 of FIGS. 1 and 2, to monitor drug delivery. FIG. 5 illustrates a cross-sectional view of the medication identification and measurement system 428 and the syringe 406 (not shown in cross-section) of FIG. 4, taken along line 5-5. FIGS. 4 and 5 are described together.

As shown in FIGS. 4 and 5, the medication identification and measurement system 428 may include at least one injection portal 411. The injection portal 411 may be a receptacle for accommodating a syringe 406 in a fixed and known location and can be configured to orient the Luer taper connector 513 to mate with an injection port 515. The injection port 515 can be secured within the injection portal 411 and can be in fluid communication with IV tubing 520. In some examples, the injection portal 411 may include an injection portal tube 416, such as a transparent tube that is sized to receive and accommodate a syringe barrel 418 of a syringe 406. In some examples, the injection portal can be configured to receive a specific size syringe barrel 418. In some examples, multiple injection portals 411 can be provided to accommodate syringes 406 of different sizes.

Figure 6:
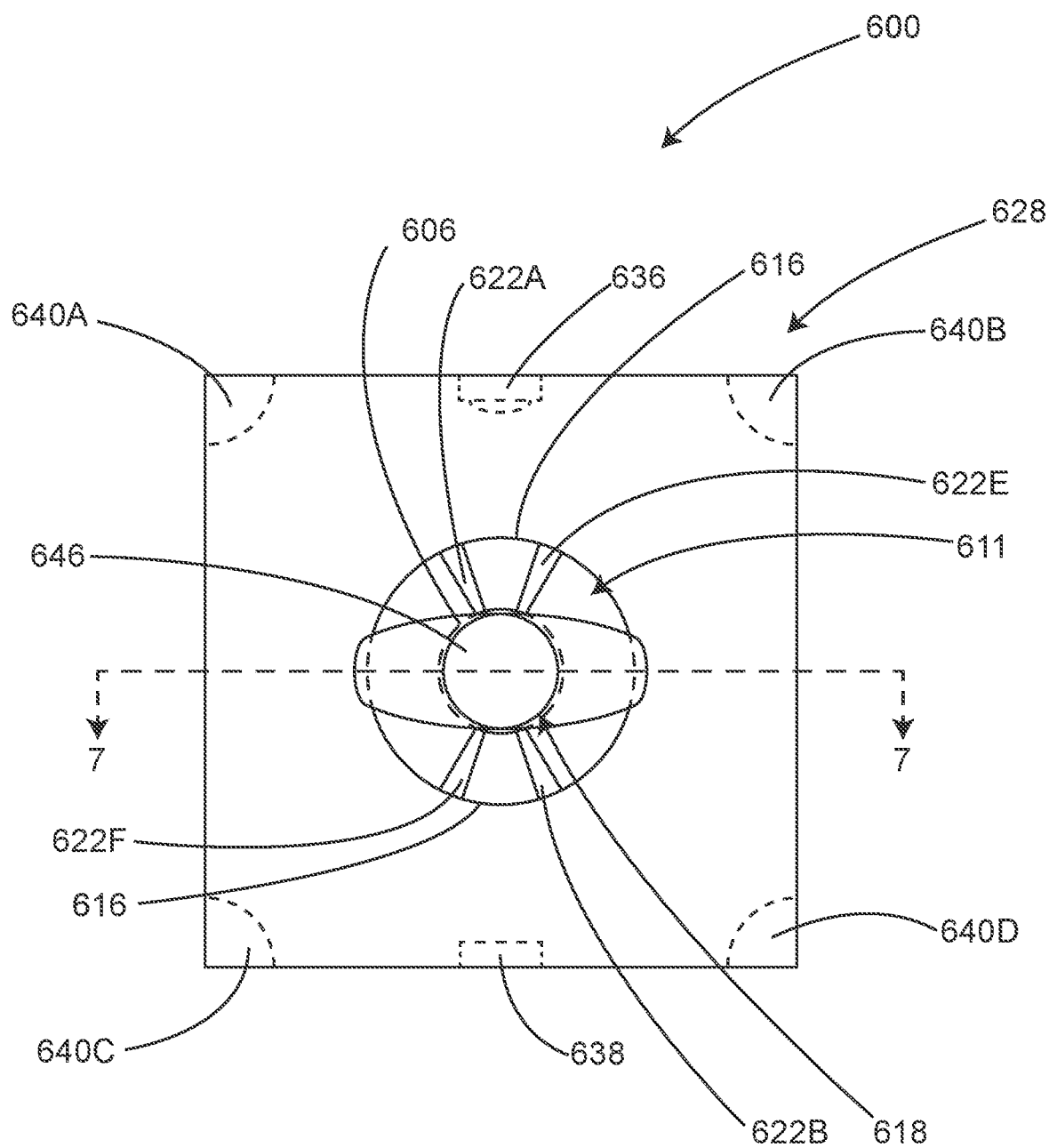
FIG. 6 illustrates a side view of a second example medication identification and measurement system and a syringe that can be used with the system of FIGS. 1 and 2, in accordance with at least one example of this disclosure.
Figure 7:
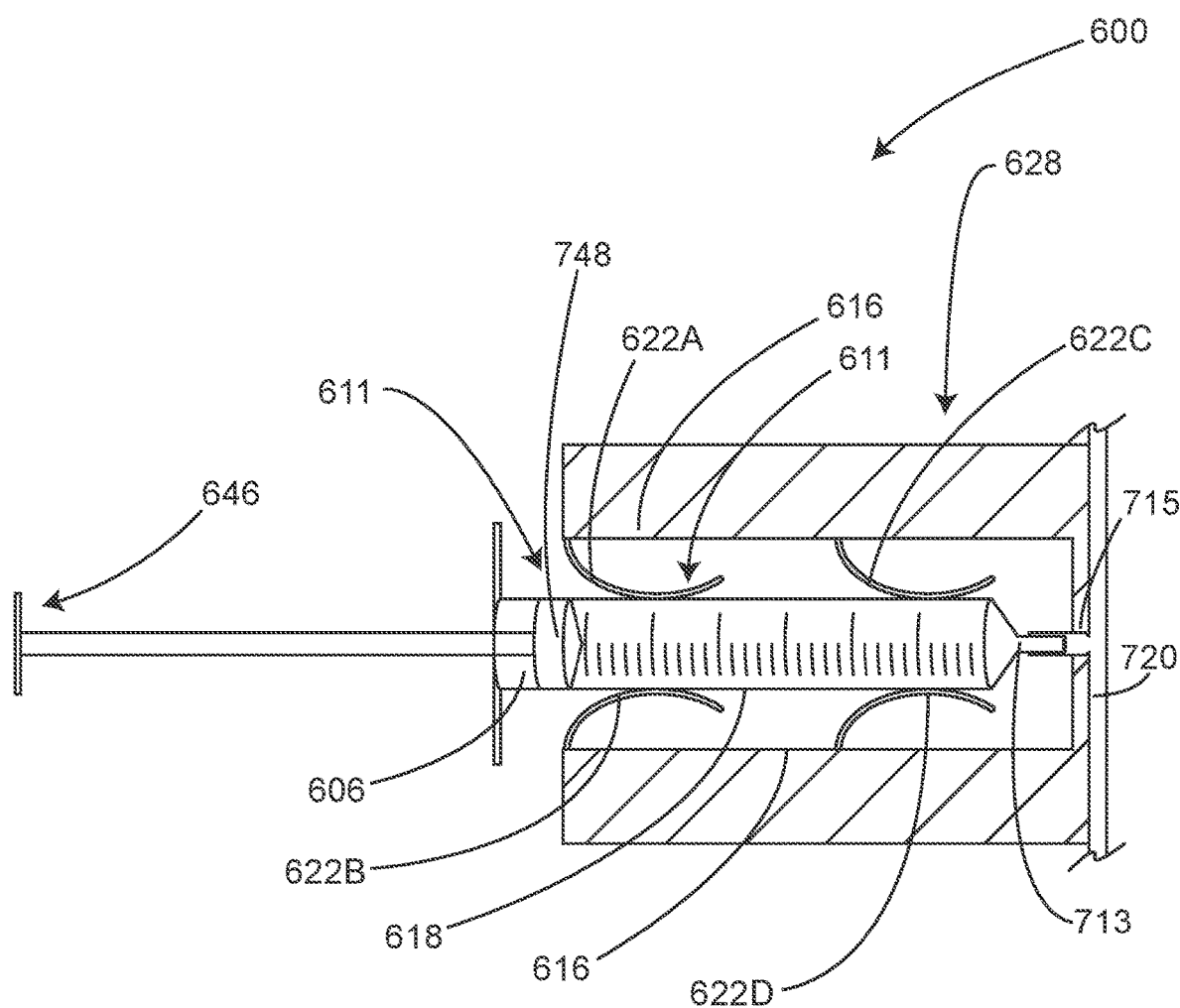
FIG. 7 illustrates a cross-sectional view of the second example of a medication identification and measurement system and the syringe (not shown in cross-section) of FIG. 6, taken along line 7-7, in accordance with at least one example of this disclosure.

FIG. 6 illustrates a portion of a safety and security system 600 including a side view of a second example of a medication identification and measurement system 628 and a syringe 606 that can be used with the safety and security systems 100, 200 of FIGS. 1 and 2, to monitor drug delivery. FIG. 7 illustrates a cross-sectional view of the second example of a medication identification and measurement system 628 and the syringe 606 (not shown in cross-section) of FIG. 6, taken along line 7-7. FIGS. 6 and 7 are described together.

As shown in FIGS. 6 and 7, the injection portal 611 of the medication identification and measurement system 628 may be large enough to accommodate syringes 606 of multiple sizes within the space defined by a real or imaginary injection portal tube 616. In this example, accurately orienting the Luer taper connector 713 to mate with an injection port 715 may be accomplished by one or more orienting members such as one or more spring positioning members 622A-F that engage with the syringe barrel 618 to center it in the injection portal 611. In some examples, there may be two or more rows of spring positioning members 622A-F. For example, spring positioning members 622A, B, E, F may be located near the entrance to the injection portal 611 and spring positioning members 622C, D may be located near the injection port 715 to assure accurate positioning for mating with the Luer taper connector 713. Spring positioning members 622A-F may include not only spring wires or metal or polymer or plastic spring pieces but any flexible material or combination of materials or shapes that can be deformed by the syringe barrel 618 entering the injection portal 611 and retain a memory (e.g., elastically deformable, substantially elastically deformable, resiliently deformable, resilient member) so as to urge the syringe barrel 618 into a centered position within the space defined by a real or imaginary injection portal tube 616.

One objective of the spring positioning members 622A-F can be to "automatically" center and align the Luer taper connector 713 of the syringe 606 with the injection port 715, so that the operator can simply and conveniently push the syringe 606 into the injection portal 611 and no further manual alignment may be needed. The spring positioning members 622A-F can also obviate the need for the operator to touch either the Luer taper connector 713 of the syringe 606 or the injection port 715, thus beneficially preventing accidental infectious contamination by the operators' fingers and gloves.

Figure 8:
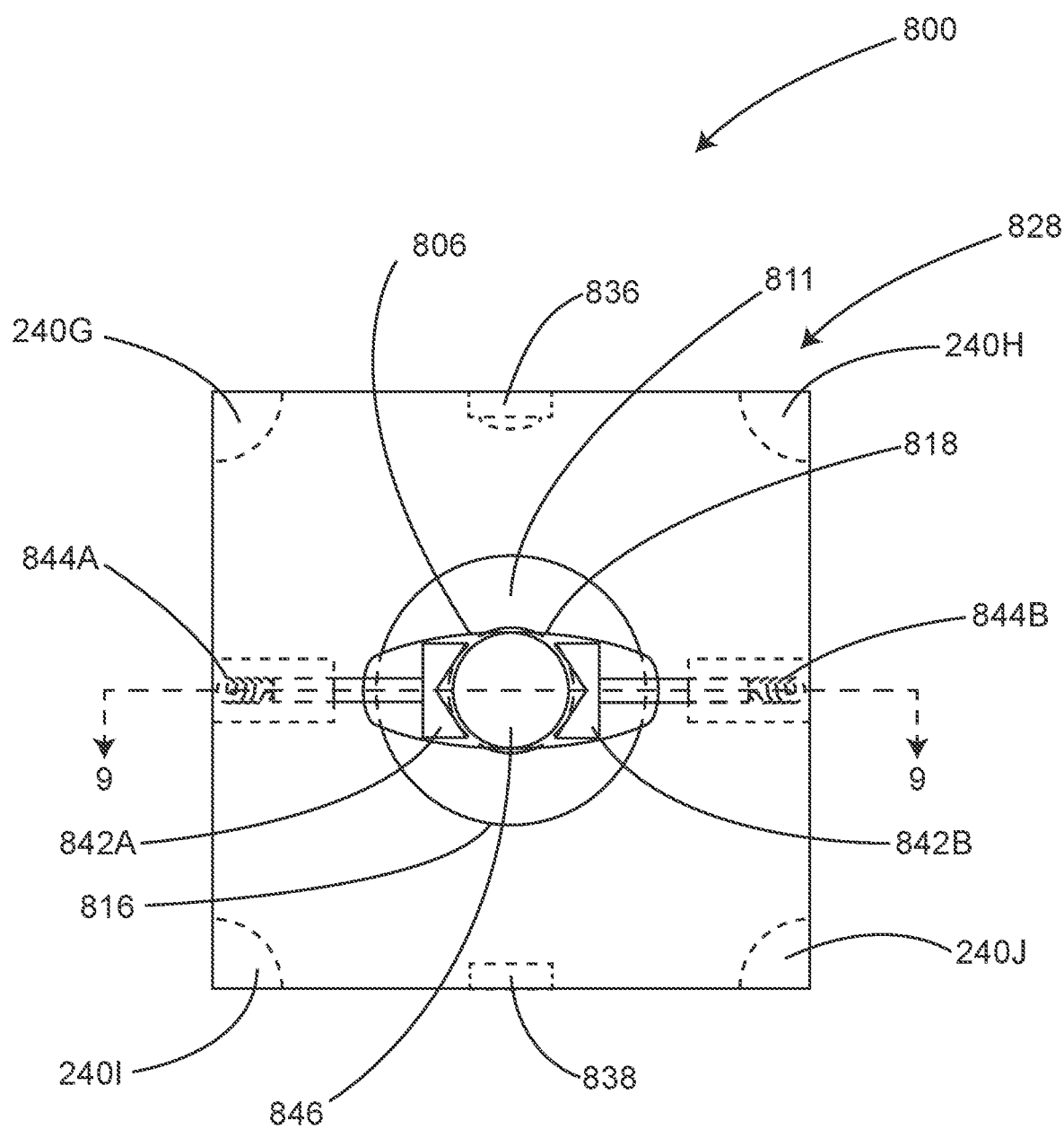
FIG. 8 illustrates a side view of a third example of a medication identification and measurement system and a syringe that can be used with the system of FIGS. 1 and 2, in accordance with at least one example of this disclosure.
Figure 9:
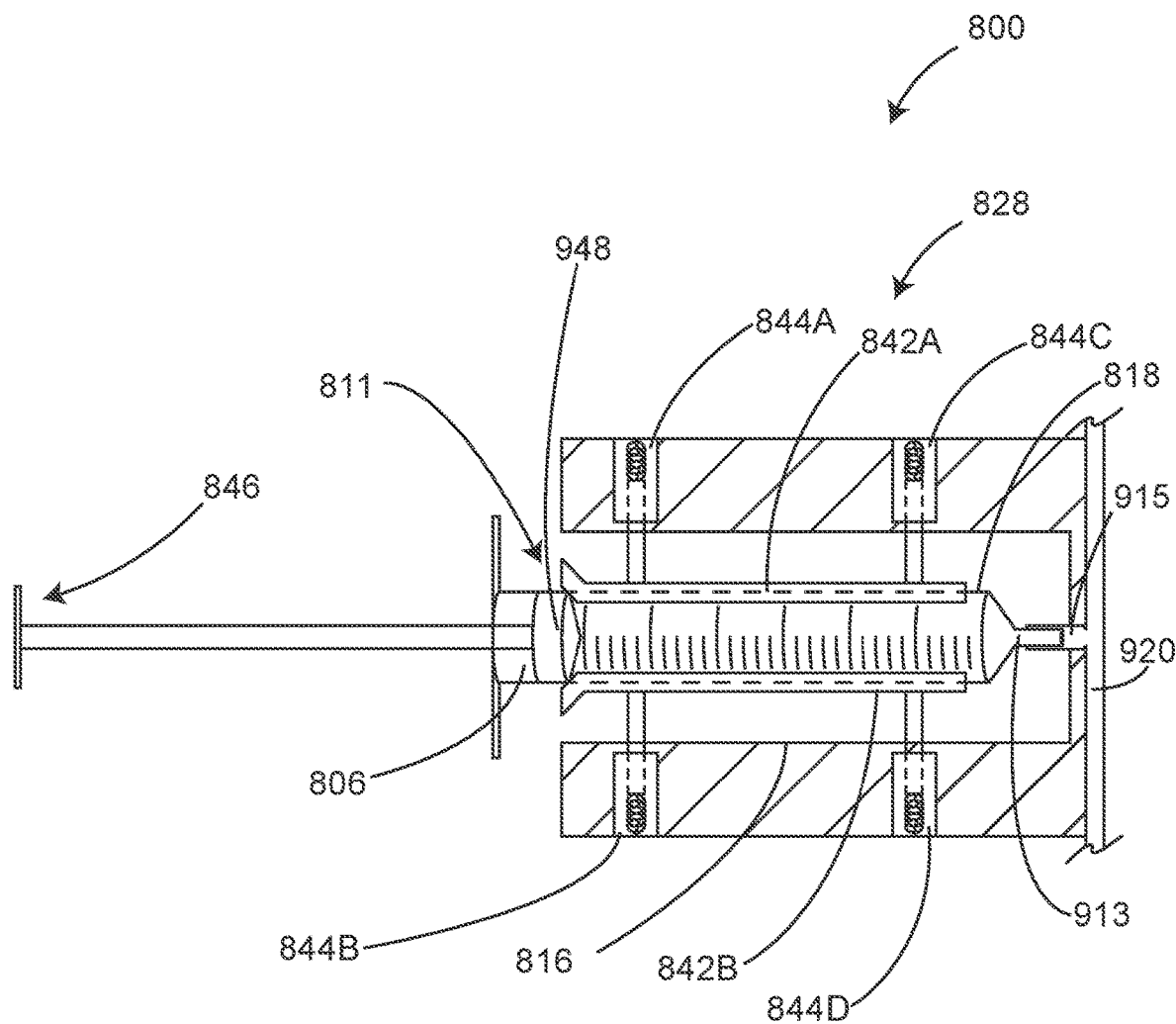
FIG. 9 illustrates a cross-sectional view of the third example of a medication identification and measurement system and the syringe (not shown in cross-section) of FIG. 8, taken along line 9-9, in accordance with at least one example of this disclosure.

FIG. 8 illustrates a portion of a safety and security system 800 including a side view of a third example of a medication identification and measurement system 828 and a syringe 806 that can be used with the safety and security systems 100, 200 of FIGS. 1 and 2. FIG. 9 illustrates a cross-sectional view of the third example of a the medication identification and measurement system 828 and the syringe 806 (not shown in cross-section) of FIG. 8, taken along line 9-9. FIGS. 8 and 9 are described together.

As shown in FIGS. 8 and 9, a syringe barrel 818 may be centered and held in place by one or more orienting members, such as compression positioning members 842A,B. The compression positioning members 842A, B may be urged apart by inserting the syringe barrel 818 there between. Springs 844A-D can compress and create a pressure pushing the compression positioning members 842A,B against syringe barrel 818. The compression positioning members 842A,B shown in FIGS. 8 and 9 are merely illustrative, and many other sizes, shapes, numbers and locations of compression positioning members 842 are anticipated.

Compression positioning members 842A,B may be simple spring 844A-D activated devices (e.g., resilient members) as shown in FIGS. 8 and 9 or may be any mechanism that can expand (e.g., resiliently expand) to accommodate syringe barrels of various sizes and urge the syringe barrel 818 into a centered position within the space defined by a real or imaginary injection portal tube 816. This example shows spring 844A-D activated compression positioning members 842A,B but many other mechanical activation mechanisms are anticipated. The compression positioning members 842A,B can be elastically deformable, substantially elastically deformable, resiliently deformable, include one or more resilient members.

Other examples of positioning members designed to hold an inserted syringe 806 in the center of the injection portal 811 and thus orienting the Luer taper 913 for mating with the injection port 915 are anticipated. Positioning the inserted syringe 806 in the center of the injection portal 811 allows the machine vision to work from a known distance and thus calculations of syringe plunger 948 movement can be very accurate.

In some examples, instead of the positioning members shown in the examples of FIGS. 6-9 holding a syringe centrally, the positioning members 622A-F or 842A,B can be designed to hold an inserted syringe 606, 806 at a known, but off center position in the injection portal 611, 811, such as when the injection port 715, 915 (FIGS. 7 and 9) is positioned off center in the injection portal 611, 811. Any arrangement of at least one positioning member that aligns an inserted syringe at a known position may be provided.

In some examples, and as shown in FIGS. 4, 6 and 8 the medication identification and measurement system 428, 628, 828 of this disclosure may include one or more "machine vision" cameras 436, 636, 836 that input digital images into one or more processors having processing circuitry 157, 257 as shown and described in FIGS. 1,2, that is programed to analyze machine vision images. In some examples, one of the images that the machine vision cameras 436, 636, 836 may "see" is a barcode label 307 on the syringe 406, 606, 806, that has been inserted into the injection portal 411, 611, 811, for identifying the medication in the syringe 406, 606, 806. As previously noted, the barcode label 307 can identify the brand name and/or generic name of the medication in the syringe. In some examples, the barcode label 307 also may identify one or more of the concentration of the medication, the lot number, the expiration date and other information that may be useful for inventory management.

As shown in FIGS. 4, 6 and 8, the safety and security system 400, 600, 800 of this disclosure can include one or more radio frequency identification (RFID) interrogation antennas 438, 638, 838 that input RFID information into a processor, such as processing circuitry 157, 257 as shown and described in FIGS. 1 and 2, that is programed to analyze RFID data. In some examples, the RFID interrogation antennas 438, 638, 838 can interrogate a RFID tag 308 (FIG. 3) attached to the syringe 406, 606, 806, that has been inserted into the injection portal 411, 611, 811, for identifying the medication in the syringe 406, 606, 806. In some examples, short range RFID such as near field (NF) or high frequency (HF) may be advantageous because they may only detect the syringe 406, 606, 806 that is adjacent to or inside the security system for IV medications 400, 600, 800, and not detect the various other medication syringes that may be sitting on the worktable such as 206A-206C in FIG. 2.

As shown in FIGS. 4, 6 and 8 the medication identification and measurement system 428, 628, 828 of this disclosure may include a RFID interrogator 438, 638, 838. In some examples, the RFID interrogator 438, 638, 838 that can include antennas that may be located inside the medication identification and measurement system 428, 628, 828. In some examples, the RFID interrogator antennas 438, 638, 838 may be located external to but proximate the medication identification and measurement system 428, 628, 828. As the syringe 406, 606, 806 is brought into proximity of the medication identification and measurement system, the RFID interrogator 438, 638, 838 can interrogate the RFID tag 308 on the syringe 406, 606, 806, thereby accurately and reliably identifying a medication for IV administration. In some examples, the RFID tag 308 or other marker may include one or more of: the generic and brand name of the drug, the concentration, the lot number, the expiration date, the manufacturer and other important information that may be recorded. In some examples, the generic and brand name of the drug and the concentration of the drug can be displayed in the injection section of a display such as the display 126, 226 (FIGS. 1, 2).

Machine vision is very accurate for measuring the size of an object at a known distance or the distance of an object of known size. However, it cannot do both. Therefore, in some examples it is important to know the exact location of a syringe and thus know the distance from the camera to the syringe in order to accurately calculate the distance of the movement of the plunger within the syringe.

Syringes are available in multiple sizes such as 3 cc, 6 cc and 12 cc, each of which is a different diameter. The machine vision processor must know both the internal diameter of the barrel of the syringe and the distance that the syringe plunger moves down the barrel, in order to calculate the volume of medication injected, unless it has another source of information. The machine vision of this disclosure can measure the diameter of the syringe because in the examples the syringe 406, 606, 806 is held at known distance and in a centered location relative to the machine vision cameras 436, 636, 836. Alternately, the security system for IV medications 400, 600, 800 of this disclosure may be programed to know that the particular hospital uses only Monoject® syringes for example and the internal diameter of each Monoject® syringe size may be pre-programed into the computer. In this case, the machine vision only needs to differentiate 3 cc, 6 cc and 12 cc syringe sizes from each other. The machine vision processor can determine the internal diameter of the barrel of the syringe. In some examples, the syringe size may be included in the information provided by the barcode 307 or RFID 308 (FIG. 3).

In some examples, such as the examples of FIGS. 4-9, the machine vision system, including the machine vision camera 436, 636, 836 and the processor 157, 257 of FIGS. 1 and 2 (e.g., processing circuitry) in electrical communication with the machine vision camera 436, 636, 836, can visually detect and determine other geometry information about the syringe 406, 606, 806 besides the outside diameter, such as determining the inside diameter, or the inner or outer length of the syringe. The medication identification and measurement systems 428, 628, 828 can use the geometry information to determine the size or type of the syringe 406, 606, 806, or can use the geometry information to calculate a volume of the syringe 406, 606, 806.

In some examples, as the syringe 406, 606, 806 is advanced into the injection portal 411, 611, 811, the image of the syringe 406, 606, 806 entering the injection portal 411, 611, 811 is displayed in real time in an injection section 126a, 226a of the display 126, 226 (FIGS. 1 and 2). Therefore, the caregiver can watch the syringe 406, 606, 806 advance and engage with the injection port 515, 715, 915. In some examples, the injection portal tube 416, 616, 816 or the spring positioning members 622A-E or the compression positioning members 842A,B, urge the syringe 606, 806 into position to mate with the injection port 715, 915 but the actual connection can also be observed as it is happening by the caregiver on the display 126, 226. Even though the caregiver is not physically holding the injection port 515, 715, 915 as they typically would, they can watch the engagement of the Luer connector 513, 713, 913 with the injection port 515, 715, 915 on a display 126, 226, the view is essentially identical to the thousands of injections that they have made during their career. In some examples, the actual image of the syringe 406, 606, 806 can be displayed on the display 126, 226, while in other examples the data obtained by the camera 436, 636, 836 can be converted to a representation of the syringe displayed on the display 126, 226.

In some examples, once the syringe 406, 606, 806 is securely connected to the injection port 515, 715, 915, the caregiver pushes on the plunger 446, 646, 846 of the syringe 406, 606, 806, injecting the medication into the injection port 515, 715, 915 and IV tubing 520, 720, 920. The caregiver can visualize the plunger seal 548, 748, 948 move down the syringe barrel 418, 618, 818 and can determine the volume of medication injected by the graduated markings on the syringe 406, 606, 806. Thus, the engagement of the Luer connector 513, 713, 913 with the injection port 515, 715, 915 and the injected volume are observed by the caregiver on the display 126, 226 and the traditional method and routine of injection is minimally altered by implementing the safety and security system 100, 200 including the example medication identification and measurement systems 428, 628, 828.

In some examples, the processing circuitry 157, 257 (FIGS. 1 and 2) or a computer may also simultaneously generate data representing a running total of the volume and dosage of the injected medication and can transmit the generated data to the display 126, 226 to display volume and dosage information on the display 126, 226. In some examples, the processing circuitry 157, 257 or a computer may also generate its own graduated scale and transmit the generated graduated scale information to the display 126, 226 to superimpose the scale on the image of the syringe 406, 606, 806 or next to the image of the syringe 406, 606, 806, for added visual clarity of the injected volume and dose.

Figure 12:
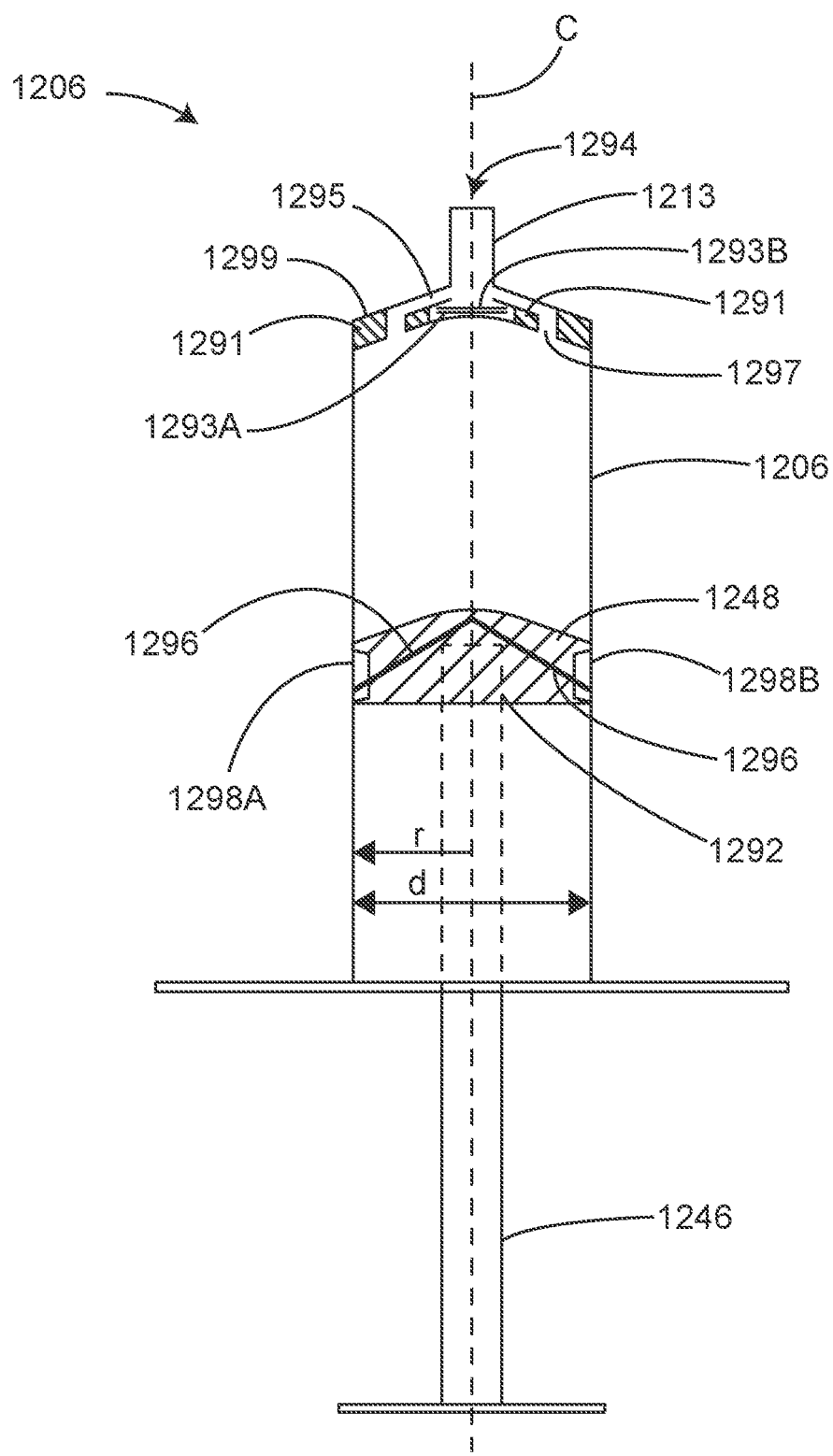
FIG. 12 illustrates a longitudinal cross-sectional view of an example of a medication security syringe that can be used with the system of FIGS. 1 and 2, in accordance with at least one example of this disclosure.

In some examples, the machine vision determination of the injected volume may be calculated by multiplying the internal cross-sectional area of the syringe ($\pi r^2$) by the distance that the syringe plunger moves. The radius of the syringe may be determined in one or more ways. For example, the machine vision function may determine that the syringe approximates a 3 cc or 12 cc syringe and the computer is programed to know that the hospital uses a specific brand of syringes and the internal diameter (radius) of each of these syringe sizes is precisely known. (An example of diameter d, radius r is shown in FIG. 12) Another example may require the machine vision camera to measure the outer diameter of the syringe and then subtract an approximated wall thickness (either measured or known value stored in a memory) from the measured diameter to determine the internal diameter. In another example, the internal diameter of the syringe may be supplied to the processing circuitry 157, 257 or a computer as part of the RFID 308 or barcode 307 information. In another example, the machine vision may determine the inner diameter of the syringe by determining an outer diameter of the plunger as viewed through the transparent or semi-transparent syringe and determine the wall thickness, In yet another example, the machine vision may be able to visibly determine the inner diameter or radius directly through the transparent or semi-transparent syringe. Any other suitable determination, calculation or algorithm may be used to determine the radius, diameter and injected volume.

In some examples, the machine vision determination of the distance that the syringe plunger 446, 646, 846 moves may be by "observing" the movement of the black rubber plunger seal 548, 748, 948 against the visible scale printed on the syringe 406, 606, 806. In this example, the machine vision can be programed to recognize the markings on the syringe 406, 606, 806.

In some examples, the machine vision determination of the distance that the syringe plunger 446, 646, 846 moves may be by observing the movement of the black rubber plunger seal 548, 748, 948 relative to a scale calculated by the processing circuitry 157, 257 (FIGS. 1 and 2). The geometrical calculation of the scale that determines the distance that the syringe plunger 446, 646, 846 moves may be easiest to determine along the widest part of the syringe that corresponds with the center C (FIG. 12) of the syringe 406, 606, 806, which is a known distance from the machine vision camera 436, 636, 836. Alternatively, the computer-constructed scale may be applied to the side of the syringe 406, 606, 806 facing the camera 436, 636, 836, if the radius of the syringe 406, 606, 806 is subtracted from the known distance to the center C (FIG. 12) of the syringe 406, 606, 806 in order to calculate the distance 437 from the machine vision camera 436, 636, 836 to the near side (e.g., 411A) of the syringe 406, 606, 806.

In some examples, the movement of the black rubber plunger seal 548, 748, 948 of the syringe 406, 606, 806 can be clearly identifiable by the machine vision camera 436, 636, 836 and a scale to determine the distance moved by the plunger 446, 646, 846 can either be "visualized" or constructed by the machine vision computer (e.g., processing circuitry). Multiplying the distance that the plunger seal 548, 748, 948 moves by the known or measured internal diameter d (FIG. 12) of the syringe 406, 606, 806 and thus cross-sectional area of the plunger seal 548, 748, 948, allows the processing circuitry 157, 257 or a computer in electrical communication with the processing circuitry 157, 257 to calculate an accurate injected volume. The measured injection volume and dosage may be displayed on the display 126, 226 of the module 101, 201 (FIGS. 1 and 2). Without interfering with or changing the anesthesiologists' normal or traditional medication injection routines, an unobtrusive machine vision camera 436, 636, 836 and computer (e.g., processing circuitry) can "observe" the medication injections and automatically record them in the EMR.

In some examples, the injected volume of medication may be determined by other sensors or methods. For example, the systems described herein can employ (e.g., substitute) other sensors such as a non-visual optical sensor 436A in place of or in addition to the machine vision camera 436, 636, 638 described in FIGS. 4-9. For example, a light source cab shine on one or more light sensitive elements such as photodiodes, and the position of the plunger of the syringe can be roughly determined by the obstruction of the light beam by the plunger. Other fluid measurement methods can have a sensor including adding magnetic material to the syringe plunger and detecting movement of the plunger with a magnetic proximity sensor. Alternatively, fluid flow may be measured with fluid flow meters in the IV fluid stream. These examples are not meant to be an exhaustive list but rather to illustrate that there are alternative technologies to machine vision (e.g., sensors), for noncontact measurement (e.g., sensing) of fluid flow from a syringe that are anticipated in this disclosure.

Securing the injection port 515, 715, 915 within the injection portal 411, 611, 811 prevents the caregiver from touching the injection port 515, 715, 915. Normally caregivers wear gloves to protect themselves from infectious contaminates from the patient and operating room and their gloves are nearly always contaminated. Anything they touch will be contaminated. They typically pick up and hold the IV injection port 515, 715, 915 with one hand while inserting the Luer taper connector 513, 713, 913 of the syringe 406, 606, 806 into the injection port 515, 715, 915. In the process, the injection port 515, 715, 915 is frequently contaminated with pathogenic organisms from their gloves that can enter the patient's blood stream with the next injection, causing serious infections. It is therefore advantageous from the infection prevention point of view, if the Luer connection and injection can be accomplished while never touching the injection port 515, 715, 915.

In some examples as shown in FIGS. 4, 6 and 8 the medication identification and measurement system 428, 628, 828 can include one or more ultraviolet (UV) lights 440A, 440B, 640A-D, 840A-D that shine on the injection port 515, 715, 915. The one or more UV lights can be located inside the module (e.g., 101, FIG. 1) of the medication identification and measurement system 128, 228, 428, 628, 828, keeping the injection portal 411, 611, 811 and the injection port 515, 715, 915 disinfected. In some examples, the UV lights 440A, 440B, 640A-D, 840A-D may preferably be in the UV-C part of the light spectrum. UV-C light has been shown to have superior germicidal powers over other parts of the UV spectrum. The UV lights 440A, 440B, 640A-D, 840A-D may shine continuously or intermittently. By making the injection port 515, 715, 915 untouchable because it is inside the module 101 and radiating the injection port 515, 715, 915 with UV-C light, the injection port 515, 715, 915 should be effectively disinfected between each injection and thereby eliminate injection port 515, 715, 915 contamination as a source of bloodstream infection.

Figure 11:
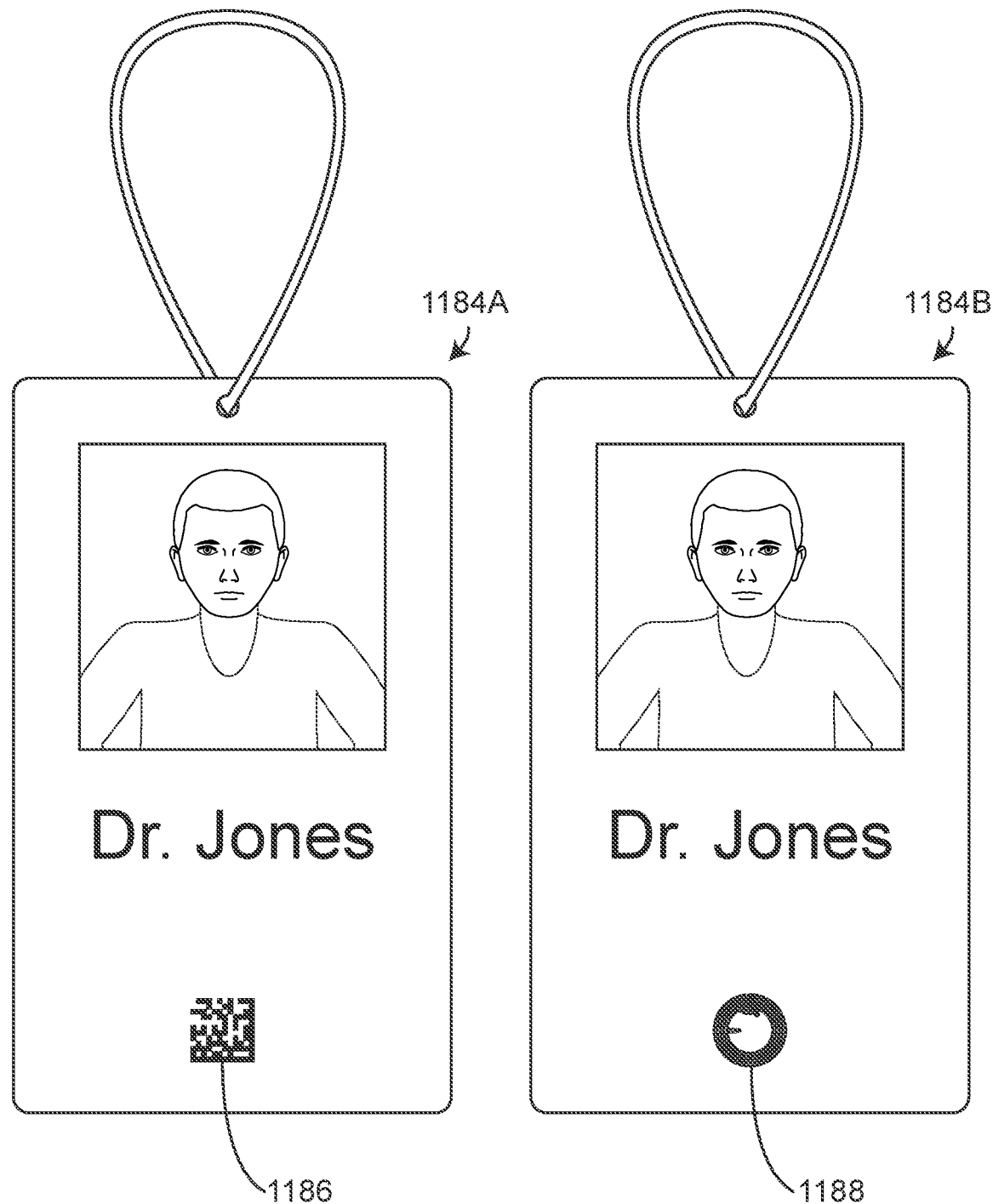
FIG. 11 illustrates a plan view of an example of healthcare provider ID badges that can be used with the system of FIGS. 1 and 2, in accordance with at least one example of this disclosure.

In some examples as shown in FIGS. 1 and 2, the safety and security system 100, 200 may include an external reader, such as barcode reader 180, 280 on the module 101, 201 to read a barcode, QR code or the like for identification. This barcode reader 180, 280 may be used to identify the healthcare provider injecting a medication by reading a barcode or QR code 1186 on the user's ID badge for example (FIG. 11). In some examples as shown in FIGS. 1 and 2, the safety and security system 100, 200 may include an external RFID reader 182, 282 on the module 101, 201. This RFID reader 182, 282 may be used to identify the healthcare provider injecting a medication by reading an RFID tag 1188 on the user's ID badge 1184B for example (FIG. 11). In some examples as shown in FIGS. 4, 6 and 8, the safety and security system 400, 600, 800 may include an internal RFID reader 438, 638, 838 in the module 101, 201. This RFID reader 438, 638, 838 may also be used to identify the healthcare provider injecting a medication by reading an RFID tag on the user's ID badge for example.

It is an important part of the record to know who injected the medication and their identity can be easily verified and documented by the safety and security system 400, 600, 800 using either barcode, QR code or RFID. Other identification technologies are also anticipated.

Figure 10:
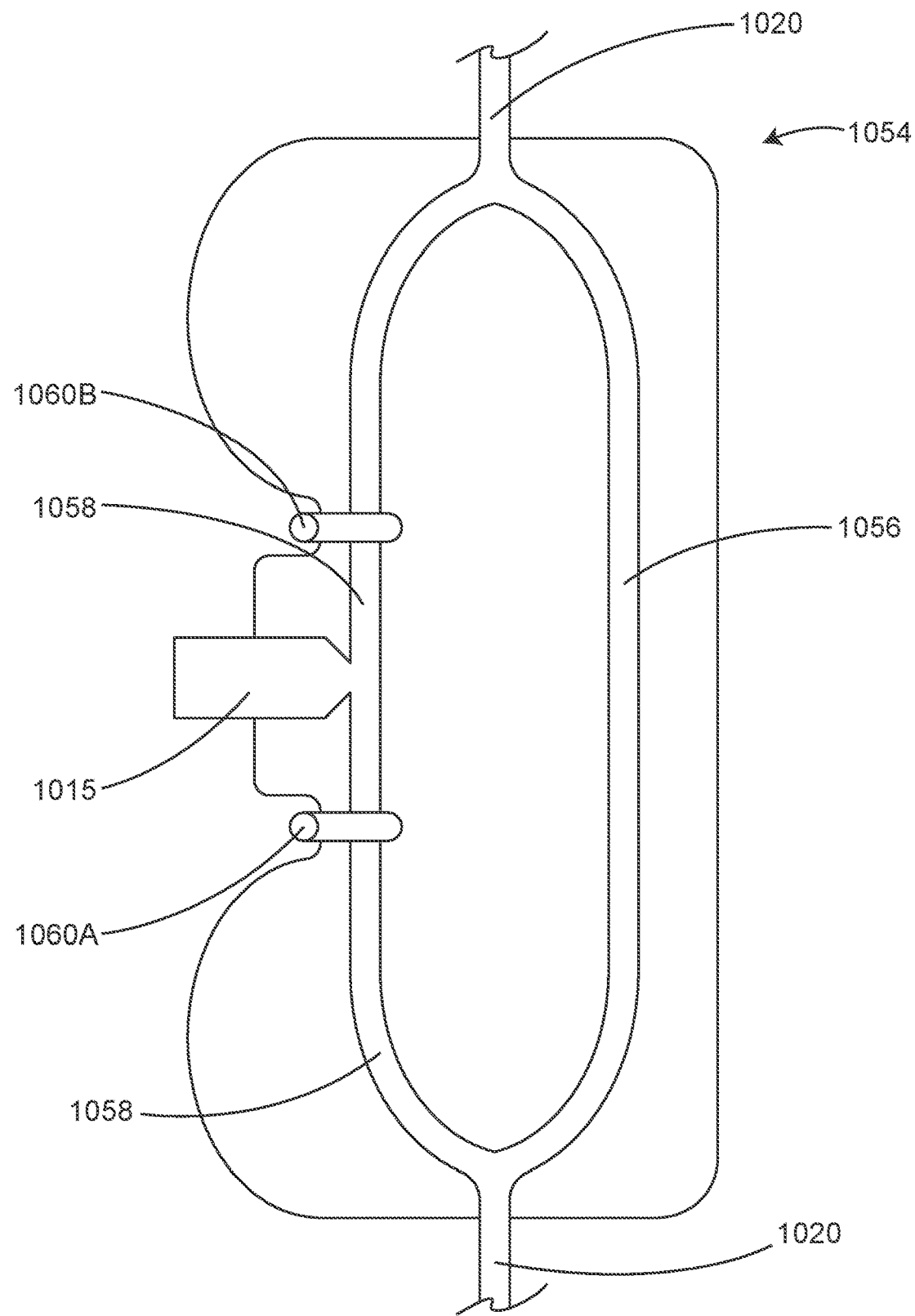
FIG. 10 illustrates an example injection port cassette that can be used with the system of FIGS. 1 and 2, as detailed in FIGS. 5, 7 and 9, in accordance with at least one example of this disclosure.

FIG. 10 illustrates an example injection port cassette 1054 that can be used with the safety and security systems 100, 200 of FIGS. 1 and 2, as detailed in FIGS. 5, 7 and 9. As shown in FIG. 10, the injection port 1015 may be mounted on an injection port cassette 1054 in order to make the attachment to the safety and security system 100, 200, 400, 600, 800 easier and more secure. The injection port cassette 1054 may be a piece of molded polymer or plastic onto which the injection port 1015 and IV tubing 1020 may be attached. The injection port cassette 1054 may be shaped and sized to fit into a slot in the safety and security system 100, 200, 400, 600, 800. When the injection port cassette 1054 is fit into a slot in the safety and security system 100, 200, 400, 600, 800, the injection port 1015 can be positioned substantially in the center of the injection portal 411, 611, 811 for mating with the Luer tapers 513, 713, 913. The injection port cassette 1054 can also be configured to be removed intact from the safety and security system 400, 600, 800 so that the patient can be transferred and the IV tubing 1020 can be moved with the patient and continue to operate normally.

In some examples, and as shown in FIG. 10, the injection port cassette 1054 can include an IV bypass channel 1056 in the IV tubing 1020. The IV bypass channel 1056 can allow the IV fluids to flow unencumbered by the medication injection apparatus. The injection port cassette 1054 can include a medication channel 1058 in the IV tubing 1020 and, the medication channel 1058 may include one or more stop-flow clamps 1060A,B. The one or more stop-flow clamps 1060A,B may be activated by the safety and security system 100, 200, 400, 600, 800 if a medication error is identified. The one or more stop-flow clamps 1060A,B may be powered by one or more electromechanical solenoids that squeeze the IV tubing in the medication channel 1058 flat, obstructing the flow. Other electromechanical flow obstructers are anticipated.

In some situations, such as when administering a drug to a patient allergic to that drug, or administering potent cardiovascular drugs to a patient with normal vital signs, or administering a drug with a likely mistaken identity, the computer, such as processing circuitry 157, 257 (FIGS. 1 and 2) for the safety and security system 100, 200, 400, 600, 800 of this disclosure can automatically activate the stop-flow clamps 1060A,B to compress the medication channel 1058 tubing upstream and/or downstream from the injection port 1015. Compressing the IV tubing both upstream and downstream from the injection port 1015 prevents the injection of any medication into the IV tubing 1020. An alert to the adverse condition of the injection may be displayed on display 126, 226 where the stop-flow condition can be over-ridden by the operator touching a manual override switch on the display 126, 226 or the module 101, 201, if the injection was not erroneous. While the stop-flow can occur in the medication channel 1058, the IV fluid flow can continue normally in the parallel bypass channel 1056.

The stop-flow clamps 1060A,B can allow the processing circuitry 157, 257 (e.g., processor, hardware processing circuitry) of the safety and security system 100, 200, 400, 600, 800 to not only warn the operator of a pending medication error, but physically prevent the injection. Perhaps equally as important is that the stop-flow clamps 1060A,B can be quickly released by the operator touching a manual override switch in the event that the apparent error was in fact a planned event or otherwise desired by the operator.

In some examples, a part of the safety and security system 100, 200, 400, 600, 800 can include the ability for the computer (e.g., machine) to know the patient's medical history, medication orders, vital signs, current medications and other important information about that patient. In some examples, the medication in syringe 306 can be identified by RFID tag 308 (FIG. 3) and is detected by RFID interrogator 438, 638, 838 as the syringe 306 enters injection portal 411, 611, 811. The processing circuitry (e.g., 157, 257) of the safety and security system 100, 200, 400, 600, 800 can cross-reference the proposed injection to the patient's medical history, medication orders, vital signs, current medications and other important information about that patient, providing a safety "over-watch" guarding against medication errors. In some examples, the processing circuitry (e.g., 157, 257) of the safety and security system 100, 200, 400, 600, 800 may include algorithms and/or "artificial intelligence" that can provide alternative medication suggestions based on patient's medical history, medication orders, vital signs, current medications and other important information about that patient.

In some examples, the EMRs that were created by the safety and security system 100, 200, 400, 600, 800 of this disclosure can provide accurate and temporally correlated information about the relationship between any injected medication and the resulting physiologic response. This is uniquely accurate dose-response data. In some examples, the EMRs that were created by the safety and security system 100, 200, 400, 600, 800 for hundreds of thousands or even millions of patients, may be aggregated and analyzed as "big data." The "big data" from these EMRs may be used for a variety of purposes including but not limited to medical research, patient and hospital management and the development of "artificial intelligence" algorithms that can provide alternative medication suggestions. Ongoing "big data" from more and more EMRs can be used to continually improve and refine the "artificial intelligence" algorithms, much like the "artificial intelligence" algorithm development process being used to develop self-driving vehicles. These "artificial intelligence" algorithms can be used to provide automated ("self-driving" or "partially self-driving") anesthesia during surgery or automated medication delivery.

It is well known that scheduled drugs such as Fentanyl and other narcotics are frequently stolen by drug addicted healthcare personnel. The final link in the "chain of custody" between when the drugs are checked out from a vending system such as a pharmacy or Pixis medication dispenser, and when the drugs are injected into the patient is missing. The final link in the "chain of custody" between when the drugs are checked out from the pharmacy and when the drugs are injected into the patient is totally dependent on the personal integrity of the healthcare provider. It is also impractical for each narcotic injection to be personally monitored by a second healthcare provider. Without a complete "chain of custody," even a second provider monitoring the injection may not be adequate to prevent medication pilferage. Addicted healthcare providers frequently substitute saline for a clear medication such as the narcotic Fentanyl—injecting the saline and keeping the Fentanyl for themselves. Addicted healthcare providers have been known to successfully steal their patient's narcotics for years before being caught.

In some examples, the safety and security system 100, 200, 400, 600, 800 of this disclosure provides a "chain of custody" between when drugs are checked out from the pharmacy or Pixis medication dispenser, and when the drugs are injected into the patient. The "chain of custody" provides security especially for scheduled drugs such as narcotics. The "chain of custody" provided by the safety and security system 100, 200, 400, 600, 800 makes it nearly impossible to steal the patient's narcotics. The added security provided by the safety and security system 100, 200, 400, 600, 800 significantly increases the chances of getting caught, thus creating a disincentive for addicted healthcare providers stealing their patient's drugs.

FIG. 11 illustrates a plan view of an example of healthcare provider ID badges 1184A and 1184B that can be used with the system of FIGS. 1 and 2, in accordance with at least one example. In some examples, the "chain of custody" may begin by electronically identifying the healthcare provider as the drugs are checked out from the pharmacy or Pixis medication dispenser. In some examples and as shown in FIG. 11, each provider can have a personalized RFID tag 1186, attached to their hospital ID badge 1184A. In some examples each provider can have a personalized barcode 1188, attached to their hospital ID badge 1184B for example. When the drugs are checked out, the personalized RFID tag 1186 may be read by an RFID interrogator or the personalized barcode 1188 read by a barcode reader in the pharmacy and the ID of the provider checking the drugs out may be noted in the hospital's computer and/or the processing circuitry 157, 257 (FIGS. 1 and 2) for the safety and security system 100, 200, 400, 600, 800 (FIGS. 1, 2, 4, 6 and 8). The specific RFID 308 or barcode 307 (FIG. 3) identification of the injectable drug may also be recorded before the drug leaves the pharmacy and that information may be transmitted to the processing circuitry 157, 257 of the safety and security system 100, 200, 400, 600, 800 of this disclosure. In some examples, instead of an RFID tag 1186 and RFID reader, other provider identification information and sensors for identifying the provider can be used, such provider identification information may include: a barcode, a QR code with the sensor being able to read such codes. In other examples, the sensor can include a retinal scanner, fingerprint reader or a facial recognition scanner that identifies the provider by personably identifiable information (e.g., provider identification information) may be used.

In some examples, non-refillable preloaded syringes may be used to prevent pilferage of the drugs between leaving the pharmacy and arriving at the patient's bedside. It is a well-known practice for providers to steal drugs by pocketing the bottle, vial or ampule and then filling the syringe with saline for injection into the patient. Pre-loaded syringes remove the opportunity for the provider to pilfer drugs while loading a syringe from a bottle, vial or ampule. A non-refillable syringe makes it difficult or even impossible to discharge the narcotics from a preloaded syringe into a second syringe and then refill the discharged syringe with saline or other clear fluids.

In some examples, when the provider arrives at the patient's bedside, the provider may be identified by their ID badge 1184 A,B. In some examples, an ID badge 1184A that has an RFID tag 1186 may be read by RFID reader 182, 282 (FIGS. 1 and 2) that can be located on the safety and security system 100, 200, 400, 600, 800 or by RFID reader 438, 638, 838 (FIGS. 4, 6 and 8) located inside the safety and security system 100, 200, 400, 600, 800 (FIGS. 1, 2, 4, 6 and 8). In some examples, an ID badge 1184B that has a barcode 1188 may be read by barcode reader 180, 280 that can be located on the safety and security system 100, 200, 400, 600, 800. In some examples, a retinal scanner may be located on or near module 101, 201 in order to positively identify the provider by their retinal vasculature. Other scanners including but not limited to facial recognition scanning are also anticipated in order to positively identify the provider doing the injection in order to automatically document this information to an EMR or other record.

In some examples, the provider's photograph may be taken by camera 190, 290 (FIGS. 1 and 2) for further identification before allowing the injection of scheduled drugs. In some examples, the camera 190, 290 may be triggered, such as by processor 157, 257 (FIGS. 1 and 2), when a syringe e.g., 306B filled with a scheduled drug such as a narcotic is identified as it enters the injection portal 411, 611, 811 and the RFID interrogator 438, 638, 838 interrogates the RFID tag 308 (FIG. 3) or the machine vision camera 436, 636, 836 reads the barcode 307 (FIG. 3) on the syringe 306A. Non-scheduled medications may not need the added security of a photograph.

In some examples, when the syringe, such as 406, 606, 806, filled with a scheduled drug such as a narcotic enters the injection portal 411, 611, 811, the RFID interrogator 438, 638, 838 interrogates the RFID tag 308 or the machine vision camera 436, 636, 836 reads the barcode 307 on the syringe 306A, 306B. At that point, the safety and security system 100, 200, 400, 600, 800 of this disclosure can have documented, such as by recording to memory one or more of: 1.) the specific drug syringe that was checked out of the pharmacy and is now inside the injection portal 411, 611, 811; 2.) the ID of the provider injecting the drug; 3.) the ID of the provider who checked the drug out of the pharmacy 4.) the patient who is being injected and 5) the time of the injection. The processing circuitry 157, 257 can include or be electrically connected to a timer and a memory to facilitate recording the time.

In some examples, the machine vision camera 436, 636, 836 of the safety and security system 100, 200, 400, 600, 800 "watches" the injection occur and documents that it occurred. When the injection has occurred, the "chain of custody" is complete for that dose of the scheduled drug. If all of the drug in the syringe is not injected, the safety and security system 100, 200, 400, 600, 800 can document the non-injected drug. The remaining non-injected drug may be "closed out" in the system by being administered to the patient in a second or third injection or by being properly disposed of and manually documented.

In some examples, in order for the safety and security system 100, 200, 400, 600, 800 to assure a "chain of custody" for a given drug, the drug may come from the pharmacy in a pre-loaded syringe that may be tamper-proof and non-refillable. There are many ways that narcotics such as Fentanyl have been pilfered by healthcare personnel. First, if the drug is delivered in a vial, ampule or bottle, it may not be transferred into the injection syringe by the provider. The syringe may be refilled with another fluid such as saline instead and the narcotic may be put in the provider's pocket. Therefore, in some examples, prefilled syringes may be desirable to assure the last link in the "chain of custody" between the pharmacy and the patient is complete.

Another well-known opportunity for stealing drugs in the healthcare setting is from a syringe that has been filled with a drug such as a narcotic. Very simply, some or all of the drug in the syringe can be discharged into another syringe or container and then the first syringe can be refilled with saline looking exactly like it did before the discharge. To prevent this method of drug pilferage, the syringes used for narcotics should be non-refillable. Filling a standard syringe is normally accomplished by pulling on the plunger that is attached to the plunger seal—a rubber gasket mounted on the end of the plunger. The distal end of the plunger is knob-shaped and it fits into a pocket-like receptacle in the plunger seal that captures the knob of the plunger and pulls the plunger seal along when the plunger is pulled from the syringe.

FIG. 12 illustrates a longitudinal cross-sectional view of an example of a medication security syringe that can be used with the system of FIGS. 1 and 2. In some examples, and as shown in FIG. 12, the normal method of filling a syringe 1206 can be prevented by replacing the knob-shaped distal end of the traditional plungers (e.g., 446, 646, 846) with a tubular-shaped distal end 1292 as of plunger 1246. If the plunger 1246 is retracted from the syringe 1206, the relatively smooth sides of the distal end 1292 of the plunger 1246 disengage easily from the plunger seal 1248, preventing the plunger seal 1248 from creating the vacuum necessary to refill the syringe 1206.

In some examples, an enterprising drug thief could overcome the fact that relatively smooth sides of the distal end 1292 of the plunger 1246 disengage easily from the plunger seal 1248, by forcing fluid into the open end 1294 of the Luer taper 1213. Fluid such as saline under pressure would fill the syringe from the Luer taper end 1213 and force the plunger seal 1248 rearward as the syringe 1206 fills with fluid. In some examples, a spring wire barb 1296 or other metal protrusion forming a barb may be molded into or attached to rubber plunger seal 1248. In some examples, the tips 1298A,B of spring wire barbs 1296 may be angled rearward away from the Luer taper 1213 and compressed inward by the walls of the barrel of syringe 1206. The rearward angle of spring wire barbs 1296 allow the rubber plunger seal 1248 with its attached or imbedded spring wire barbs 1296 to be pushed forward in a normal fashion by plunger 1246, discharging the contents of the syringe 1206.

In some examples, if fluid such as saline under pressure was attempted to be forced into the syringe 1206 from the Luer taper 1213 end forcing the plunger seal 1248 rearward, the tips 1298A,B of spring wire barbs 1296 can gouge into the soft polymer or plastic (e.g., polyethylene or polypropylene) of the walls of the barrel of syringe 1206 and prevent a rearward movement of plunger seal 1248. Therefore, when the syringe 1206 has discharged it contents, it cannot be reloaded or refilled. The spring wire barbs 1296 as shown in FIG. 12 are an example of using a barb or ratchet effect to allow movement of plunger seal 1248 in one direction and prevent movement of plunger seal 1248 in the other direction. Other barb or ratchet mechanisms that accomplish this same effect are anticipated.

In some examples, an enterprising drug thief could overcome the fact the syringe 1206 of this disclosure cannot be reloaded or refilled, by removing the contents of the syringe 1206 without depressing the plunger 1246. This can be accomplished in prior art syringes by inserting a hypodermic needle attached to a second syringe, through the opening in the Luer taper 1213 connector and sucking out the contents of syringe 1206. A third syringe filled with saline can then be used to refill syringe 1206 by inserting a hypodermic needle through the opening in the Luer taper 1213 connector and injecting the saline. Therefore, in some examples, it may be advantageous to make the syringe tamper-proof by adding a mechanical barrier on either end of the Luer taper connector 1213 that physically prevents a hypodermic needle from entering syringe 1206.

In some examples, as shown in FIG. 12, a mechanical barrier may be added in the form of needle blocking insert 1291. In an example, the needle blocking insert 1291 may be a piece of molded polymer, plastic or rubber that can be inserted into the barrel of syringe 1206 and pushed down to the closed end. The needle blocking insert 1291 can include a small metal plate 1293 that is positioned directly in front of the opening in the Luer taper connector 1213 in order to prevent a hypodermic needle that may be inserted into the open end 1294 of the Luer taper 1213 connector from entering the barrel of syringe 1206. Depending on the specifics of the design, without a metal plate 1293, a sharp hypodermic needle may be able to be pushed through the polymer, plastic or rubber needle blocking insert 1291 and into the barrel of syringe 1206. The piece of metal 1293 can be retained in a recess 1293A in the needle blocking insert 1291. Although the needle blocking insert 1291 is described as including metal plate 1293, any suitable needle blocking insert that prevents a needle from being inserted into the open end of the Luer taper 1213 can be provided within the scope of this disclosure.

In some examples, as shown in FIG. 12, the needle blocking insert 1291 may include transverse fluid channels 1295 and/or longitudinal fluid channels 1297. The transverse and or longitudinal fluid channels 1295, 1297 may be molded into needle blocking insert 1291 allowing the fluid in syringe 1206 to flow through needle blocking insert 1291 during a normal injection but preventing needle penetration, such as by a drug thief. In some examples, the needle blocking insert 1291 may be coupled by attachment 1299 to syringe 1206 in order to prevent dislodgement. The attachment 1299 between the needle blocking insert 1291 and the barrel of syringe 1206 may be a heat bond, an ultrasonic bond, and RF bond, an adhesive bond or other mechanical attachment such as a pressure fit.

Figure 13:
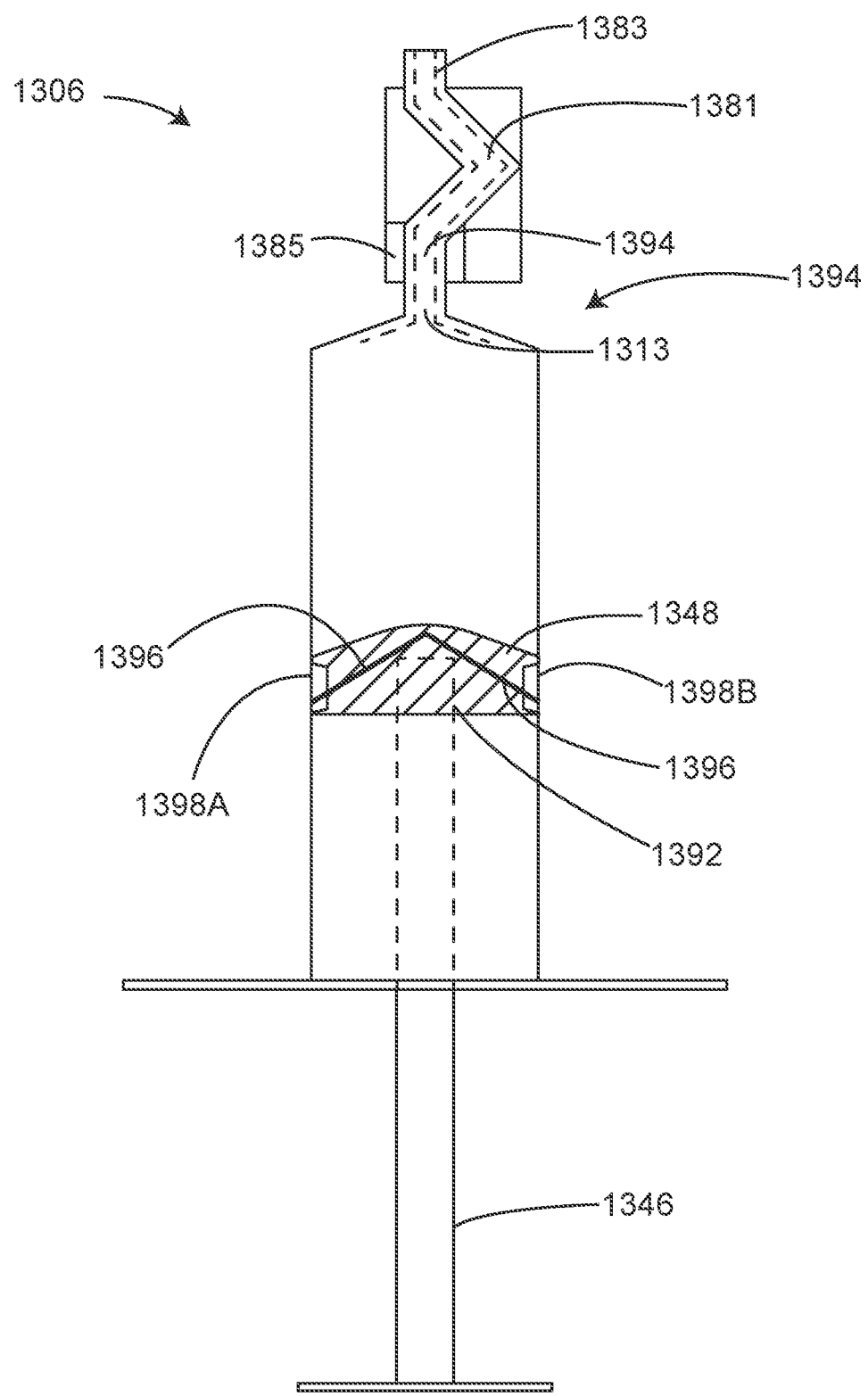
FIG. 13 illustrates a longitudinal cross-sectional view of an example of a medication security syringe that can be used with the system of FIGS. 1 and 2, in accordance with at least one example of this disclosure.

FIG. 13 illustrates a longitudinal cross-sectional view of an example of a medication security syringe 1306 that can be used with the system 100, 200 of FIGS. 1 and 2. In some examples, as shown in FIG. 13, a hypodermic needle may be prevented from entering the open end 1394 of the Luer taper 1313 connector by adding a serpentine or zig-zag fluid channel 1381 to the open end 1394 of the Luer taper 1313 connector. In some examples, the serpentine or zig-zag fluid channel 1381 may be made of molded polymer or plastic that creates an extended Luer taper connector 1383. The molded serpentine or zig-zag fluid channel 1381 may include a hub 1385 that mates with Luer taper 1313 connector and is connected to Luer taper 1313 connector by a heat bond, an ultrasonic bond, and RF bond or an adhesive bond. The serpentine or zig-zag fluid channel 1381 prevents a stiff hypodermic needle or even a flexible catheter from navigating the sharp corners of the fluid channel 1381. In some examples, the molded components described herein can be alternately formed, such as by 3D printing.

By preventing the movement of plunger seal 1248 after the syringe has been discharged and preventing the insertion of a hypodermic needle through the open end 1294, 1394 of the Luer taper 1213, 1313 connector in order to suck out the drug and then reload the syringe 1206, 1306 with saline, the syringes 1206, 1306 of FIGS. 12 and 13 are resistant to undetected drug theft.

In some examples as shown in FIGS. 1 and 2, the safety and security system 100, 200 of this disclosure may include a remote monitor with display 187, 287. The remote monitor may include a wired or wireless connection to the safety and security system 100, 200 and may display some or all of the information shown on the electronic record display 126, 226, or other information generated by the safety and security system 100. For example, the processing circuitry 157, 257 can be in electrical communication with the remote display 187, 287 and the processing circuitry 157, 257 can send instructions to the remote display 187, 287 to display the generated information.

The remote monitor may be in the next room or miles away. The remote monitor may allow remote supervision of healthcare delivery. For example, anesthesiologists frequently supervise up to four surgical anesthetics at once, each being delivered by a nurse anesthetist. In this case, the anesthesiologist carrying a wireless remote monitor 187, 287 can have real-time data on each case under their supervision. Similarly, a nurse anesthetist working in a rural hospital may be supervised by an anesthesiologist who is 50 miles away.

In some examples, the remote monitor with display 187, 287 can create a record for billing. For example, when an anesthesiologist is supervising multiple anesthetics at once, the payers may dispute the involvement in each case and refuse to pay. The remote monitor with display 187, 287 may include an RFID reader that documents the close proximity of an RFID tag on the anesthesiologist's ID badge. Any other type of proximity sensor may be used in place of the RFID tag, including but not limited to GPS location sensing. Documenting that the anesthesiologist was carrying the remote monitor with display 187, 287 throughout the time of the surgery is very good evidence that the anesthesiologist was actively participating in the care of the patient.

In some examples, the remote monitor with display 187, 287 allows long-distance medical consultation. For example, an expert at the Mayo Clinic could consult with a physician halfway around the world in Dubai, responding to real-time patient data displayed on the remote monitor with display 187, 287.

Figure 14:
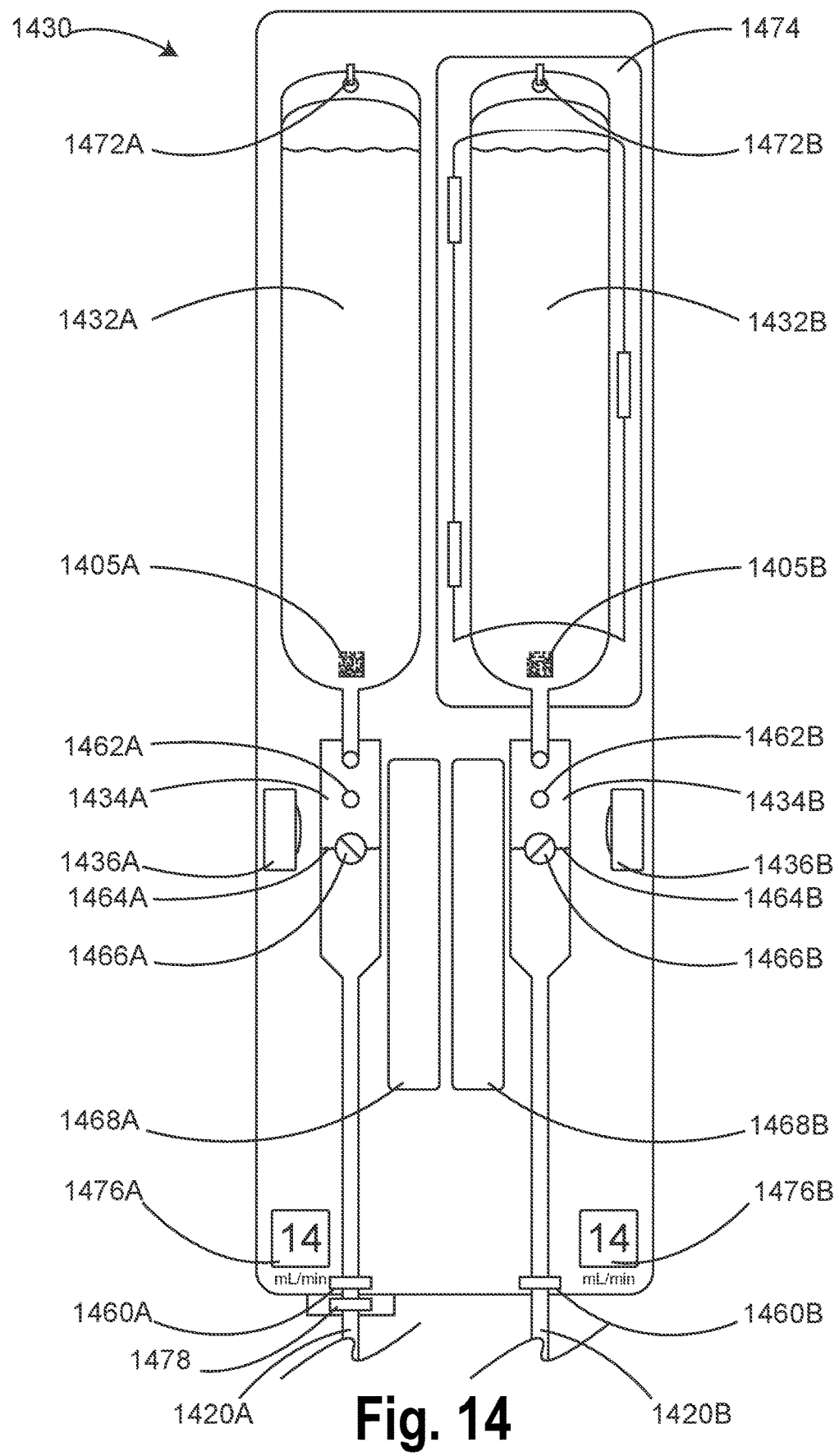
FIG. 14 illustrates a side view of an example IV fluid identification and measurement system that can be used with the systems of FIGS. 1 and 2, and injection port cassette of FIG. 10, in accordance with at least one example of this disclosure.

FIG. 14 illustrates a side view of an example IV fluid identification and measurement system 1430 that can be used with the systems of FIG. 1-9, and the injection port cassette of FIG. 10. Some aspects of FIGS. 1-10 and 14 are described together, however, the examples are merely illustrative and the features can be used in any suitable combination. In some examples, the safety and security system 100, 200 of this disclosure includes a system for automatically measuring and recording the administration of IV fluids. To accomplish this, as shown in FIGS. 1, 2 and 14, the safety and security system 100, 200 can include an IV fluid identification and measurement system 130, 230, 1430. In some examples, the IV fluid identification and measurement system 130, 230, 1430 can be mounted onto module 101.

Alternately, the IV fluid identification and measurement system 130, 230, 1430 may be mounted to an IV pole 105 or racking system independent from the module 101. The system for automatically measuring and recording the administration of IV fluids is not limited to use in anesthesia or in the operating room, but has applicability for use throughout the hospital and other health care settings, including but not limited to the ICU, ER, wards, rehabilitation centers and long term care settings. In some examples, aspects of the IV fluid identification measurement system 130, 230, 1430 can be provided alone or together with other features of the safety and security system 100, 200 including the medication identification and measurement system 128, 228.

In some examples, the IV fluid identification and measurement system 130, 230, 1430 may be configured to accommodate one or more bags of IV fluid 132, 232A,B and 1432A,B. Each bag of IV fluid can include a drip chamber 134, 234A,B and 1434A,B and IV tubing 120, 220A,B and 1420A,B. IV flow rates may be controlled with the traditional manually operated roller clamp that variably pinches the IV tubing 120, 220A,B and 1420A,B to control or even stop the flow of IV fluids. In some examples, IV flow rates may be controlled with the automatically operated electromechanical flow rate clamps 1478 that variably pinch the IV tubing 1420A to control or even stop the flow of IV fluids. The automatically operated electromechanical flow rate clamps 1478 may be controlled by the processing circuitry 157, 257, such as an electronic anesthetic record computer in module 101 or by any other suitable processor including hardware processing circuitry that is in electrical communication with the IV fluid identification and measurement system 130, 230, 1430 and/or is located within the IV fluid identification and measurement system 130, 230, 1430.

In some examples, the IV fluid identification and measurement system 130, 230, 1430 is configured to automatically measure and record the administration of IV medications and fluids. The system 130, 230 can include one or more of a barcode reader and an RFID interrogator (such as 1436A,B) for accurately and automatically identifying a fluid for IV administration. Because of the close proximity to the adjacent bags, barcode identification may be preferable in order to prevent an RFID interrogator from reading the RFID tag on a neighboring bag. In some examples, as shown in FIG. 14, one or more barcode labels 1405A,B may be applied to the IV bags 1432A,B in a location where they can be read by a sensor such as a barcode reader or machine vision camera 1436A,B, or another machine vision camera located in a suitable position to read the barcode. In some examples, a dedicated barcode reader or a machine vision camera may be positioned adjacent the barcode label 1405A,B location, specifically for reading the barcode label 1405A,B.

In some examples, the drip chamber 234A,B and 1434A,B of the IV set can be positioned adjacent the one or more machine vision cameras 1436A,B. In some examples, a standard background 1468A,B may be positioned on the opposite side of the drip chamber 1434A,B from the machine vision cameras 1436A,B. The standard background 1468A,B may be a plain background or may be an advantageous color, pattern, color design or illumination that highlights each of the falling drops, for easier identification by the processing circuitry 157, 257 (e.g., 1502, FIG. 15). The machine vision software including instructions can be stored on one or more machine-readable mediums (such as 1522 in FIG. 15) that when implemented on hardware processing circuitry (including but not limited to processing circuitry 157, 257) or in electrical communication with the system, can perform the functions described herein. An example of such electrical connection is shown by the connection of processor 1502 with mass storage 1516 in FIG. 15.

In some examples, the processing circuitry 157, 257, 1502 can be configured to look for a fluid meniscus 1464A,B in the drip chamber 1434A,B. In this case "seeing" a fluid meniscus 1464A,B indicates that there is fluid in the drip chamber 1434A,B and therefore the IV bag 1432A,B is not empty, and air is not inadvertently entering the IV tubing 1420A, 1420B.

In some examples, if the IV fluid identification and measurement system 130, 230, 1430 fails to "see" a fluid meniscus 1464A,B meaning that the drip chamber 1434A,B is empty and thus the IV bag 1432A,B is empty, stop-flow clamps 1460A,B can be automatically activated. For example, processing circuitry 157, 257 can send an instruction to activate the stop-flow clamps 1460A,B to compress the IV tubing 1420A,B in order to prevent air from entering the IV tubing 1420A,B. In some examples, the empty IV bag 1432A,B condition detected by the processing circuitry 157, 257 can cause an alert to be displayed to the caregiver on the anesthetic record display 226, such as by sending an instruction to the display.

The combination of the machine vision camera 1436A,B in electrical communication with processing circuitry (e.g., 157, 257, FIGS. 1 and 2) that executes instructions stored on a machine readable medium can count the number of drops of fluid per unit of time in a drip chamber 1434A,B to calculate or to estimate the flow rate of an IV. The size of the drip chamber 1434A,B inlet orifice determines the volume of liquid in each drop. The inlet orifices of standard drip chambers are sized to create drops sizes that result in 10, 12, 15, 20, 45 and 60 drops per ml. Given a particular drop volume (size), 10 drops per ml for example, the system 130, 230, 1430 (e.g., via sensors, processing circuitry and machine readable medium) can count the number of drops falling in a known period of time and use that data to calculate or to estimate the flow rate. If these estimates were attempted by a human, they may be less accurate at higher flow rates (higher drop counts) because the drops are so fast, it can be difficult to count the drops. Eventually, at even higher flow rates the individual drops become a solid stream of fluid and the flow rate cannot be visually estimated.

In some examples, the IV fluid identification and measurement system 130, 230, 1430 is configured to look for falling drops of fluid 1462A,B within the drip chamber 1434A,B. When drops 1462A,B have been identified, the machine vision system (e.g., machine vision camera 1436A or 1436B operably coupled to processing circuitry 157, 257) may first measure the diameter of the drop 1462A,B to determine which of the standard drop sizes or volumes it is counting. Most hospitals standardize on several infusion set sizes, 10, 20 and 60 drops per cc for example. Therefore, when these limited choices of infusion set brands and sizes have been programed into the computer, the machine vision system only needs to differentiate between these choices, which is much easier than accurately measuring the diameter of the drops. Unlike the human eye, the machine vision can accurately count the falling drops even at high flow rates to calculate an IV fluid flow rate.

In some examples, the machine vision system, including the machine vision cameras 1436A,B and instructions 1524 (e.g., software) stored on a machine readable medium 1522 and implemented by hardware processing circuitry 157, 257 does not "see" falling drops 1462A,B. In this situation, either the fluid is flowing in a steady stream that is not identifiable or the fluid has stopped flowing. In some examples, these two opposite conditions can be differentiated by inserting a floating object 1466A,B (hereinafter, "float") into the drip chambers 1434A,B. In some examples, the float 1466A,B may be a ball-shaped float 1466A,B. In some examples, the float may be patterned or multi-colored to more easily identify movement or spinning of the float. In some examples, if the machine vision system cannot identify falling drops 1462A,B, it then looks to the float 1466A,B for additional information. If the float 1466A,B is not moving or spinning, the fluid flow has stopped. If the float 1466A,B is moving or spinning and drops cannot be identified, the fluid is flowing in a steady stream and the flow rate cannot be measured by machine vision. In this situation, the system can determine fluid flow using an alternate method.

In some examples, the IV fluid identification and measurement system 130, 230, 1430 may be configured to accommodate one or more bags of IV fluid 132, 232A,B, 1432A,B and each of these IV bags may be hanging from an electronic IV scale 1472A,B (e.g., a weight, a physical characteristic sensor). The electronic IV scale 1472A can measure the combined weight of the IV bag and fluid 1432A, the drip chamber 1434A and the IV tubing 1420A. The electronic IV scale 1472B can measure the weight or combined weight of one or more of the IV bag and fluid 1432B, the drip chamber 1434B, the IV tubing 1420B and a pressure infuser 1474. In both of these examples, the electronic IV scale 1472A,B can accurately measure the change in combined weight that occurs due to the drainage of the IV fluid from the IV bag 1432A,B. The change in weight per unit time can be converted to flow rates by processing circuitry 157, 257 in electrical communication with the electronic IV scale 1472A, 1472B, for example, by the processing circuitry 157, 257, 1502 and displayed on the electronic record display 126, 226.

In some examples, the calculated flow rates for each IV bag 1432A,B may also be displayed on one or more digital flow-rate displays 1476A,B mounted on the IV fluid identification and measurement system 1430. The digital flow-rate displays 1476A,B may be small LED or LCD displays that conveniently tell the operator the flow rate while they are manually adjusting the flow rate near the IV bags 1432A,B and drip chambers 1434A,B. The digital flow-rate displays 1476A,B are particularly convenient when the IV fluid identification and measurement system 130, 1430 is a free standing entity mounted on an IV pole 105 for example while being used on the ward or ICU.

In some examples, when the falling drops 1462A,B cannot be detected and yet the floats 1466A,B are moving or spinning, the fluid is determined to be flowing in a steady stream and the flow rate cannot be measured by machine vision. In this case the electronic record computer may automatically query the change in weight per unit time as measured by the electronic IV scale 1472A,B to determine the IV flow rate. At high flow rates, the change in weight per unit time as measured by the electronic IV scale 1472A, B will most likely be more accurate than counting drops, in determining the IV flow rate.

The IV flow rate as determined by the change in weight per unit time can also be compared to the IV flow rates determined by counting drops to verify the accuracy of each method. Without interfering with or changing the healthcare providers normal or traditional IV routines, an unobtrusive machine vision camera and computer can "observe" the IV flow rates and automatically record them in the EMR.

The module or automated EMR system 101, 201 of this disclosure may capture anesthetic event data but it must be noted that the same technologies described herein for capturing anesthetic event data can be used throughout the hospital or outpatient health care system to capture and record medication administration, IV fluid administration, vital signs and patient monitor inputs, provider events and other data. Non-operating room heath care locations are included within the scope of this disclosure. While this disclosure focuses on the totality of functions offered by module 101, 201, each of the individual functions can be offered independently of module 101, 201.

The use of the term Electronic Anesthetic Record (EAR) as defined herein can include any memory such as an electronic surgical record (ESR), or an electronic medical record (EMR), and is not limited to anesthetic or surgical applications. Aspects of the modules 101,201 described herein can also be employed in recovery, hospital room and long-term care settings.

In an example, the module 201 of FIG. 2, can include a housing 299 having a lower section 299A and a tower-like upper section 299B, wherein the lower section 299A can be configured to house unrelated waste heat-producing electronic and electromechanical surgical equipment, and wherein the tower-like upper section 299B can be located on top of the lower section 299A. The module 201 can also include a cowling 299C external or internal to the housing 299 that substantially confines waste heat generated by the unrelated waste heat-producing electronic and electromechanical surgical equipment. In addition, the module 201 can include a system for monitoring the administration of one or more IV medications and fluids 228, 230. As shown in the combination of FIGS. 2, 4, 5 and 14, the system 228, 230 can include any of: a barcode 436 reader or an RFID 438 interrogator configured to identify the one or more IV medications or fluids; a machine vision digital camera 436 to capture an image of one or more of a syringe 406 or a drip chamber 1434A,B; processing circuitry 257 operably coupled to the barcode reader 436 or the RFID interrogator 438 (or the machine vision digital camera 436) to receive the identity of the one or more IV medications or fluids, the processing circuitry 257 operably coupled to the machine vision digital camera 436 to receive the captured image and determine a volume of medication administered from the syringe or fluid administered from an IV bag based on the image; and a display 226 operably coupled to the processing circuitry 257, the display 226 configured to receive instructions from the processing circuitry 257 to output the identity and determined volume of medication administered from the syringe or fluid administered from an IV bag.

Figure 15:
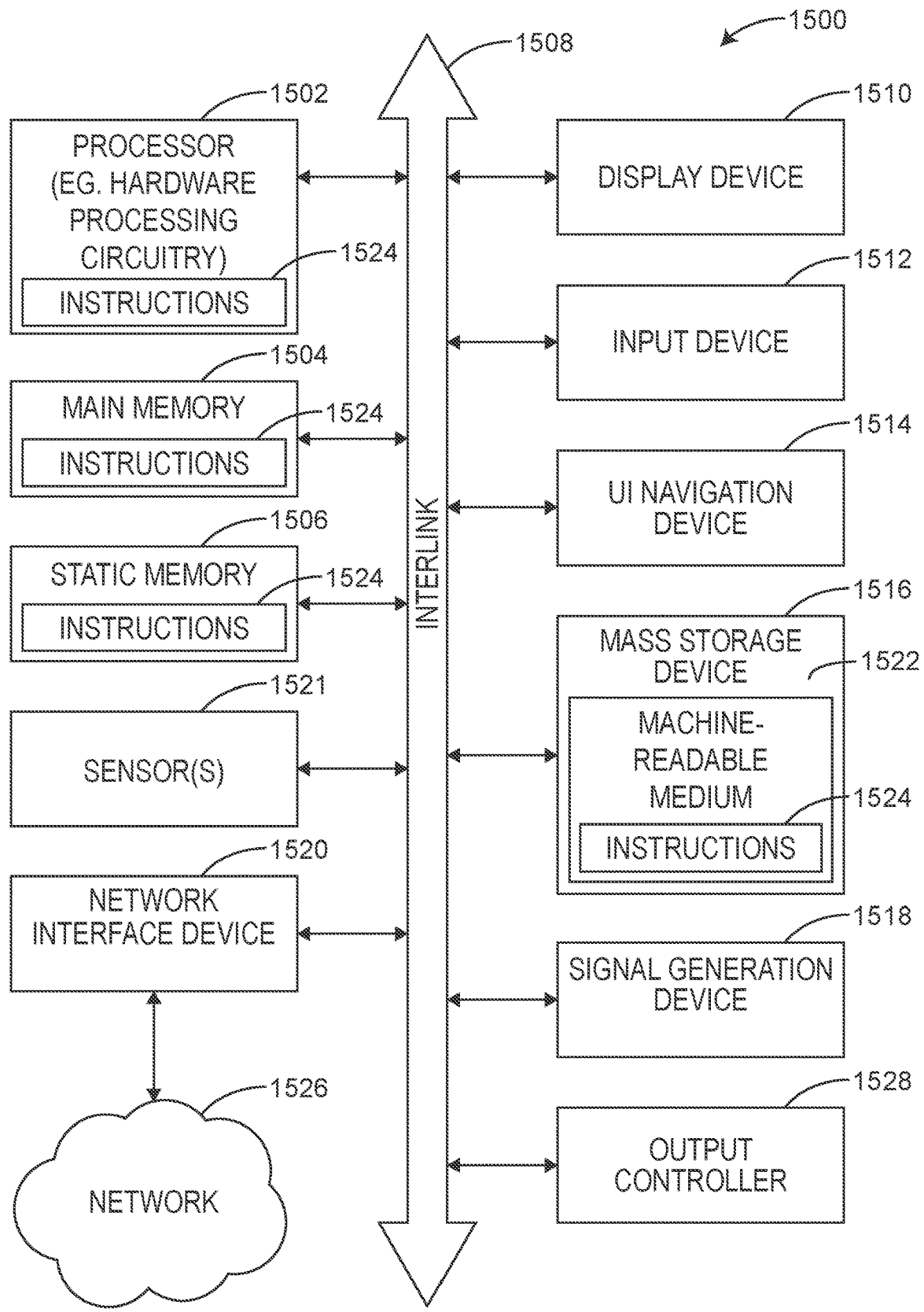
FIG. 15 illustrates generally an example of a block diagram of a machine (e.g., of module 101, 201) upon which any one or more of the techniques (e.g., methodologies) discussed herein may perform in accordance with at least one example of this disclosure.

FIG. 15 illustrates an example electronic and/or electromechanical system 1500 of a medical system in accordance with some examples described herein. The system 1500 will be described with respect to the medical system 20, but can include any of the features described herein to perform any of the methods or techniques described herein, for example, by using the processor 1502. The processor can include processing circuitry 157 or 257 of FIGS. 1 and 2. In some examples, the processing circuitry 1502 can include but is not limited to, electronic circuits, a control module processing circuitry and/or a processor. The processing circuitry may be in communication with one or more memory and one or more storage devices. A single processor can coordinate and control multiple, or even all the aspects of the system 1500 (e.g., of modules 101, 201), or multiple processors can control all the aspects of the system 1500. In some examples the storage device 1516 or memory 1504, 1506, 1516 can include at least a portion of the patient's anesthetic record saved thereon. The system 1500 can also include any of the circuitry and electronic and/or electromechanical components described herein, including but not limited to, any of the sensor(s) described herein (e.g., sensors 1521), such as but not limited to, RFID barcode or QR codes sensors, machine vision cameras, retinal scanners, facial recognition scanners, fingerprint readers, actuators and position sensors described herein. The system 1500 may also include or interface with accessories or other features such as any of: a remote display or wireless tablet (e.g., 287, FIG. 2), as well as any of the other systems described herein.

The processing circuitry 1502 can receive information from the various sensors described herein, make various determinations based on the information from the sensors, output the information or determinations from the information for output on the display or wireless tablet, output instructions to provide an alert or an alarm, power various components, actuate actuators such as clamps and flow managing devices, etc., or alert another system or user, as described herein. For the sake of brevity, select systems and combinations are described in further detail above and in the example sets provided in the Notes and Various Examples section below. Other embodiments are possible and within the scope of this disclosure.

Further, FIG. 15 illustrates generally an example of a block diagram of a machine (e.g., of module 101, 201) upon which any one or more of the techniques (e.g., methodologies) discussed herein may be performed in accordance with some embodiments. In alternative embodiments, the machine 1500 may operate as a standalone device or may be connected (e.g., networked) to other machines. In a networked deployment, the machine 1500 may operate in the capacity of a server machine, a client machine, or both in server-client network environments. The machine 1500, or portions thereof may include a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1500 may include a hardware processor 1502 (e.g., processing circuitry 157, 257, a central processing unit (CPU), a graphics processing unit (GPU), a hardware processor core, or any combination thereof), a main memory 1504 and a static memory 1506, some or all of which may communicate with each other via an interlink (e.g., bus) 1508. The machine 1500 may further include a display unit 1510, an alphanumeric input device 1512 (e.g., a keyboard), and a user interface (UI) navigation device 1514 (e.g., a mouse). In an example, the display device 1510, an input device such as an alphanumeric input device 1512 and UI navigation device 1514 may be a touch screen display. The display unit 1510 may include goggles, glasses, or other AR or VR display components. For example, the display unit may be worn on a head of a user and may provide a heads-up-display to the user. The alphanumeric input device 1512 may include a virtual keyboard (e.g., a keyboard displayed virtually in a VR or AR setting.

The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensor. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices or actuators of the system. Peripheral devices can include but are not limited to any displays, controllers or memories in electrical communication with the system, and actuators can include but are not limited to: one or more stop-flow clamps 1060A,B (FIG. 10) and one or more flow rate clamps 1478 (FIG. 14) of the system.

The storage device 1516 may include a machine readable medium 1522 that is non-transitory on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media that may be non-transitory.

While the machine readable medium 1522 is illustrated as a single medium, the term "machine readable medium" may include a single medium or multiple media (e.g., a centralized or distributed database, or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communications network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

Some of the benefits of the safety and security systems 100, 200 of FIGS. 1 and 2 and the subsystems described throughout this disclosure, and including the machine 1500 (FIG. 15), can include features to help with monitoring medication, fluid and anesthesia delivery, as well as documenting medication, fluid and anesthesia delivery, as well as other functions. In general, doctors and nurses are not interested in replacing themselves and their jobs with automated drug delivery or automated anesthesia systems. However, there is great interest in automated record keeping. Virtually all healthcare providers would prefer the "old" paper record and a pen to the "new" computer records. Filling out the electronic medical record (EMR) using a computer keyboard, mouse and various menus is widely viewed as a slow, cumbersome and distracting process. The challenge with automated record keeping is automating the data input that documents the numerous activities, anesthesia related events, fluid, gas and medication administration, ventilator settings, pressure off-loading effectiveness, as well as outputs such as blood loss and urine output, that constitute an anesthetic experience.

A challenge in implementing the safety and security system and fluids 100, 200 with an automated electronic anesthetic record (EAR) or electronic medical record (EMR) is to force as little change in the caregiver's routine as possible onto the clinicians using this system. Medical personnel tend to be creatures of habit and tradition and they generally do not like change. For example, IV medications are traditionally administered from a syringe and the dose is determined by the caregiver observing the plunger moving relative to a scale printed on the syringe. Maintaining this general technique of drug administration may have the highest probability of acceptance by healthcare users who are typically slow to embrace changes in their routine.

Further with regard to benefits of the modules, systems and machines described herein, the safety and security system 200 of module 201 can generate an automated electronic medical record (EMR) with the module 201 locatable proximate to the patient 202. The module 201 can be a module for housing unrelated electronic and electromechanical surgical equipment. The module 201 need not necessarily be configured to house unrelated electronic and electromechanical surgical equipment in all examples, and other modules can include the system for generating an automated EMR.

The module 201 can be an automated EMR system that can include one or more systems (e.g., 200, 228, 230) configured to measure (e.g., monitor) and record one or more of functions involved in a surgical anesthetic environment, and can include life support functions. The one or more systems 228, 230 can measure and record data automatically. However, in some examples, a user may initiate any of the systems described herein to measure and/or record data. These various measurements may be electronically recorded (such as on mass storage 1516 (FIG. 15) and displayed on the electronic anesthetic record display 226 (e.g., display device 1510, FIG. 15). Inputs to the automated EMR system may be managed by the anesthetic record input component 224 (e.g., input device 1512; FIG. 15). The anesthetic record input component 224 (e.g., input device 1512; FIG. 15) can include a touch-screen display 226 that organizes all of the inputs to the EMR into easily accessed and utilized information. In some examples, and as shown in FIG. 2, the identification and measurement system 228 of this disclosure may be located proximate the patient 202. The control displays for the identification and measurement system 228 may include a dedicated display proximate the identification and measurement system 228 or may be shared space on the anesthetic record input component 224 or display 226. In these locations, the information and controls of the identification and measurement system 228 can be viewed by the anesthesiologist or other user, in a single field of vision with the patient and surgical field.

Example methods of employing the systems, modules and machines disclosed herein are described throughout this disclosure and in the methods of FIGS. 16-21 which are illustrative in nature. Other methods described herein may also be performed by the systems, modules and machines described herein, and the systems modules and machines described herein may be used to perform other methods.

Figure 16:
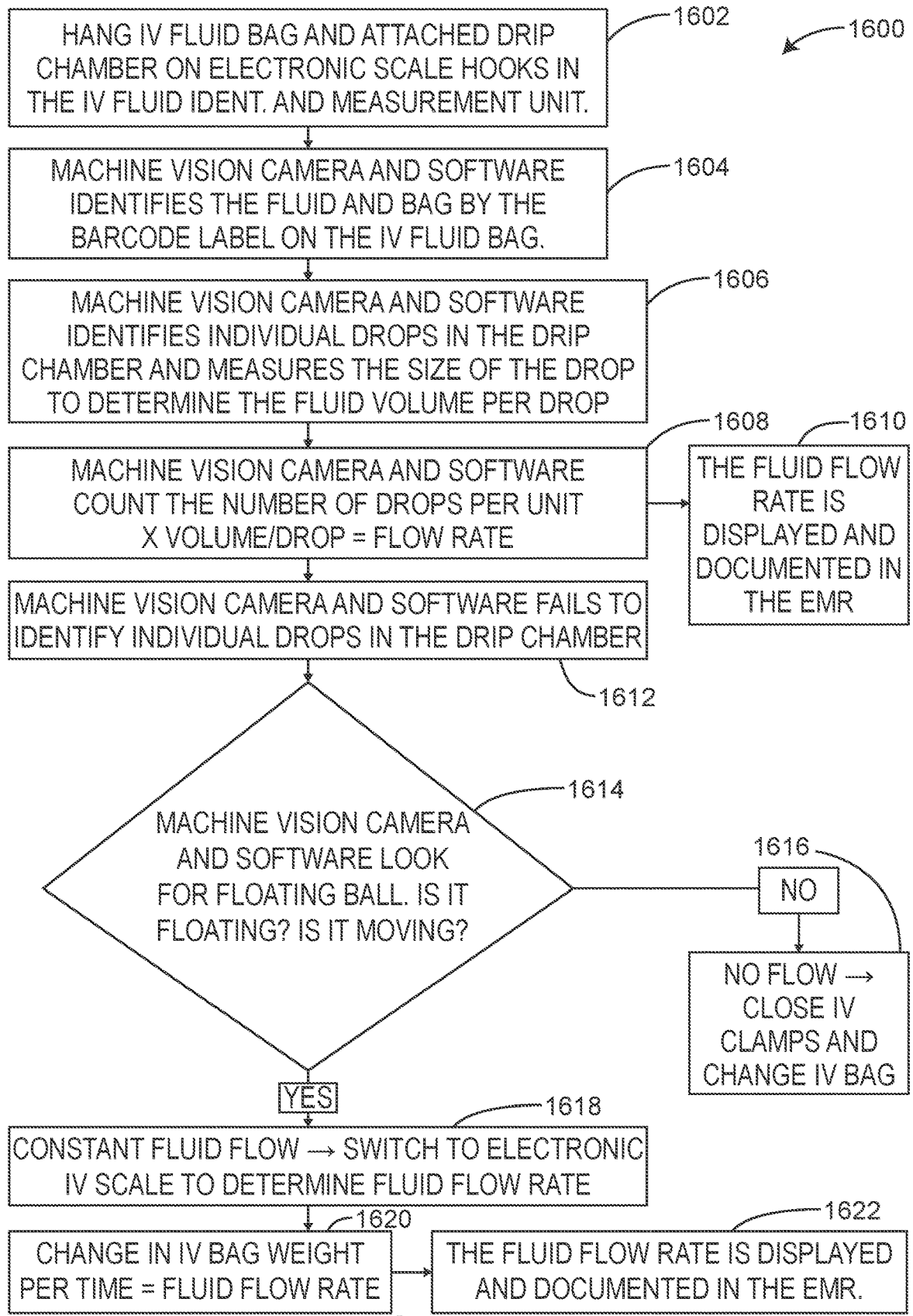
FIG. 16 is a flow chart illustrating a technique of IV fluid identification and measurement, in accordance with at least one example of this disclosure.
Figure 17:
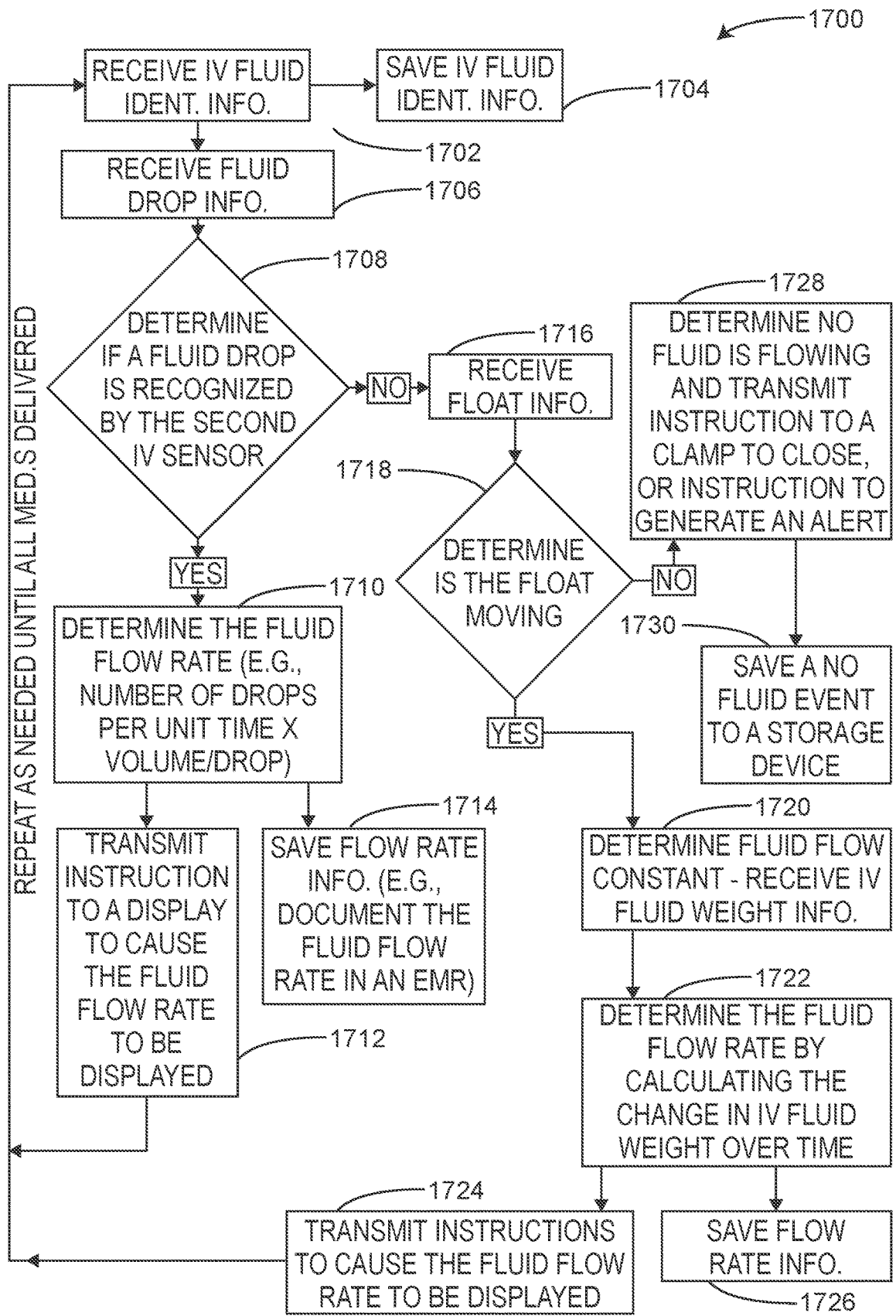
FIG. 17 is a second flow chart illustrating the technique of IV fluid identification and measurement, in accordance with at least one example of this disclosure.
Figure 18:
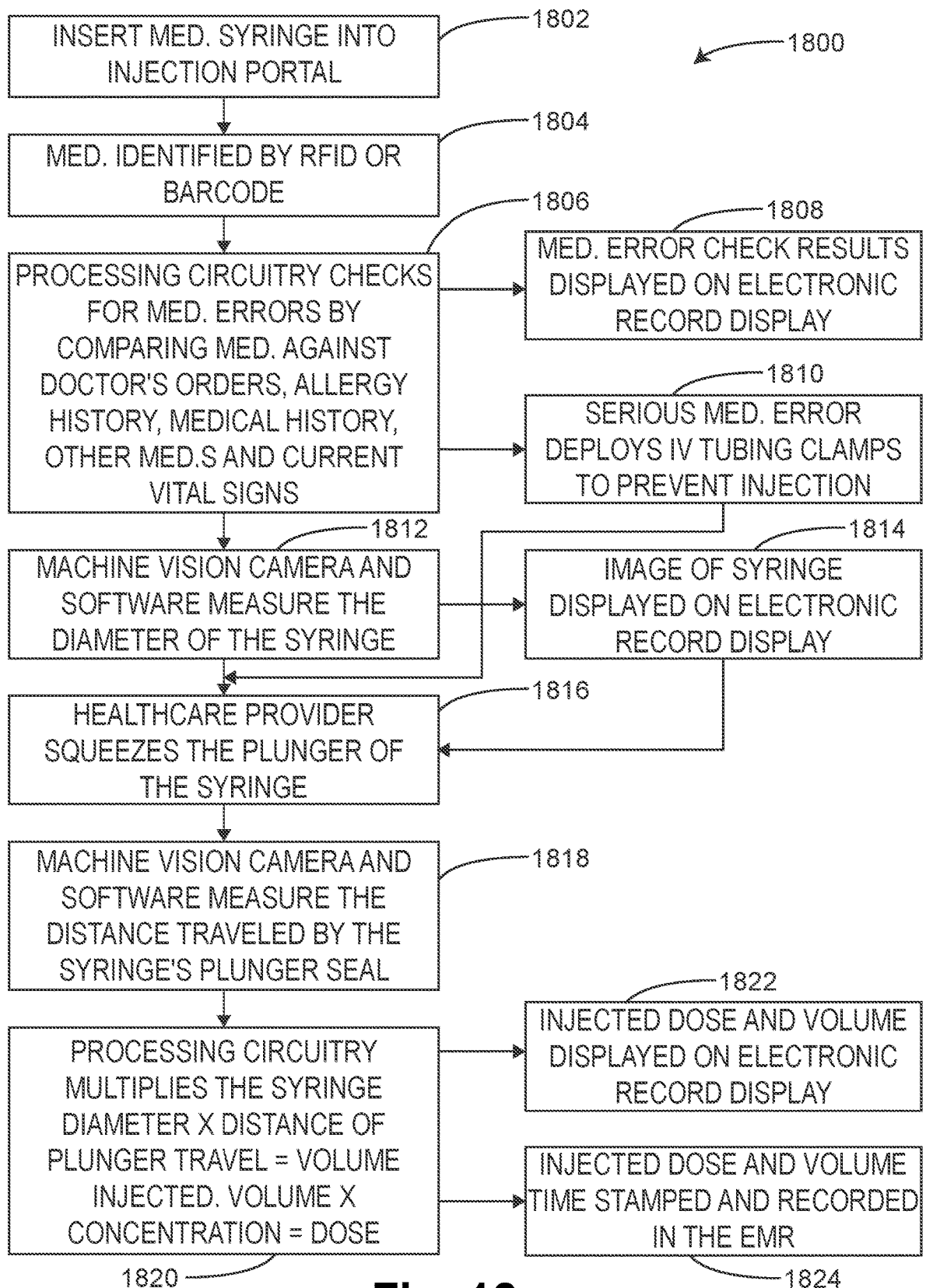
FIG. 18 is a flow chart illustrating a technique of medication identification and measurement, in accordance with at least one example of this disclosure.

FIGS. 16-18 show flow charts illustrating techniques for identification, measurement, monitoring, security and safety related to medications and/or IV fluids. The methods may be used with the systems, sub-systems and modules of FIGS. 1-15 (e.g., 101, 201, 1500), but may also be used with other systems. Likewise, the systems, subsystems of modules of FIGS. 1-15 may also be used with other methods. The techniques 1600, 1700, 1800, 1900, 2000, 2100, 2300 can be performed by at least one non-transitory machine-readable medium (e.g., computer readable) including instructions for operation of the systems described herein. Some steps of techniques may be performed by a provider. The systems can include processing circuitry (e.g., 157, 257, 1500, including one or more processors, processing circuitry hardware) for executing the instructions. The instructions, when executed by the processing circuitry can cause the processing circuitry to perform operations described in FIGS. 16-21 and 23, and as described in the examples throughout this disclosure.

FIG. 16 is a flow chart illustrating an example technique 1600 of IV fluid identification and measurement. To start the technique, in operation 1602 a provider hangs an IV fluid bag and attached drip chamber on electronic scale hooks in an IV fluid identification and measurement unit (e.g., FIG. 14). In operation 1604, a machine vision camera and software can identify the fluid and bag by the barcode label on the IV fluid bag. In operation 1606, the machine vision camera and software can identify the individual drops in the drip chamber and measure the size of the drop to determine the fluid volume per drop and count the number of drops per unit time. In operation 1608 the machine vision camera and software can calculate the flow rate by multiplying the number of drops per unit time by the volume/drop. In operation 1610, the fluid flow rate is displayed and documented in the EMR.

In operation 1612, if the machine vision camera and software fails to identify individual drops in the drip chamber, in operation 1614 the machine vision camera and software can look for a floating ball (e.g., float) that is located in the drip chamber to determine if the ball is floating and if the ball is moving. In operation 1616, when the ball is not floating and/or moving, IV clamps are closed and the provider can change the empty IV bag if necessary. In operation 1618, if the machine vision camera and software can determine that the ball is floating and moving, the system determines that the fluid flow is so fast that the fluid flow is constant or continuous such that individual drops cannot be measured. In operation 1618, because individual drops cannot be determined, the system switches to measuring the fluid flow rate using an electronic IV scale (FIG. 14) to determine the fluid flow rate. In operation 1620, the fluid flow rate can be determined by monitoring the change in IV bag weight per time. In operation 1622, the fluid flow rate can be displayed and documented in the EMR.

FIG. 17 is a second flow chart illustrating a technique 1700 including aspects of the technique 1600 of IV fluid identification and measurement from the perspective of processing circuitry (e.g., 257, FIG. 2; 1502, FIG. 15). The technique 1700 may include an operation 1702 to receive IV fluid identification information from a first IV sensor (e.g., one or more sensors), such as an RFID or barcode reader to identify the fluid or other characteristics of an IV fluid bag as described herein. Operation 1704 can include saving the IV identification information to a storage device (e.g., one or more storage devices, memory, EMR). Operation 1706 can include to receive fluid drop information from a second IV sensor, such as a machine vision camera that detects, senses and measures an individual drop in a drip chamber to determine a fluid volume per drop and measure the number of drops per unit of time. While the illustrative example of FIG. 17 includes the first IV sensor and the second IV sensor, in some examples the first IV sensor and the second IV sensor can be the same sensor or same one or more sensors. Operation 1708 can include to determine if a fluid drop was recognized by the second IV sensor. If in operation 1708 it is determined that a fluid drop was recognized, operation 1710 can include determining a fluid flow rate, such as by calculating the flow rate by multiplying the number of drops per unit time by the volume per drop. In some examples, the volume per drop is measured, while in other examples the volume per drop may be input by a user, or can be a value retrieved from a memory. Operation 1712 can include transmitting instructions to a display to cause a fluid flow rate to be displayed. Operation 1714 can include saving flow rate information to the storage device to document the fluid flow rate in the EMR. Any time a change is input or detected in the system, updated flow rate information can be displayed and saved.

If in operation 1708 it is determined that a fluid drop was not recognized, operation 1616 can include receiving float information from the second IV sensor or another IV sensor. The float information can include information about a float in the drip chamber including is the float still (e.g., not moving), moving, or is movement of the float slowing down. Operation 1718 can include determining if the float is moving. If the float is moving, Operation 1720 can include determining the fluid flow is constant. In such a scenario, the fluid is flowing but the fluid is flowing so quickly that individual drops of fluid cannot be distinguished because the fluid is flowing as a steady stream. Operation 1720 can further include determining the fluid flow rate by receiving IV bag physical characteristic information from a physical characteristic sensor, such as a weight sensor. The physical characteristic information can include weight information from the weight sensor (e.g., scale). Operation 1722 can include determining the fluid flow rate by calculating the change in IV bag weight over a period of time. In other examples, instead of weight information, the physical characteristic information can include a position of the IV bag that changes as a result of a change in weight, without the physical characteristic data corresponding directly to a weight measurement. Other physical characteristics and other physical characteristic sensors configured to monitor IV fluid delivery may be provided such that an automated, or at least partially automated EMR system is enabled.

If in operation 1718 it is determined that the float is not moving, operation 1728 can include determining that no fluid is flowing from the IV bag and transmitting one or more of: an instruction an actuator such as a clamp, to cause the actuator to inhibit fluid flow to the patient (e.g., close the clamp onto IV tubing to prevent flow); and transmit and instruction to an indicator (e.g., display, audible, tactile indicator) to cause an alert to be generated. Operation 1730 can include saving a no fluid event to the storage device.

FIG. 18 is a flow chart illustrating an example technique 1800 of medication identification and measurement. In operation 1802 a provider inserts a medication syringe into an injection portal (e.g., 411, FIG. 4). In operation 1804 the medication can be identified by a sensor such as by at least one of the RFID, barcode or QR sensors described herein. In operation 1806 processing circuitry checks for medication errors by comparing the medication against one or more of: a doctor's orders, allergy history, medical history, other medications and current vital signs. In operation 1808, the results of the medication error check can be displayed on an electronic record display. The results can indicate no error, the presence of an error, specific details about the error, or present a link to access information including additional details about the error. In operation 1810, if a serious medication error is recognized, the error deploys (e.g., causes actuation of) IV tubing clamps (e.g., 1060A, 1060B of FIG. 10) to prevent injection of the medication.

If in operation 1812, such as when no errors are determined, the machine vision camera and software can measure the diameter of the syringe. In operation 1814, an image of, or representation of the image of the syringe, is displayed on the electronic record display. In operation 1816 the provider squeezes the plunger of the syringe. In operation 1818, the machine vision camera and software measure the distance traveled by the syringe's plunger seal (e.g., 548, FIG. 5). In operation 1820 the processing circuitry calculates the volume injected by multiplying the syringe diameter times the distance of plunger travel. The processing circuitry can also calculate the dose by multiplying the volume injected by the concentration of the medication. In operation 1822 the injected dose and volume are displayed on the electronic record display. In operation 1824 the injected dose and volume are time stamped and recorded in the electronic medical record.

Figure 19:
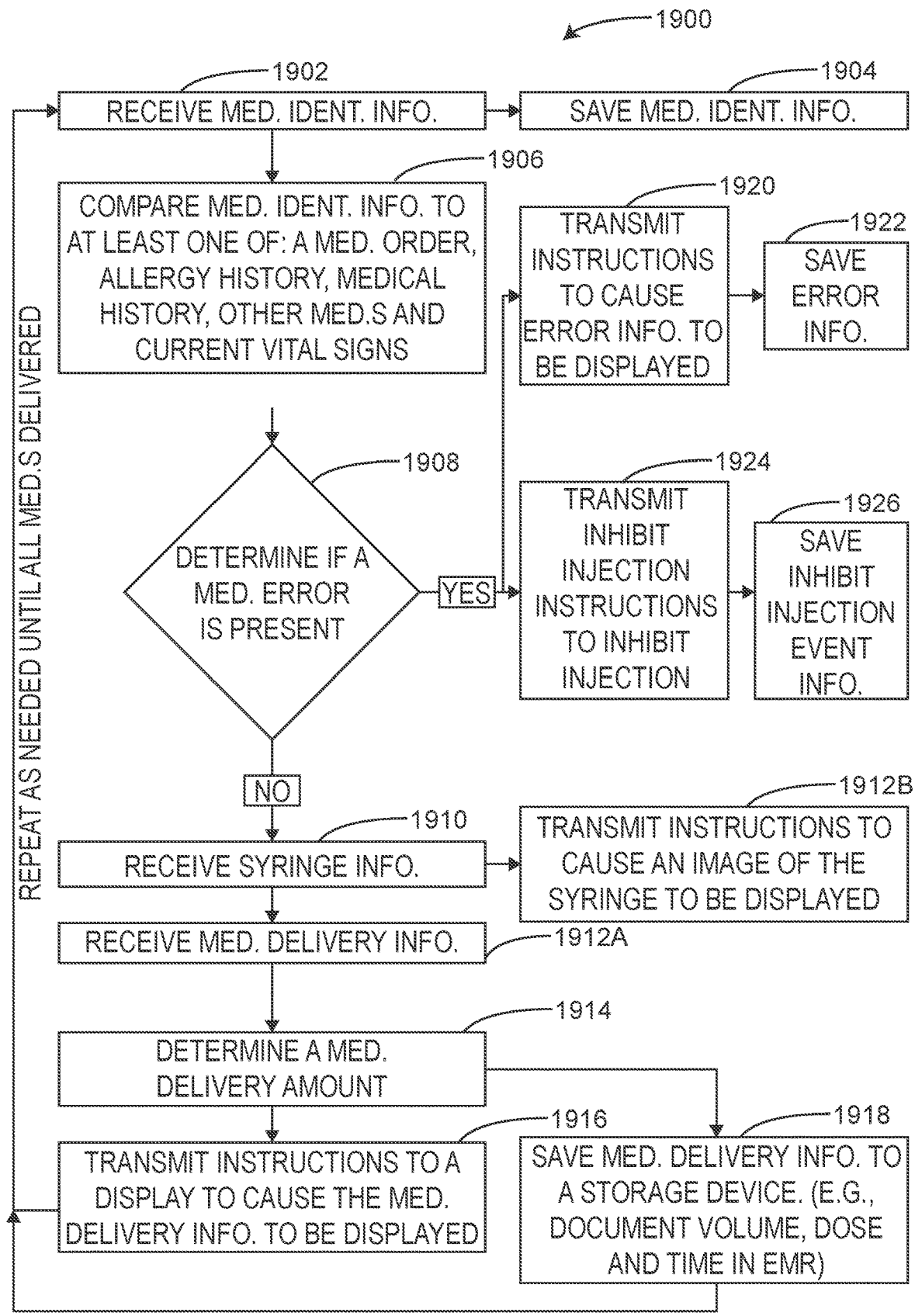
FIG. 19 is a second flow chart illustrating a technique of medication identification and measurement, in accordance with at least one example of this disclosure.

FIG. 19 is a second flow chart illustrating a technique 1900 including aspects of the technique 1800 of medication identification and measurement from the perspective of processing circuitry (e.g., 157, FIG. 1; 257, FIG. 2; 1502, FIG. 15).

Technique 1900 can include an operation 1902 to receive medication identification information such as medication type, concentration, brand, lot number or amount, from a first medication sensor (e.g., RFID, barcode or QR reader). Operation 1904 can include saving medication identification information to a storage device (e.g., one or more storage devices, memory). Operation 1906 can include comparing medication identification information to at least one of a medication order, allergy history, medical history, other medications ordered for the patient, and vital signs (e.g., previously obtained vital signs or current vital signs of the patient via continuous monitoring). Operation 1908 can include determining if a medication error is present. Operation 1910 can include receiving syringe information from a second medication sensor (e.g., a sensor configured to measure diameter, such as a machine vision camera). Operation 1912A can include receiving medication delivery information from the second medication sensor or another medication sensor. In some examples, the medication delivery information can include a distance of a syringe plunger travel.

Operation 1912B can include transmitting instructions to a display to cause an image of the syringe (e.g., actual image or representation of the syringe) to be displayed. A representation of the syringe can include an image communicating information about the syringe that is not an image of the actual syringe or can be a modified image of the syringe, such as to highlight or point out aspects of the syringe or medication within the syringe Using the medication delivery information obtained in operation 1912A, operation 1914 can include determining a medication delivery amount. Operation 1916 can include transmitting instructions to a display (e.g., display 226, FIG. 2) to cause the medication delivery information or medication delivery amount to be displayed.

If in operation 1908 it is determined that a medication error is present, operation 1920 can include transmitting instructions including error information to the display or another display to cause the error information to be displayed. In some examples, any of the instructions described herein that are sent to the display can be sent to one or more displays. Such displays can be located locally or remotely (e.g., in a different part of a room, in a separate room, in another building, in another state, in another country), to alert multiple providers. For example, a provider such as a nurse anesthetist located adjacent to the patient can be alerted to and provided with the information via display 226. In addition, a second provider, such as an anesthesiologist supporting the nurse anesthetist, and who may be supporting other nurse anesthetists working in different rooms, can also be alerted on a display of a mobile device, which may prompt them to check in with and potentially assist the nurse anesthetist. This concept can be applied outside the operating room to manage medication delivered by providers working in different rooms of a hospital or other care center, while a second provider such as a nurse manager, nurse practitioner, pharmacist or doctor oversees the work of the first provider. In operation 1922 the error information can be saved to one or more storage devices (e.g., 259, FIG. 2; 1516, FIG. 15).

Also in response to determining that a medication error has occurred in operation 1908, operation 1924 can include transmitting instructions to an actuator such as an IV tubing clamp to inhibit (e.g., prevent, reduce, limit) injection. In some examples, the actuator can reduce or limit the amount of the injection to a specified amount rather than completely inhibiting or preventing administration of the medication. Operation 1926 can include saving an inhibit injection event information to a storage device, such as any of the one or more storage devices (e.g., 259, FIG. 2; 1516, FIG. 15). The inhibit injection event information can include information such as the time of the event and the action taken to inhibit injection and how much the injection was inhibited (e.g., partially inhibited, completely inhibited, or amount of medication inhibited from injection).

If in operation 1908 it is determined that a medication error has not occurred, operation 1910 can include receiving syringe information including a syringe diameter from a sensor such as a machine vision camera. In some examples, the sensor can be the first medication sensor or can be a second medication sensor. Operation 1912A can include receiving medication delivery information from a sensor such as from the first medication sensor, the second medication sensor or another sensor. The medication delivery information can include a distance of plunger travel relative to a syringe body. Operation 1912B can include transmitting instructions to one or more displays such as, display 226, FIG. 2, to cause an image of the syringe or representation of the syringe to be displayed.

Operation 1914 can include determining a medication delivery amount, such as a volume or dose injected. For example, the volume injected can be calculated by multiplying the syringe diameter by the distance of plunger travel. The dose injected can be calculated by multiplying the volume injected by the concentration of the medication.

Operation 1916 can include transmitting instructions to the one or more displays to cause the medication delivery information to be displayed. Operation 1918 can include saving medication delivery information to the storage device (e.g., EMR). In some examples, the medication delivery information can include, but is not limited to, volume, dose, time of the injection, or time period of the injection.

Figure 20:
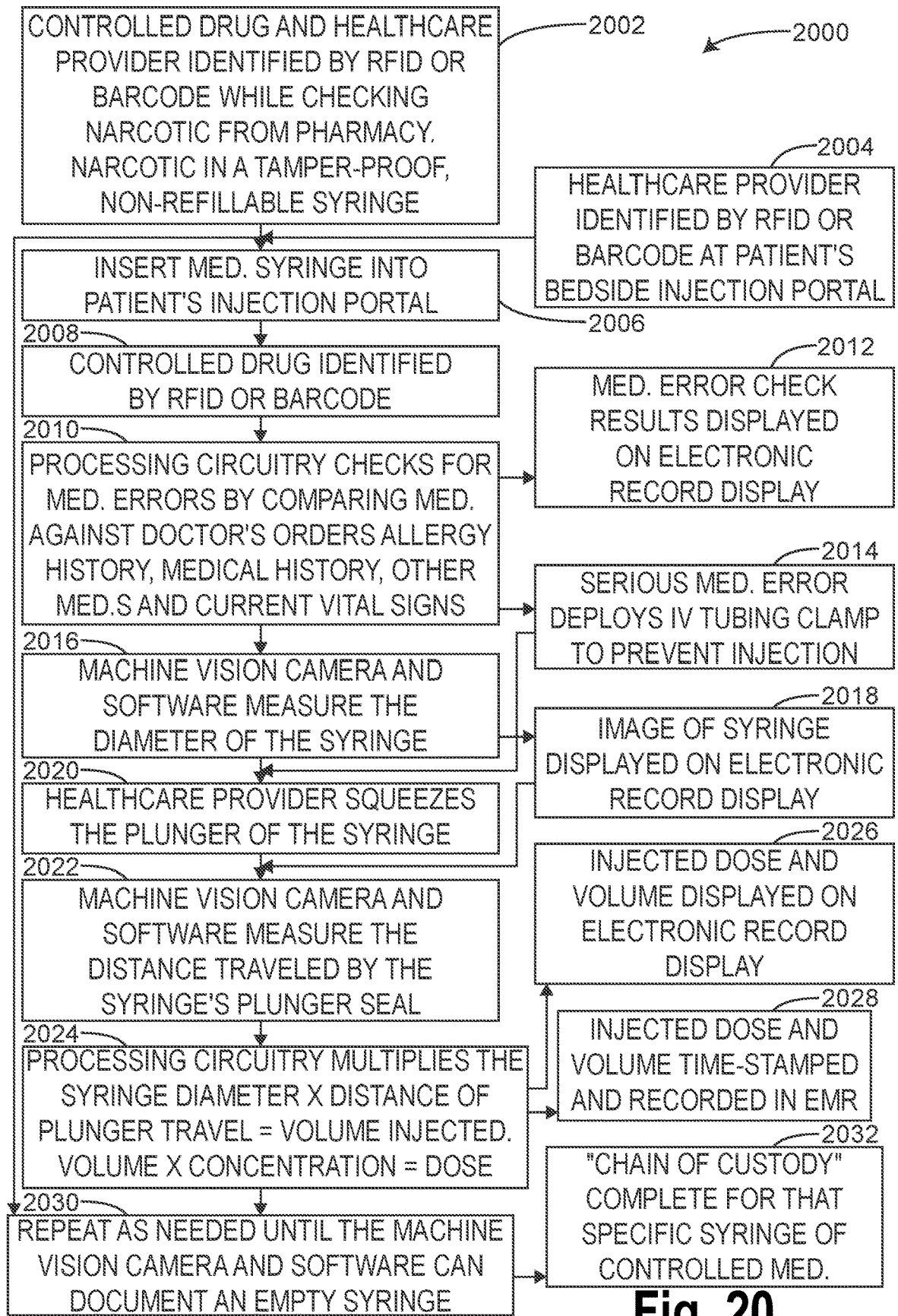
FIG. 20 is a flow chart illustrating a second technique of IV fluid identification and measurement including safety and security aspects, in accordance with at least one example of this disclosure.

FIG. 20 is a flow chart illustrating an example of a second technique of IV fluid identification and measurement including safety and security measures. Aspects of technique 2000 can be similar or the same as techniques 1800 and 1900, however, technique 2000 is particularly well-suited to the challenges of maintaining safety and security with controlled drugs such as narcotics. Technique 2000 can include operation 2002 of identifying a medication (e.g., a controlled drug) and identifying a health care provider, such as by RFID, barcode or QR code reader, retinal scanner, facial recognition, or fingerprint. Operation 2002 can occur at the time a provider checks out a drug from a pharmacy or a medication dispensing machine. The medication can include a narcotic in a tamper-proof, non-refillable syringe.

Operation 2004 can include identifying a provider such as by RFID, barcode or QR code reader, retinal scanner, facial recognition, or fingerprint at a patient's bedside, such as at an injection portal (e.g., 411, FIG. 4). The provider can be the same or a different provider as the provider in operation 2002. In operation 2006, the provider inserts the medication syringe into the patient's injection portal. In operation 2008, the controlled drug is identified, such as by an RFID, barcode or QR code reader associated with the injection portal. Operation 2010 can include processing circuitry checking for medication errors by comparing the medication against doctor's orders, allergy history, medical history, other medications and vital signs. Operation 2012 can include displaying medication error check results on a display, such as display 226, FIG. 2. If the medication error is of a serious nature, the error can cause IV tubing clamps to prevent injection. Operation 2016 can include machine vision camera and software measuring the diameter of the syringe. Operation 2018 can include an image, or an image representing the syringe being displayed on a display, such as display 226, FIG. 2. Operation 2020 can include a provider squeezing the plunger of the syringe. Operation 2022 can include the machine vision camera and software measuring the distance traveled by the syringe's plunger seal (e.g., 548, FIG. 5). Operation 2024 can include processing circuitry determining the volume of medication injected by multiplying the syringe diameter by the distance of plunger travel or determining the dose of medication injected by multiplying the volume of medication injected by the concentration of the medication. Operation 2026 can include displaying the injected volume or dose on a display, such as display 226, FIG. 2.

Operation 2028 can include saving the injected volume or dose along with a timestamp to the EMR. Operation 2030 includes repeating the operations of technique 2000 as necessary until the machine vision camera and software documents an empty syringe. Operation 2032 includes completing the "chain of custody" for a specific syringe of controlled medication. The operations of technique 2000 can be repeated as necessary for other syringes, thereby completing the "chain of custody" for each syringe.

Figure 21:
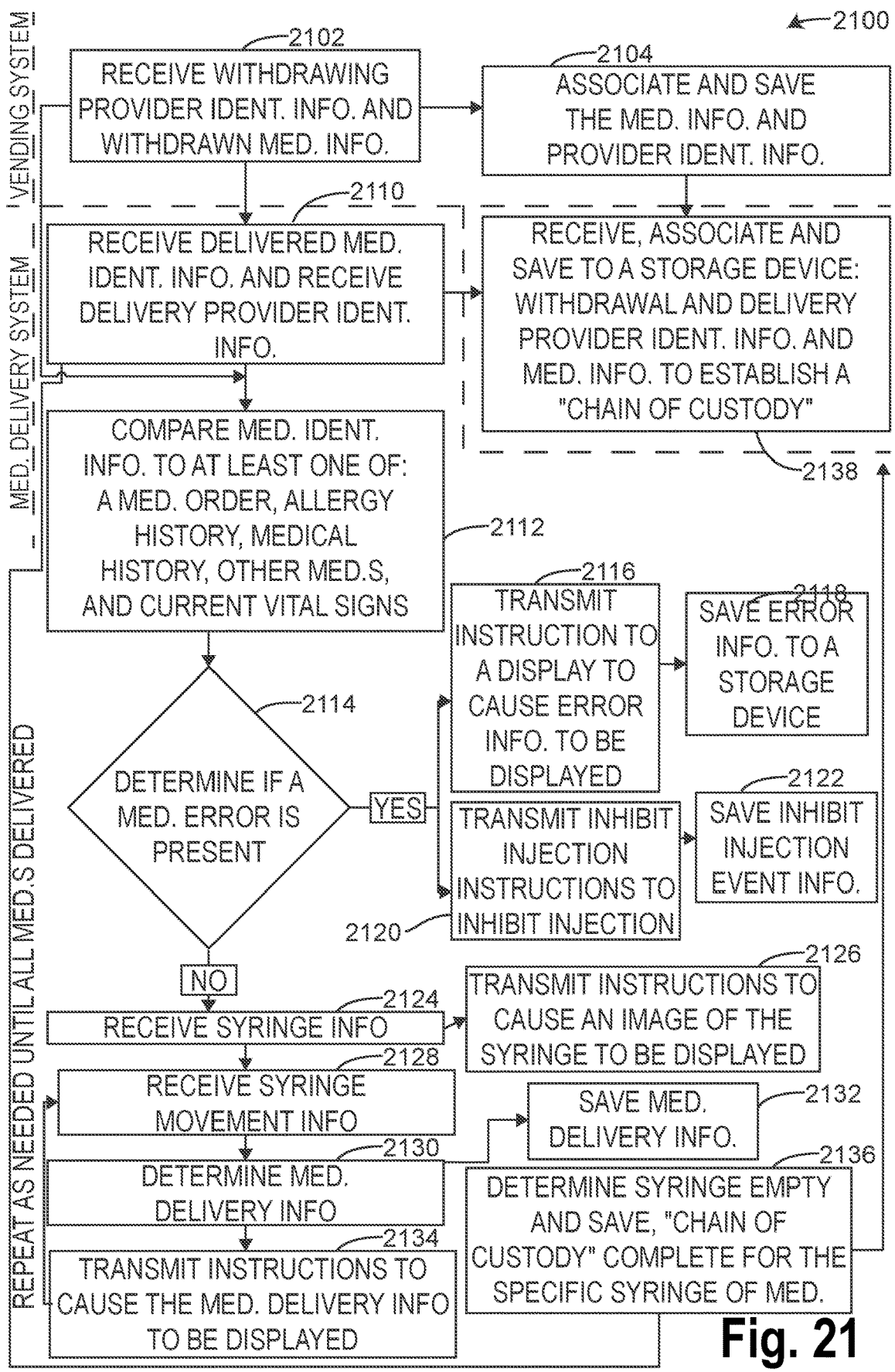
FIG. 21 is a second flow chart illustrating a second technique of IV fluid identification and measurement including safety and security aspects, in accordance with at least one example of this disclosure.
Figure 22:
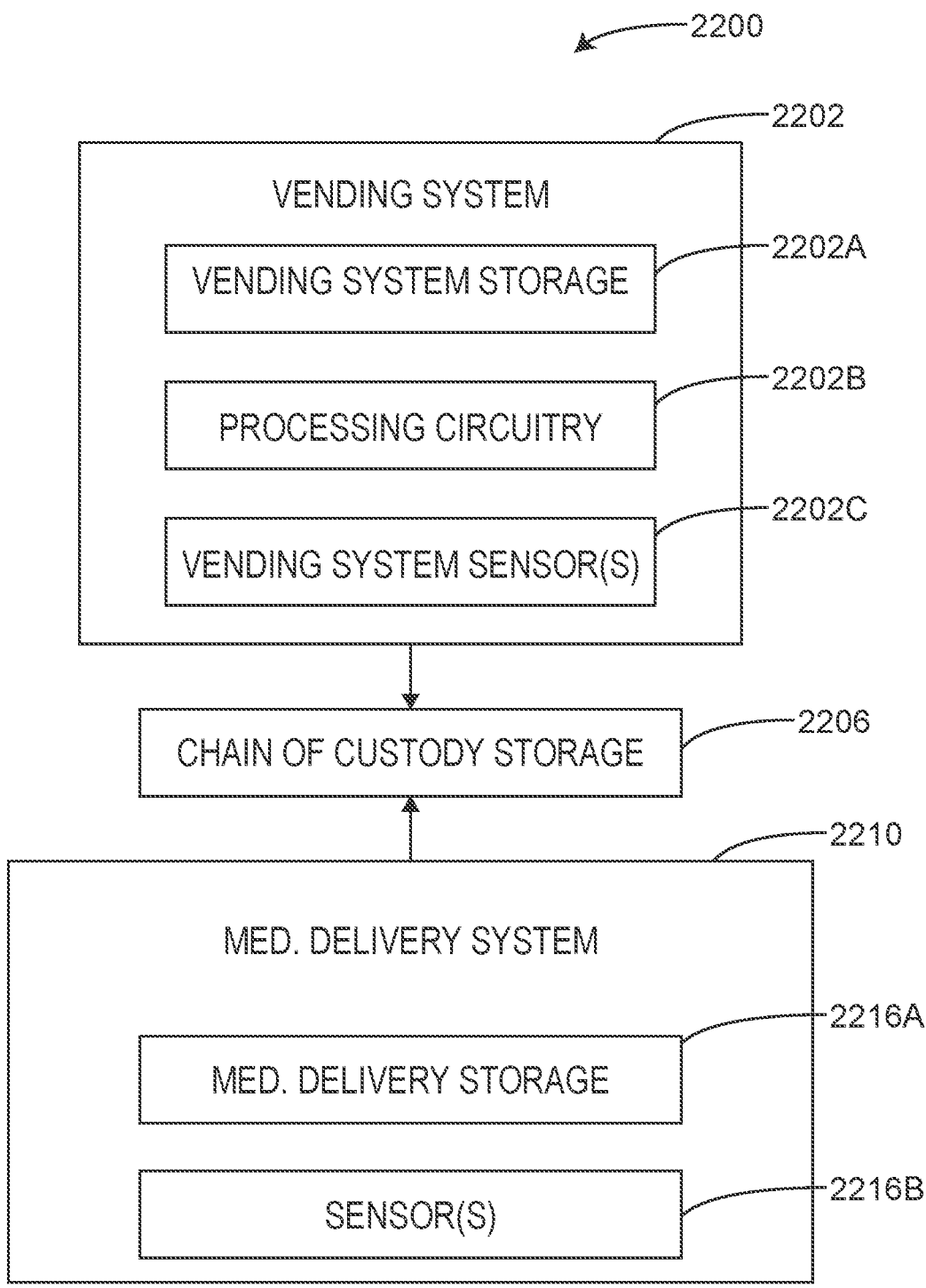
FIG. 22 illustrates generally an example of a block diagram of vending system and a medication delivery system of FIGS. 1-21 upon which any one or more of the techniques (e.g., methodologies) discussed herein may perform in accordance with at least one example of this disclosure.

FIG. 21 is a second flow chart illustrating a technique 2100 including aspects of the technique 2000 of IV fluid identification and measurement including safety and security measures from the perspective of processing circuitry, such as, but not limited to, processing circuitry 157, FIG. 1; 257, FIG. 2; 1502, FIG. 15. The technique may involve processing circuitry 2202B, such as may be part of a medication vending system as shown in FIG. 22. FIG. 22 illustrates generally an example of a block diagram of vending system and a medication delivery system of FIGS. 1-21 and 23 upon which any one or more of the techniques (e.g., methodologies) discussed herein may perform in accordance with some embodiments. FIGS. 21 and 22 are described together.

In some examples, operations 2102 and 2104 can be part of a vending system (2202, FIG. 22) for managing medication withdrawal from a pharmacy or other vending system. Operations 2110-2136 can be part of a medication delivery system (e.g., can be used with the bedside patient systems and modules shown and describe in FIGS. 1-15; medication delivery system 2210, FIG. 22). Operation 2138 can tie information, including data generated by the vending system 2202 and the medication delivery system 2210 together to facilitate tracking a "chain of custody" for a specific syringe of controlled medication from the pharmacy until the medication is completely injected into the patient. Chain of custody information can be stored to one or more of: the vending system storage 2202A, the medication delivery storage 2216, and chain of custody storage device (e.g., 2206, FIG. 22) and the EMR. Any of the storage described herein can include one or more storage devices or memory as described herein and can include other storage devices in electrical communication with the vending system or the medication delivery system.

Operation 2102 of the vending system can include receiving withdrawing provider identification information from a medication dispensing sensor 2202C, such as a first RFID or barcode reader that reads a badge of a provider and reads the medication identification information from a syringe or other medication container, or any other type of suitable sensor described herein. Operation 2104 can include associating and saving the medication identification information and the withdrawing provider identification information to a vending system storage device (e.g., 2202A, FIG. 22).

Operation 2110 can include receiving medication identification information from a first identification sensor (e.g., RFID, QR, barcode reader, or machine vision camera reads information about a medication) and receiving delivery provider identification information from the first identification sensor or another identification sensor (e.g., a second identification sensor, another RFID, QR or barcode reader, machine vision camera, retinal scanner, facial recognition sensor or fingerprint reader). In some examples, patient identification information can also be obtained from one of the first identification sensor, second identification sensor or another identification sensor, such as by scanning patient identification information on a hospital wristband. In some examples receiving the medication identification, the provider identification information or the patient identification can cause the processing circuitry to send an instruction to a display to prompt the user for the other of the medication identification information, the provider identification information or the patient identification information.

Operation 2112 can include comparing the received identification information to one or more of: a medication order, allergy history, medical history, other medications and current vital signs. Operation 2114 can include determining if a medication error is present. If it is determined that a medication error is present, operation 2116 can include transmitting instructions including error information to a display to cause the error information to be displayed. Operation 2118 can include saving the error information to one or more storage devices. Further, if in operation 2114 it is determined that a medication error has occurred, operation 2120 can include transmitting inhibit injection instructions to an actuator such as, but not limited to, an IV tubing clamp (e.g., 1060A, 1060B; FIG. 10) to inhibit injection. Operation 2122 can include saving an inhibit injection event information to one or more storage devices.

Operation 2124 can include receiving syringe information from a second medication sensor (e.g., syringe diameter including syringe inner diameter, outer diameter, or wall thickness from a machine vision camera). Operation 2124 can include receiving syringe size information from a data storage device, the syringe size information provided by the syringe manufacturer that supplies the specific syringes used by the specific healthcare facility. Operation 2126 can include transmitting instructions to a display to cause an image of the syringe or a representation of the syringe to be displayed. Operation 2128 can include receiving syringe movement information from the second medication sensor or another sensor. Syringe movement information can include, for example, a distance of travel of the syringe plunger relative to the syringe barrel.

Operation 2130 can include determining medication delivery information based on the syringe movement information. Medication delivery information can include, for example, a volume or dose of medication delivered to the patient (e.g., ejected from the syringe). In some examples, the volume of medication delivered (e.g., ejected from the syringe) can be calculated by multiplying the syringe inner diameter by the distance of plunger travel. Likewise, the dose of medication delivered can be calculated by multiplying the calculated volume by a concentration of the medication. Operation 2132 can include saving medication delivery information to one or more storage devices. In other words, operation 2132 can include documenting volume, dose and time in an EMR, in some cases automatically without intervention from a provider.

Operation 2134 can include transmitting instructions to one or more displays described herein to cause the medication delivery information to be displayed. Operation 2136 can include determining that a syringe is empty and saving "chain of custody" complete for the specific syringe of medication (e.g., controlled drug) to one or more storage devices.

To complete and document the chain of custody, thereby ensuring the medication was delivered to the patient, operation 2138 can include one or more of receiving, associating and saving to one or more chain of custody storage devices (e.g., 2206, FIG. 22), information from both the pharmacy vending system 2202 (FIG. 22) and the bedside medication delivery system 2210 (FIG. 22)(e.g., 1516; FIG. 15). In some examples the one or more chain of custody storage devices is not necessarily separate from the vending system storage 2202A or the medication delivery storage 2216, but rather can reside with one or the other systems, a different system, multiple systems or can be included as a single storage device.

Figure 23:
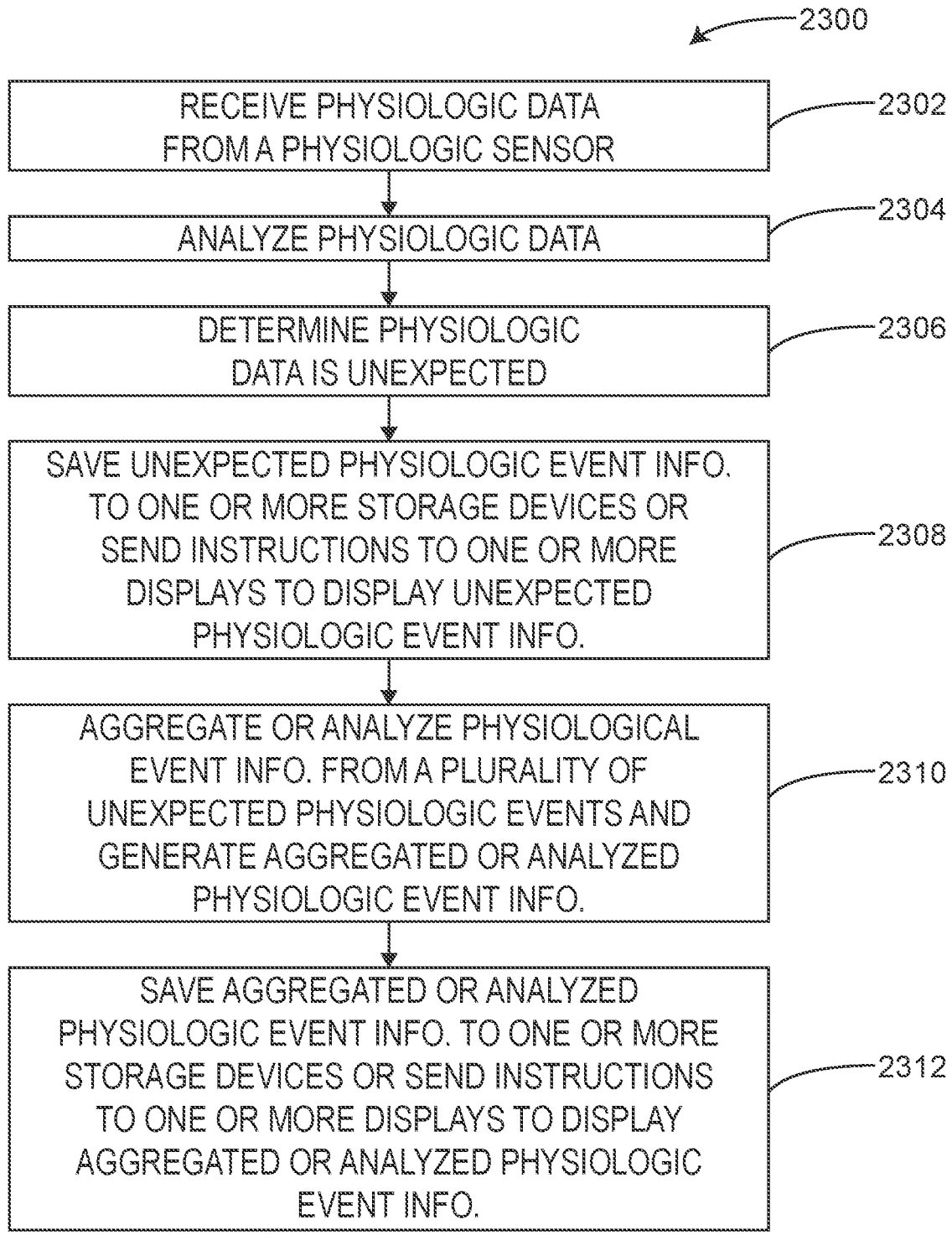
FIG. 23 is a flow chart illustrating a technique 2300 for assessing physiologic events, in accordance with at least one example of this disclosure.

FIG. 23 illustrates and example technique 2300 for assessing physiological events. In some examples, the EMRs created by the safety and security system 100, 200, 400, 600, 800 can provide the most accurate and temporally correlated information about the relationship between any injected medication and the resulting physiologic response. In some examples, this is uniquely accurate dose-response data can be used as a final check of the chain of custody for controlled medications or any medication. The processing circuitry 157, 257 may include or be in electrical communication with artificial intelligence (AI) and/or machine learning that can compare the measured physiologic response in the several minutes after a medication is injected, to the expected physiologic response for that dose of that medication. For example, if the injected medication was a narcotic, it would be expected that the heart rate and blood pressure of the patient would decrease quickly after the injection.

In some examples, if the expected physiologic response does not occur, the AI software of the safety and security system 100, 200, 400, 600, 800 may electronically "flag" that injection as suspicious. For example, if there is no physiologic response after injecting what was supposed to be a narcotic, it is possible that the drug had been stolen and replaced by saline. On the other hand, no response may simply mean that the patient is addicted to and tolerant of narcotics and that too is worth noting. An unpredicted response does not prove anything but multiple unpredicted responses in multiple patients can be suspicious. Therefore, aggregating or analyzing data over time for a particular patient or provider can alert management to issues. If any individual provider traverses a threshold number of flags (e.g., too many "flags") for unexpected physiologic responses (including no response), the safety and security system 100, 200, 400, 600, 800 can generate an alert to notify management and an investigation of that provider may be warranted. Knowing that AI is "watching" the patients' response to a healthcare providers' injected medications, can be a significant deterrent to tempted drug thieves.

Technique 2300 can include determining if one or more unexpected physiological events has occurred, analyzing saving, aggregating and displaying such information, in any order. The method can be performed by processing circuitry 157, 257, 1502, including other processing circuitry, memories and databases in electrical communication with processing circuitry 157, 257, 1502 to one or more of: receive physiologic data, analyze physiologic data, determine physiologic data is unexpected, create and send instructions to cause an alert to the provider or another user, or save a physiological event information to a storage device 1516 which may include a database. The physiological event information can include, but not limited to data generated by the various sensors and equipment described herein, including one more of: physiological information, patient information, provider information, medication information, time information, location information, facility information, equipment information, aggregated physiological event information and analyzed physiologic event information.

Operation 2302 can include receiving physiologic data from a physiologic sensor, Operation 2304 can include analyzing the physiologic data. Operation 2304 can include comparing the physiologic data to expected physiologic responses. Based on the outcome of the analysis in operation 2304, in operation 2306, the processing circuitry can determine if the physiologic data is unexpected, and if so, operation 2308 can include saving unexpected physiologic event information to one or more storage devices, or can include sending instructions to one or more displays to display unexpected physiologic event information.

Operation 2310 can include aggregating or analyzing physiologic event information from a plurality of unexpected physiological events and generating aggregated or analyzed physiologic event information. In some examples, aggregating can include aggregating a number of physiological events by counting the number of physiological events for a given provider, patient, group of patients, medical facility, type of medication, or any other suitable assessment. Operation 2312 can include saving aggregated or analyzed physiologic event information to one or more storage devices or sending instructions to one or more displays to display aggregated or analyzed physiologic event information. In some examples, the physiologic event information can include any type of physiologic event that occurs, including expected or desirable physiologic events.

The operations of technique 2300 can help provide safer care for patients, including providing narcotic medications when helpful, while keeping a close eye on drug abuse by providers or patients. Taken at a high level, technique 2300 can help medical facilities evaluate which medications are most often abused by patients or stolen by providers, and to mitigate risk for insurers.

Any operations of the various methods described herein can be used in combination with or separately from one another, depending on the desired features and in consideration of constraints such as financial, space, material and manufacturing availability.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The terms approximately, about or substantially are defined herein as being within 10% of the stated value or arrangement.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NOTES AND VARIOUS EXAMPLES

Each of these non-limiting examples may stand on its own, or may be combined in various permutations or combinations with one or more of the other examples. The examples are supported by the preceding written description as well as the drawings of this disclosure.

Example 1 is a system for intravenous (IV) medications to deliver a medication from a syringe, the system comprising: a provider identification sensor configured to identify (e.g., sense) provider identification information; an injection portal configured to receive the syringe; one or more medication sensors configured to identify medication identification information that is coupled to the received syringe when the received syringe is located in the injection portal and configured to capture an image of the received syringe; one or more displays; one or more storage devices; and processing circuitry that is in electrical communication with the provider identification sensor, the one or more medication sensors, the one or more displays and the one or more storage devices, wherein the processing circuitry is configured to receive the provider identification information and to store the provider identification to at least one of the one or more storage devices, wherein the processing circuitry is configured to send instructions to at least one of the one or more displays to output a visual image or representation of the received syringe on the at least one display, wherein the processing circuitry is configured to determine a volume of medication dispensed from the received syringe based on an image of the syringe captured by the one or more medication sensors, and wherein the processing circuitry is configured to at least one of: save the volume of medication dispensed to the one or more storage devices or send instructions to at least one of the one or more displays to output the volume of medication dispensed on the at least one display.

In Example 2, the subject matter of Example 1 includes, wherein the injection portal further comprises: an injection port that is configured to fluidly couple to IV tubing; and at least one orienting member configured to guide the received syringe having a diameter that is a first diameter of a plurality of different diameters, to mate with the injection port.

In Example 3, the subject matter of Examples 1-2 includes, wherein at least one of the one or more medications sensors is located to capture an image of an inside of the injection portal, and wherein the processing circuitry is configured to receive a captured image of the received syringe and to calculate the volume of medication dispensed from the received syringe from the captured image by determining an internal diameter of the syringe and measuring a distance a plunger of the received syringe moves to calculate an injected volume.

In Example 4, the subject matter of Examples 1-3 includes, wherein at least one of the one or more medication sensors is an RFID interrogator, and wherein the medication identification information is an RFID tag.

In Example 5, the subject matter of Examples 1-4 includes, wherein at least one of the one or more medication sensors is configured to read the medication identification information and transmit a medication identity to the processing circuitry.

In Example 6, the subject matter of Examples 1-5 includes, wherein at least one of the one or more medication sensors is a machine vision digital camera.

In Example 7, the subject matter of Examples 1-6 includes, wherein when the provider identification sensor is configured to read the provider identification information and to generate provider identification data, and wherein the processing circuitry is configured to receive the generated provider identification information and to compare the generated provider identification information to withdrawing provider information, wherein the withdrawing provider information includes an identity of the provider who withdrew the syringe from a vending source.

In Example 8, the subject matter of Example 7 includes, wherein the provider identification sensor is a barcode reader, an RFID interrogator, a retinal scanner, a facial recognition scanner, or a fingerprint reader.

In Example 9, the subject matter of Examples 1-8 includes, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

In Example 10, the subject matter of Examples 1-9 includes, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

In Example 11, the subject matter of Examples 1-10 includes, an injection port located in the injection portal that is configured to fluidly couple the received syringe to IV tubing; and at least one clamp in electrical communication with the processing circuitry, wherein the processing circuitry is configured send an instruction to actuate the at least one clamp positioned one or more of upstream or downstream from the injection port, and wherein the processing circuitry is configured to send instructions to the at least one clamp to inhibit dispensing of the medication or an IV fluid when an adverse condition is determined by the processing circuitry.

Example 12 is a system for intravenous (IV) medications to deliver a medication from a syringe, the system comprising: a provider identification sensor configured to identify (e.g., sense) a provider; an injection portal configured to receive the syringe; one or more medication sensors configured to identify medication information that is coupled to the received syringe when the received syringe is located in the injection portal, wherein at least one of the one or more medication sensors is located to capture an image of an inside of the injection portal; one or more displays; one or more storage devices; and processing circuitry that is in electrical communication with the provider identification sensor, the one or more medication sensors, the one or more displays, and the one or more storage devices, wherein the processing circuitry is configured to receive the provider identification information and to store the provider identification to at least one of the one or more storage devices, wherein the processing circuitry is configured to send instructions to at least one of the one or more displays to output a visual image or representation of the received syringe on the at least one display, wherein the processing circuitry is configured to receive a captured image of the received syringe and to calculate a volume of medication dispensed from the received syringe from the captured image by determining an internal diameter of the syringe and measuring a distance a plunger of the received syringe moves to calculate an injected volume, and wherein the processing circuitry is configured to at least one of: save the volume of medication dispensed to the one or more storage devices or send instructions to at least one of the one or more displays to output the volume of medication dispensed on the at least one display.

In Example 13, the subject matter of Example 12 includes, wherein the injection portal further comprises: an injection port that is configured to fluidly couple to IV tubing; and at least one orienting member configured to guide the received syringe having a diameter that is a first diameter of a plurality of different diameters, to mate with the injection port.

In Example 14, the subject matter of Examples 12-13 includes, wherein at least one of the one or more medication sensors is an RFID interrogator, and wherein the medication identification information is an RFID tag.

In Example 15, the subject matter of Examples 12-14 includes, wherein at least one of the one or more medication sensors is configured to read the medication identification information and transmit a medication identity to the processing circuitry.

In Example 16, the subject matter of Examples 12-15 includes, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

In Example 17, the subject matter of Examples 12-16 includes, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

In Example 18, the subject matter of Examples 12-17 includes, an injection port located in the injection portal that is configured to fluidly couple the received syringe to IV tubing; and at least one clamp in electrical communication with the processing circuitry, wherein the processing circuitry is configured send an instruction to actuate the at least one clamp positioned one or more of upstream or downstream from the injection port, and wherein the processing circuitry is configured to send instructions to the at least one clamp to inhibit dispensing of the medication or an IV fluid when an adverse condition is determined by the processing circuitry.

Example 19 is a tamper-resistant, non-refillable syringe comprising: a cylindrical syringe barrel extending from a first end having an opening configured to receive a movable plunger to a second end adjacent a Luer taper connector; a tamper-resistant hypodermic needle-blocking obstruction proximate the Luer taper connector to prevent receiving of a hypodermic needle through the Luer taper connector and into the syringe barrel; and a plunger seal coupled to the plunger, the plunger seal having one or more angled barbs that allow the plunger to be moved in a direction towards the Luer taper connector, and wherein the angled barbs inhibit movement of the plunger in a direction away from the Luer taper connector to prevent refilling a syringe.

In Example 20, the subject matter of Example 19 includes, wherein a coupling interface between the plunger and the plunger seal is configured to disengage when the plunger is moved in a direction away from the Luer taper connector.

In Example 21, the subject matter of Examples 19-20 includes, wherein the plunger seal includes one or more spring wires molded into the plunger seal having barb tips formed by cut ends of the spring wires protruding outward from the plunger seal to poke into an inner surface of the syringe barrel.

In Example 22, the subject matter of Example 21 includes, wherein the one or more spring wires are angled toward the syringe barrel opening to allow movement of the plunger seal toward the Luer taper connector while inhibiting movement of the plunger seal in an opposite direction by the one or more spring wires poking into an inner surface of the syringe barrel when the plunger is moved away from the Luer taper connector.

In Example 23, the subject matter of Examples 19-22 includes, wherein the needle-blocking obstruction includes a polymer insert that is sized to fit against an inside surface of the syringe barrel proximate the Luer taper connector, the needle-blocking obstruction further including a solid central portion that directly opposes the opening to the Luer taper connector and one or more tortuous fluid channels that allow fluid flow in a longitudinal direction through the polymer insert and then in a transverse direction toward the opening to the Luer taper connector.

In Example 24, the subject matter of Example 23 includes, wherein the needle-blocking obstruction includes a metal plate that is located opposite the opening to the Luer taper connector by the polymer insert, and wherein the metal plate is configured to block the insertion of a hypodermic needle through the Luer taper connector and into the syringe barrel.

In Example 25, the subject matter of Examples 23-24 includes, wherein the polymer insert is sized to fit snuggly against the inside of the syringe barrel proximate the Luer taper connector, and wherein the polymer insert is bonded to the syringe barrel by one or more of a heat bond, ultrasonic bond, RF bond, adhesive bond or friction fit.

In Example 26, the subject matter of Examples 19-25 includes, wherein the needle-blocking obstruction proximate the Luer taper connector includes a zig-zag fluid channel located between the first end of the syringe barrel and a distal end of the Luer taper connector.

Example 27 is a system for delivering intravenous (IV) fluids from an IV bag fluidly that is coupled to a drip chamber and IV tubing, the system comprising: an IV scale configured to receive and support the IV bag; one or more sensors, wherein at least one of the one or more sensors is configured to identify an IV fluid in the IV bag hanging on the IV scale and wherein at least one of the one or more sensors is located adjacent to the received drip chamber and is configured to capture an image of the drip chamber; one or more displays; one or more storage devices; and processing circuitry that is in electrical communication with the IV scale, the one or more sensors, the one or more displays and the one or more storage devices, wherein the processing circuitry is configured to receive a medication identity and a captured image of the drip chamber from the one or more sensors, and wherein the processing circuitry is configured to determine a fluid flow rate by analyzing an image of fluid drops falling in the drip chamber including determining a size of drops and a number of drops per unit time; wherein the processing circuitry is configured to at least one of: save the fluid flow rate to one or more storage devices or send instructions to at least one of the one or more displays to output the fluid flow rate on at least one of the one or more displays.

In Example 28, the subject matter of Example 27 includes, wherein the IV scale includes a hanger configured to support the IV bag, and wherein the IV scale is configured to measure a combined weight of the IV bag, the IV drip chamber, the IV tubing and the fluids in the IV bag, and wherein the processing circuitry is configured to determine a reduction in a measured combined weight over time to determine a weight of the fluid removed from the IV bag and to convert the measured combined weight over time to a fluid flow rate and an infused fluid volume.

In Example 29, the subject matter of Examples 27-28 includes, a float located in the IV drip chamber, wherein when the processing circuitry determines from the captured image that the fluid drops in the drip chamber cannot be distinguished from one another and that the float is moving, the processing circuitry is configured to measure the fluid flow rate by determining a reduction of a combined weight of the IV bag, the IV drip chamber, the IV tubing and fluid in the IV bag over time.

In Example 30, the subject matter of Examples 27-29 includes, one or more electromechanical clamps that is in electrical communication with the processing circuitry, wherein the processing circuitry is configured to determine from the captured image that no fluid meniscus is present in the drip chamber, the processing circuitry sends an instruction to cause at least one of the one or more electromechanical clamps to compress the IV tubing to inhibit fluid flow prior to air entering the IV tubing.

Example 31 is at least one machine-readable medium including instructions that, when executed by processing circuitry, cause the processing circuitry to perform operations to implement of any of Examples 1-30.

Example 32 is an apparatus comprising means to implement of any of Examples 1-30.

Example 33 is a system to implement of any of Examples 1-30.

Example 34 is a method to implement of any of Examples 1-30.

What is claimed is:

1. A module for housing electronic and electromechanical medical equipment including a system to measure and record administration of one or more IV medications or fluids for IV administration, the module comprising:
   a housing having a lower section and a tower-like upper section, the housing configured to house waste heat-producing electronic and electromechanical medical equipment, and wherein the housing is configured to accommodate mounting of equipment controls, display screens and monitor screens at a convenient height for viewing and operating;
   a cowling that substantially confines waste heat generated by the waste heat-producing electronic and electromechanical medical equipment; and
   a system for measuring and recording the administration of the one or more IV medications and fluids, the system comprising:
   a sensor configured to identify at least one of the one or more IV medications or fluids; and
   a second sensor in electrical communication with processing circuitry configured to determine a volume of medication administered from a syringe or fluid administered from an IV bag through an IV drip chamber into an IV tubing based on an image generated by the second sensor.

2. The module of claim 1, the system to measure and record the administration of the one or more IV medications or fluids further comprising:
   an injection portal; and
   one or more orienting members, wherein the injection portal includes an injection port that is configured to be in fluid communication with the IV tubing and the one or more orienting members are configured to guide syringes of varying diameters to mate with the injection port within the injection portal.

3. A system for intravenous (IV) medications to deliver a medication from a syringe, the system comprising:
   a provider identification sensor configured to sense provider identification information;
   an injection portal configured to receive the syringe;
   one or more medication sensors configured to identify medication identification information that is coupled to the received syringe when the received syringe is located in the injection portal and configured to capture an image of the received syringe;
   one or more displays;
   one or more storage devices; and
   processing circuitry that is in electrical communication with the provider identification sensor, the one or more medication sensors, the one or more displays and the one or more storage devices,
   wherein the processing circuitry is configured to receive the provider identification information and to store the provider identification to at least one of the one or more storage devices,
   wherein the processing circuitry is configured to send instructions to at least one of the one or more displays to output a visual image or representation of the received syringe on the at least one display,
   wherein the processing circuitry is configured to determine a volume of medication dispensed from the received syringe based on an image of the syringe captured by the one or more medication sensors, and
   wherein the processing circuitry is configured to at least one of:
save the volume of medication dispensed to the one or more storage devices or send instructions to at least one of the one or more displays to output the volume of medication dispensed on the at least one display.

4. The system of claim 3, wherein the injection portal further comprises:
   an injection port that is configured to fluidly couple to IV tubing; and
   at least one orienting member configured to guide the received syringe having a diameter that is a first diameter of a plurality of different diameters, to mate with the injection port.

5. The system of claim 3, wherein at least one of the one or more medications sensors is located to capture an image of an inside of the injection portal, and
   wherein the processing circuitry is configured to receive a captured image of the received syringe and to calculate the volume of medication dispensed from the received syringe from the captured image by determining an internal diameter of the syringe and measuring a distance a plunger of the received syringe moves to calculate an injected volume.

6. The system of claim 3, wherein at least one of the one or more medication sensors is an RFID interrogator, and wherein the medication identification information is an RFID tag.

7. The system of claim 3, wherein at least one of the one or more medication sensors is configured to read the medication identification information and transmit a medication identity to the processing circuitry.

8. The system of claim 3, wherein at least one of the one or more medication sensors is a machine vision digital camera.

9. The system of claim 3, wherein when the provider identification sensor is configured to read the provider identification information and to generate provider identification data, and wherein the processing circuitry is configured to receive the generated provider identification information and to compare the generated provider identification information to withdrawing provider information, wherein the withdrawing provider information includes an identity of the provider who withdrew the syringe from a vending source.

10. The system of claim 8, wherein the provider identification sensor is a barcode reader, an RFID interrogator, a retinal scanner, a facial recognition scanner, or a fingerprint reader.

11. The system of claim 3, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

12. The system of claim 3, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

13. The system of claim 3, further comprising:
an injection port located in the injection portal that is configured to fluidly couple the received syringe to IV tubing; and
at least one clamp in electrical communication with the processing circuitry,
wherein the processing circuitry is configured send an instruction to actuate the at least one clamp positioned one or more of upstream or downstream from the injection port, and
wherein the processing circuitry is configured to send instructions to the at least one clamp to inhibit dispensing of the medication or an IV fluid when an adverse condition is determined by the processing circuitry.

14. A system for intravenous (IV) medications to deliver a medication from a syringe, the system comprising:
a provider identification sensor configured to identify a provider;
an injection portal configured to receive the syringe;
one or more medication sensors configured to identify medication information that is coupled to the received syringe when the received syringe is located in the injection portal, wherein at least one of the one or more medication sensors is located to capture an image of an inside of the injection portal;
one or more displays;
one or more storage devices; and
processing circuitry that is in electrical communication with the provider identification sensor, the one or more medication sensors, the one or more displays, and the one or more storage devices,
wherein the processing circuitry is configured to receive the provider identification information and to store the provider identification to at least one of the one or more storage devices,
wherein the processing circuitry is configured to send instructions to at least one of the one or more displays to output a visual image or representation of the received syringe on the at least one display,
wherein the processing circuitry is configured to receive a captured image of the received syringe and to calculate a volume of medication dispensed from the received syringe from the captured image by determining an internal diameter of the syringe and measuring a distance a plunger of the received syringe moves to calculate an injected volume, and
wherein the processing circuitry is configured to at least one of: save the volume of medication dispensed to the one or more storage devices or send instructions to at least one of the one or more displays to output the volume of medication dispensed on the at least one display.

15. The system of claim 14, wherein the injection portal further comprises:
an injection port that is configured to fluidly couple to IV tubing; and
at least one orienting member configured to guide the received syringe having a diameter that is a first diameter of a plurality of different diameters, to mate with the injection port.

16. The system of claim 14, wherein at least one of the one or more medication sensors is an RFID interrogator, and wherein the medication identification information is an RFID tag.

17. The system of claim 14, wherein at least one of the one or more medication sensors is configured to read the medication identification information and transmit a medication identity to the processing circuitry.

18. The system of claim 14, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

19. The system of claim 14, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

20. The system of claim 14, further comprising:
an injection port located in the injection portal that is configured to fluidly couple the received syringe to IV tubing; and
at least one clamp in electrical communication with the processing circuitry,
wherein the processing circuitry is configured send an instruction to actuate the at least one clamp positioned one or more of upstream or downstream from the injection port, and
wherein the processing circuitry is configured to send instructions to the at least one clamp to inhibit dispensing of the medication or an IV fluid when an adverse condition is determined by the processing circuitry.

* * * * *